United States Patent [19]
Gupta et al.

[11] Patent Number: 6,136,327
[45] Date of Patent: Oct. 24, 2000

[54] STEREOSPECIFIC DELIVERY OF A DRUG USING ELECTROTRANSPORT

[75] Inventors: Suneel K. Gupta, Sunnyvale; Gayatri Sathyan, Mountain View, both of Calif.; Rama Padmanabhan, Arden Hills, Minn.

[73] Assignee: ALZA Corporation, Mountain View, Calif.

[21] Appl. No.: 08/982,245

[22] Filed: Dec. 1, 1997

[51] Int. Cl.[7] .................................................. A61K 9/70
[52] U.S. Cl. .......................... 424/400; 424/443; 424/447; 424/449; 424/451; 424/457; 424/464; 424/468; 424/469; 424/472; 424/473
[58] Field of Search .................................. 424/457, 443, 424/468–9, 447, 472, 449, 473, 464

[56] References Cited

U.S. PATENT DOCUMENTS

| 4,818,541 | 4/1989 | Sanderson | 424/448 |
|---|---|---|---|
| 4,927,854 | 5/1990 | Sunshima et al. | 514/570 |
| 5,091,182 | 2/1992 | Ong | 424/400 |
| 5,114,946 | 5/1992 | Lawter et al. | 514/279 |
| 5,147,296 | 9/1992 | Theuwes et al. | 604/20 |
| 5,338,550 | 8/1994 | Edgren et al. | 424/473 |
| 5,589,498 | 12/1996 | Mohr et al. | 514/413 |
| 5,591,767 | 1/1997 | Mohr et al. | 514/413 |

FOREIGN PATENT DOCUMENTS

| 94/10985 | 5/1994 | WIPO | A61K 9/70 |
|---|---|---|---|
| 96/31251 | 10/1996 | WIPO | A61N 1/30 |
| 97/04835 | 2/1997 | WIPO | A61N 1/30 |

OTHER PUBLICATIONS

Guzman et al., "Absolute Configuration of (–)–5–Benzoyl–1,2–dihydro–3H–pyrrolo[1,2–a]pyrrole–1–carboxylic Acid, the Active Enantiomer of Ketorolac," *J. Med. Chem.* (1986) 29:589–591.

Hayball et al., "Stereoselective Analysis of Ketorolac in Human Plasma by High–Performance Liquid Chromatography," *Chirality* (1993) 5:31–35.

Mroszczak, "Pharmacokinetics of (–)S and (+)R Enantiomers of Ketorolac (K) in Humans Following Administration of Racemic Ketorolac Tromethamine (KT)," *Clin Pharmacol Ther*, (1991) 49:126.

Stinson, "Chiral Drugs," *C& EN Northeast News Bureau*, (1992) 46–48, 54,56,58,63–66,68,70,72,74,76,78–79.

*Primary Examiner*—Jose' G. Dees
*Assistant Examiner*—Kathryne E. Shelborne
*Attorney, Agent, or Firm*—Owen J. Bates; D. Byron Miller; Steven F. Stone

[57] ABSTRACT

Preferential delivery via electrotransport of a preferred isomeric form of a pharmaceutically active chiral compound from a mixture of the isomeric forms of said compound is provided. A method of decreasing the delivery via electrotransport of a less preferred isomer of a drug is also provided. Drug delivery devices suitable for such preferential delivery and methods of making the same are also provided.

22 Claims, 3 Drawing Sheets

STEREOSPECIFIC DELIVERY OF A DRUG USING ELECTROTRANSPORT

TECHNICAL FIELD

This invention relates generally to drug delivery. More particularly, the invention relates to the use of electrotransport to effect stereospecific drug delivery, i.e., preferential delivery of a single preferred enantiomer of a chiral drug from a pharmaceutical formulation containing the drug as a mixture of isomers.

BACKGROUND

A number of drugs contain chiral centers and thus can exist in two or more isomeric forms. A drug with a single chiral center can be formed as two "mirror-image" isomers, known as "enantiomers." In many instances, the enantiomers exhibit differences in pharmacokinetic properties, e.g., metabolism, protein binding, or the like, and/or pharmacological properties, e.g., the type of activity displayed, the degree of activity, toxicity, or the like. Isolation of a single enantiomer from a mixture, i.e., "resolution" of the mixture, is typically carried out by reaction with a standard asymmetric substance, followed by separation of the different products using conventional means. Fractional crystallization is another technique which may be employed to isolate a single enantiomer. Frequently, however, isolation of a single enantiomer from a mixture is difficult, as the two enantiomers within the mixture are by definition identical in terms of molecular composition and thus, in many instances, are substantially similar in reactivity. Alternatively, a single enantiomer of a drug or other compound may be prepared using a stereospecific synthesis which gives rise to the product in enantiomerically pure form. Such syntheses are typically somewhat difficult to implement and often do not provide the desired product in high yield.

Recent reports detail the lengths undertaken in order to obtain purified isomers of useful drugs. For example, U.S. Pat. No. 5,545,745 to Gao et al. claims a multistep process for preparing optically pure albuterol, employing reaction of a mixture of albuterol isomers with a chiral acid and selective crystallization of one of the products, followed by debenzylation to yield optically pure albuterol. U.S. Pat. No. 5,442,118 to Gao et al. claims a method of asymmetric synthesis of (R) and (S) arylethanolamines from aminoketones, useful for the preparation of pharmaceutical agents such as albuterol, terbutaline, isoproterenol and sotalol, using a borane reducing agent in the presence of a chiral 1,3,2-oxazaborolidine catalyst, wherein the reagents must be added in a specific order. U.S. Pat. No. 5,516,943 to Gao et al. describes the stereoselective conversion of a trans-1-amino-2-hydroxycycloalkane to the cis isomer by acylating the amine group and then treating with a strong acid; also disclosed is the direct formation of particular isomers of aminoindanol from indene using exotic chiral catalysts. U.S. Pat. No. 5,498,625 to Evans et al. describes the enzymatic production of one enantiomer of a lactam by reacting a racemic γ lactam with a stereospecific lactamase. U.S. Pat. No. 4,800,162 to Matson claims a method of resolving a racemic mixture by passing a solution containing the mixture through a filtering device having a stereoselective enzyme attached to the filter matrix on a first side: the enzyme selectively reacts with one isomer, creating a product which is then more soluble in an immiscible solvent flowing in the opposite direction on the opposite side of the matrix; the product then diffuses across the matrix, yielding a pure solution of enantiomeric product on the opposite side and producing a pure solution of the unreacted enantiomer on the first side.

As can be seen, elaborate efforts have been made in order to produce purified isomers of pharmacologically active agents.

With chiral drugs, if one enantiomer is pharmacologically more active, less toxic, or has a preferred disposition in the body as compared with the other enantiomer, it would be therapeutically more beneficial to administer that enantiomer preferentially. In this way, the patient undergoing treatment would be exposed to a lower total dose of the drug, or to a lower amount of a toxic isomer. Costly and complicated stereospecific synthesis or purification schemes would then be unnecessary.

Accordingly, there is a need in the art for a means of drug administration which enables preferential delivery of a single enantiomer of a chiral drug.

International Patent Publication No. WO 94/10985 describes the benefits provided by transdermal delivery of the active enantiomer of ketorolac compared to delivery of the racemic mixture. The active enantiomer was found to have a more rapid clearance than the other enantiomer, so that the continuous delivery provided by a transdermal system allowed for even lower dosages to be used than expected. That is, whereas one might expect that half of the total amount of the pure enantiomer would be as effective as the full dose of the racemic mixture, even less than half the amount of the pure enantiomer was found to be effective. This was attributed to the more rapid clearance and shorter half-life of the active enantiomer. Continuous delivery using the passive transdermal system provided a more steady level of the minimum therapeutic amount of the active enantiomer as compared with periodic dosing of the racemic mixture by immediate release oral or parenteral administration. Passive transdermal delivery was claimed to be beneficial for all enantiomers with high clearance values and short half-lives. Problems with passive transdermal drug delivery systems were also discussed, including the limits on the doses capable of being provided because of the limited permeability of the stratum corneum layer of the skin and the unacceptability of large patches to patients because of contact-related side effects, aesthetics, comfort and wearability.

The melting temperature of a drug is believed to be one factor limiting the ability of that drug to permeate the skin. Lawter and Pawelchak (U.S. Pat. No. 5,114,946) claimed that, for a chiral drug that is a solid at or above skin temperature, purified enantiomers or nonracemic mixtures of the drug display faster passive transdermal delivery rates when the purified enantiomers or the nonracemic mixtures have melting temperatures 5°–10° C. below that of the racemic mixture. However, no increase in the flux rate of one isomer relative to the other isomer in a mixture was noted.

Sanderson (U.S. Pat. No. 4,818,541) similarly reported that the purified individual isomers of phenylpropanolamine gave rise to faster transdermal penetration rates compared to the racemic mixture. The mechanism by which this occurred was not stated with certainty, but the increased solubility of the individual isomers compared to the mixture was suggested as one possibility. Each of the four individual purified isomers exhibited nearly identical flux rates.

The inventors herein have now found that passive transdermal drug delivery of a composition containing a drug (ketorolac) in the form of a racemic mixture does not provide for any significant difference in flux between the two isomers. This is consistent with previous reports that (−) ketorolac and racemic ketorolac have similar flux characteristics when used in several different types of passive transdermal systems (U.S. Pat. No. 5,589,498 to Mohr et al.). (−) Ketorolac is the active enantiomer of ketorolac, a non-steroidal anti-inflammatory analgesic which can produce gastrointestinal side effects when delivered orally. Transdermal patches of the adhesive matrix type, reservoir type, and monolithic matrix type were all reported to deliver similar flux rates of (−) ketorolac and racemic ketorolac.

Unexpectedly, electrotransport drug delivery has been discovered to give rise to a substantial differential in the rate of transport of two enantiomers contained in a mixture. Prior to applicants' invention, it was believed that the capability of administering a drug using electrotransport was solely a function of the drug's physico-chemical properties; now, it is clear that electrotransport drug delivery can be stereospecific as well.

In contrast to passive transdermal or transmucosal systems, electrotransport has been found to provide for the preferential delivery of one isomer from a mixture while providing a faster overall flux rate than passive delivery systems, and requires no special synthetic or purification schemes. Additionally, preferential isomer delivery via electrotransport is not limited to particular mixtures of drug isomers that have a lower melting temperature than the racemic mixture, or to enantiomers with high clearance values and low half-lives. As a result of the increased transfer rate, electrotransport can permit a shorter time of delivery or the use of a smaller, more acceptable coverage area in order to deliver the desired amount of compound than such passive delivery systems. Generally, it is preferred that at least a 20% increase in the rate of in vivo delivery of the preferred isomer is achieved. However, a smaller increase in rate of delivery, of about 5 or 10%, may prove acceptable in some cases, for example where the drug is particularly expensive.

By eliminating the need for stereospecific synthesis or complicated purification procedures, selective delivery of one isomer via electrotransport can lead to improvements in therapeutic costs and treatment regimens. Costs of synthesis can be decreased by eliminating the need for stereospecific synthesis or purification of one isomer from a mixture. A simpler scheme for synthesis and purification can result in a lowered generation of hazardous materials and a lessened exposure of personnel to those materials. Additionally, stereoselective electrotransport can be used to preferentially deliver one isomer where stereospecific synthesis or purification of that isomer has not yet been achieved. By receiving an increased amount of the preferred isomer, patients can thus be exposed to a lesser total amount of compound or be treated for a shorter time or over a smaller region of their body.

Furthermore, even if passive drug delivery could give rise to differences in flux rates of desired isomers, electrotransport can increase this differential while providing higher overall flux rates than passive systems, allowing for smaller, more acceptable delivery devices. Similarly, where chemical synthesis or purification schemes provide a greater proportion of the desired enantiomer in a mixture, electrotransport delivery of the mixture can further increase the proportion of desired enantiomer which is delivered.

Herein the term "electrotransport drug delivery" is used to refer to the delivery of pharmaceutically active agents through an area of the body surface by means of an electromotive force to a drug-containing reservoir. The drug may be delivered by electromigration, electroporation, electroosmosis or any combination thereof. Electroosmosis has also been referred to as electrohydrokinesis, electro-convection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation." Any electrically assisted transport of species enhanced by modifications or alterations to the body surface (e.g., formation of pores in the skin) are also included in the term "electrotransport" as used herein. Thus, as used herein, the term "electrotransport" refers to (1) the delivery of charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or agents by the combined processes of electromigration and electroosmosis.

SUMMARY OF THE INVENTION

The invention thus provides a method for using electrotransport drug delivery to preferentially deliver a preferred isomer from a pharmaceutical formulation containing the drug as a mixture of preferred and less preferred isomers. The method involves (a) applying to an area of the body surface a formulation containing the drug as a mixture of isomers, and (b) delivering the formulation by electrotransport through the same area of the body surface simultaneously with or subsequent to step (a), so that the transport of a preferred isomer is enhanced relative to the transport of a less preferred isomer. Generally, the method will involve: placing an electrotransport drug reservoir in drug-transmitting relation to the selected area of the body surface, the reservoir containing the aforementioned formulation; electrically connecting the drug reservoir to a source of electrical power; and then delivering the drug through the body surface by electrotransport. As explained above, the process is carried out such that the preferred enantiomer is delivered at a rate sufficient to induce a therapeutic effect, while the corresponding, second enantiomer is delivered at a substantially lower rate. A method of decreasing the delivery via electrotransport of a less preferred isomer of a drug is also provided. Drug delivery devices suitable for such preferential delivery and methods of making the same are also provided.

DETAILED DESCRIPTION OF THE INVENTION

Figure 1:
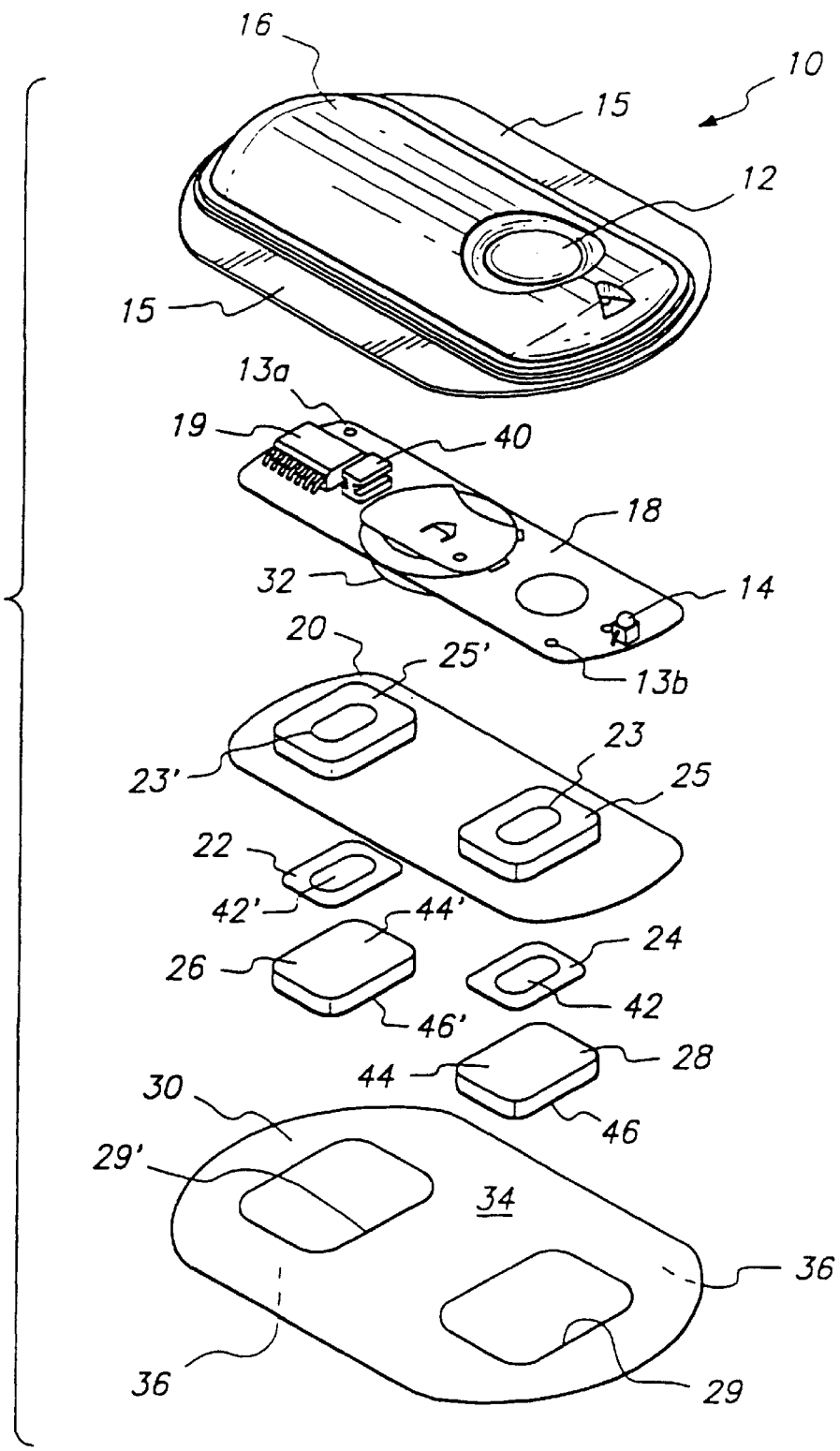
FIG. 1 is a perspective view of an electrotransport drug delivery device which may be used in conjunction with the present invention.

It is to be understood that this invention is not limited to specific pharmaceutical compositions, carriers, drug delivery device structures, or the like, as such may vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. Thus, reference to "a drug" includes mixtures of drugs, reference to "an enhancer" includes mixtures of enhancers, reference to "a carrier" includes mixtures of carriers, and the like.

In describing and claiming the present invention, the following terminology will be used in accordance with the definitions set out below.

The terms "drug," "active agent" or "pharmacologically active agent" are used interchangeably herein to mean any chemical material or compound which induces a desired local or systemic effect in an individual subject (human or animal), and is capable of being delivered to the subject by electrotransport.

By the term "dosage" is meant the amount of drug delivered from an electrotransport delivery device. The term is intended to encompass the amount of drug delivered per unit time, the total amount of drug delivered over a period of time, the duration of time over which the drug is to be delivered, and the like.

The term "optional" as used herein, as in the recitation that the presence of a particular component in a pharmaceutical composition is "optional," means that the component may or may not be present, and includes instances where the component is present and instances where the component is not present.

Drugs, therapeutics or otherwise active agents useful in connection with the present invention include any pharmaceutical compound that is capable of being delivered by electrotransport, wherein the compound exists in the form of an isomeric mixture, and further wherein it is desired to preferentially deliver a preferred isomer from those in the mixture, or wherein it is desired to preferentially not deliver a less preferred isomer. This includes drugs with one, two, or more chiral centers, having two, four, or more isomers, wherein one, two, or more of the isomers are preferred, and/or one, two, or more of the isomers are less preferred. The active agents which may be administered using the methodology of the invention includes agents in all of the major therapeutic areas. For example, suitable active agents include, but are not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary anticholinergics, sympathomimetics, xanthine derivatives, calcium channel blockers, beta-blockers, beta-agonists, antiarrhythmics, antihypertensives, ACE inhibitors, diuretics, vasodilators, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetics, prostaglandins, psychostimulants, sedatives and tranquilizers. The invention is also useful in conjunction with the electrotransport delivery of proteins, peptides and fragments thereof.

A particularly preferred drug which can be administered using the methodology of the invention is the anti-inflammatory, analgesic agent ketorolac ((±)-benzoyl-2,3-dihydro-1H-pyrrolizine-1-carboxylic acid)), as the S-isomer of the drug has been found to be significantly more active than the R-isomer. It has been established that the S:R ratios of anti-inflammatory and analgesic activities are 57 and 230, respectively (Mroszczak et al. (1994) *Clin. Pharm Ther.* 42:126; Hayball et al. (1993) *Chirality* 5:31–35). Therefore, it is advantageous to deliver the single S-isomer preferentially.

Other enantiomeric drugs where preferential isomeric delivery is desirable include ibuprofen (the S-isomer is the active ingredient), terfenadine (the S-isomer is active), nicotine (the S (−) isomer has been found less irritating in transdermal patch formulations), nebivolol (the (+) isomer is a β-blocker, while the (−) isomer is a vasodilating agent), zacopride (one isomer is a 5-HT$_3$ blocker, the other is an agonist), tenormin (the S-isomer is a β-blocker), imovane (the S-isomer is a sedative), Ansaid (the S-isomer is a nonsteroidal antiinflammatory drug, or "NSAID"), and Orudis (the S-isomer is an NSAID).

Further nonlimiting examples of drugs which are available as racemates but wherein one isomer would be preferred for delivery include acebutolol, acenocoumarol, albuterol/salbutamol, alprenolol, amosulolol, amoxicillin, ampicillin, astemizole, atenolol, baclofen, benazepril, benzyl glutamate, betaxolol, bethanecol, bisprolol, bopindolol, bucumolol, bufetolol, bufuralol, bunitrolol, bupranolol, butaclamol, butoconazole, butofilolol, calcitonin, camazepam, captopril, captopril, caraxolol, carvedilol, cefadroxil, cicloprofen, ciprofloxacin, corticosteroids, cromakalim, curteolol, cytrabine, deprenyl, dexfenfluramine, dihydroxythebaine, diltiazem, disopyramide, dobutamine, enalapril, ephedrine, estradiol, ethambutol, fenbuphen, fenfluramine, fenoprofen, fluorogesterone, fluoxetine, flurbiprofen, gonadorelin, hexobarbital, ibuprofen, indenolol, indoprofen, ketamine, ketodesogestrel/estrogen, ketoprofen, lisinopril, lorazepam, lovastatin, meclizine, mepindolol, metaproteranol, methadone, methyldopa, metipranolol, metoprolol, minoxiprofen, 3-hydroxy-N-methyl morphinan, nadolol, naproxen, nicardipine, nilvadipine, nitanol, norfloxacin, norgestrel, ofloxacin, oxaprotiline, oxpranolol, oxybutynin, perindopril, phenprocoumon, phenylpropanolamine, pindolol, pirprofen, polycloramphetamine, prilocaine, progestinpropanolol, propoxyphene, sertraline, sotalol, steroids, suprofen, terbutaline, terfenadine, testosterone, thioridazine, timolol, tocainide, toliprolol, toloxaton, tomoxetine, triamcinolone, verapamil, viloxazin, warfarin, xibenolol, and 1,4-dihydropyridine chiral compounds.

The compounds may be in the form of pharmaceutically acceptable salts, esters, amides or prodrugs, or may be modified by appending one or more appropriate functionalities to enhance selected biological properties. Such modifications are known in the art and include those which increase biological penetration into a given biological system, increase bioavailability, increase solubility to allow administration by a particular mode, and the like.

Compounds may be converted into pharmaceutically acceptable salts, and the salts may be converted into the free compound using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

Acid addition salts are prepared from the free base (e.g., compounds having a neutral —NH$_2$ or cyclic amine group)

using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preferred acid addition salts of the present compounds are the citrate, fumarate, succinate, benzoate and malonate salts.

Basic salts of acid moieties which may be present (e.g., carboxylic acid groups) can be prepared in a similar manner using pharmaceutically acceptable inorganic or organic bases. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, trimethylamine, triethylamine, benzylamine, dibenzylamine or $\alpha$- or $\beta$-phenylethylamine, and heterocyclic bases such as piperidine, 1-methylpiperidine and morpholine.

Compounds may also be converted into pharmaceutically acceptable esters. Suitable esters include branched or unbranched, saturated or unsaturated $C_1$ to $C_6$ alkyl esters, for example, methyl, ethyl and vinyl esters.

Preparation of esters involves functionalization of hydroxyl and/or carboxyl groups which may be present. Esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures. Preparation of amides and prodrugs can be performed in an analogous manner.

Electrotransport devices which can be employed in the method of the present invention typically comprise at least two electrodes. Each of these electrodes is placed in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the drug to be driven into the body is positively charged, then the positive electrode (the anode) will be the active electrode and the negative electrode (the cathode) will serve as the counter electrode, completing the circuit. If the drug to be delivered is negatively charged, then the cathodic electrode will be the active electrode and the anodic electrode will be the counter electrode.

Electrotransport devices additionally require a drug reservoir or source of the. pharmaceutically active agent which is to be delivered or introduced into the body. Such drug reservoirs are connected to the anode or the cathode of the electrotransport device to provide a fixed or renewable source of one or more desired species or agents. The drug reservoirs are usually polymeric hydrogels. Suitable polymers useful for forming hydrogel drug reservoirs include: polyvinyl alcohols; polyvinyl-pyrrolidone; cellulosic polymers, e.g., hydroxyethyl cellulose, hydroxypropyl cellulose, hydroxypropyl methylcellulose, carboxymethyl cellulose, and the like; polyurethanes; polyethylene oxides; polyanhydrides; polyvinyl pyrrolidone/vinyl acetate copolymers, and the like; and mixtures and copolymers thereof. One material suitable for electrotransport drug reservoirs is polyvinyl alcohol, which has been found to have good skin biocompatibility.

The drug reservoirs may contain a number of components, such as preservatives, solubilizing agents, pH modifiers, antimicrobials, antifungals, anti-inflammatory agents, stabilizers, surfactants, and the like. The drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, dimethylsulfoxide (DMSO), dimethyl formamide (DMF), N,N-dimethylacetamide (DMA), decylmethylsulfoxide ($C_{10}$MSO), $C_2$–$C_6$ alkanediols, and the 1-substituted azacycloheptan-2-ones, particularly 1-n-dodecylcyclazacycloheptan-2-one (available under the trademark Azone® from Whitby Research Incorporated, Richmond, Va.), alcohols, and the like.

It will be appreciated by those working in the field that the present method can be used in conjunction with a wide variety of electrotransport drug delivery systems, as the method is not limited in any way in this regard. For examples of electrotransport drug delivery systems, reference may be had to U.S. Pat. No. 5,147,296 to Theeuwes et al., U.S. Pat. No. 5,080,646 to Theeuwes et al., U.S. Pat. No. 5,169,382 to Theeuwes et al., and U.S. Pat. No. 5,169,383 to Gyory et al., the disclosures of which are incorporated by reference herein.

FIG. 1 illustrates a representative electrotransport delivery device that may be used in conjunction with the present method. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and drug/ chemical reservoirs 26,28, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained by lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

The reservoirs 26 and 28 comprise a gel matrix, with at least one of the reservoirs comprised of the hydrogel formulation of the invention. Drug concentrations in the range of approximately $1 \times 10^{-4}$ M to 1.0 M or more can be used, with drug concentrations in the lower portion of the range being preferred. Concentrations lower than about $1 \times 10^{-4}$ M may also be effective, particularly with peptide or protein drugs. Generally it is preferred that the drug concentration not become so low during drug delivery that flux becomes dependent on drug concentration, but remains dependent on current. For an expensive drug, however, this may not be possible. Factors which affect the ultimate device formulation include device size, drug solubility, drug cost, and dosing regimen.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

The transport of the R- and S-isomers of ketorolac was evaluated using passive transdermal delivery and electrotransport, in a study conducted in healthy volunteers. Intravenous bolus administration of 24 mg racemic ketorolac served as the reference treatment. The relative amounts of R- and S-ketorolac absorbed following passive transdermal and electrotransport administration were determined relative to intravenous R- and S-ketorolac clearance (assuming that the racemic ketorolac contained equal amounts of the R- and S-isomers). The mean amounts of R- and S-ketorolac absorbed following passive transdermal administration were 5.0 mg and 4.8 mg (mean total=9.8 mg) respectively, and, following electrotransport administration, were 7.9 and 11.7 mg (mean total=19.6 mg) respectively. Following passive transdermal administration, the amount of R-ketorolac absorbed was similar to that of S-ketorolac ($p > 0.5$). However, following electrotransport administration the mean amount of R-ketorolac absorbed was found to be lower than that of S-ketorolac absorbed. The S/R ratio of amount absorbed ranged from 0.8 to 1.43 (mean, 1.15; median, 1.18).

EXAMPLE 2

Drugs comprising mixtures of enantiomers are evaluated to determine a preferred isomer. Purified isomers as well as mixtures of isomers are delivered to test subjects and the efficacy, pharmacokinetics and pharmacodynamic profile of the isomers are determined. Preferred isomers are identified as those that are effective and exhibit some beneficial feature as compared to a mixture of isomers, for example improved therapeutic index, improved activity, improved half-life, lower effective dosage, lower toxicity, fewer or lessened side effects, or the ability to be delivered via electrotransport to an effective therapeutic level in an acceptable patch size, and the like.

EXAMPLE 3

A mixture of isomeric forms of a drug is incorporated into an electrotransport device. The device is applied to test subjects, and blood samples are subsequently taken from the subjects at various time intervals before, during and after treatment. Plasma concentrations of the preferred isomer and the other isomers are determined. Drugs for which electrotransport provides increased uptake of the preferred isomer are identified. Generally, it is preferred that at least a 20% increase in the rate of in vivo delivery of the preferred isomer is achieved. However, a smaller increase in rate of delivery, of about 5 or 10%, may prove acceptable in some cases, for example where the drug is particularly expensive.

EXAMPLE 4

A study was performed in order to compare the pharmacokinetic parameters of R- and S-ketorolac following intravenous, passive transdermal and electrotransport administration of a racemic mixture of ketorolac.

SCREENING PROCEDURES

Twelve healthy male volunteers were enrolled in a pilot feasibility study. Subjects were required to undergo a pre-study screening to evaluate whether they met study inclusion or exclusion criteria. Screening procedures included a medical history, physical exam, electrocardiogram and clinical laboratory tests.

MATERIALS AND METHODS

Study Design:

The study was an open-label, randomized, three-treatment crossover pharmacokinetics study designed to compare plasma ketorolac concentrations during 24-hour treatment regimens with an electrotransport system ("ETS"), a (passive) therapeutic transdermal system ("TTS") and intravenous ketorolac bolus injection.

Treatment Overview and Randomization:

The ketorolac treatments are listed below; there was a washout period of at least 6 days between treatments.

| | |
|---|---|
| ETS (ketorolac): | Ketorolac delivered with electrotransport from a total cathode area of 18 cm$^2$, at a current density of 100 $\mu$A/cm$^2$, for 24 hours |
| TTS (ketorolac): | Ketorolac delivered passively through the skin from three systems, total area 75 cm$^2$, for 24 hours |
| Intravenous ketorolac: | Intravenous bolus injection of ketorolac, 12 mg of free acid (18 mg of ketorolac tromethamine salt), at Hour 0 an Hour 12 (a total of 24 mg). |

Subjects were assigned randomly to receive the three ketorolac treatments in one of the following randomization schemes:

| Sequence | Subject Number |
|---|---|
| ETS, TTS, Bolus | 103, 106, 107, 110 |
| TTS, Bolus, ETS | 101, 104, 108, 112 |
| Bolus, ETS, TTS | 102, 105, 109, 111 |

ETS Treatment:

During the ETS (ketorolac) treatment, each subject was expected to receive an estimated 26 mg of ketorolac free acid over a 24-hour period, delivered by electrotransport from a total cathode area of 18 cm$^2$, based on an estimated in vitro flux rate of 60 $\mu$g/cm$^2$/h.

ETS System Description:

The ALZA Model 6443 Electrical Current Source ("ECS"), in combination with the Electrotransport Delivery Platform containing the active drug gel at the cathode and the pharmacologically inactive gel at the anode, makes up the electrotransport drug delivery system.

The Model 6443 ECS is a reusable electrical current regulator (controller). The controller was set in the direct current ("DC") mode to provide continuous electrical current for the delivery of ketorolac during ETS treatment.

The electrotransport delivery platform consisted of a housing containing the anode and cathode electrodes and two gel reservoirs. The cathode reservoir was designed to hold the active gel imbibed with ketorolac and was 6 cm$^2$. The anode reservoir comprised a pharmacologically inactive gel and was 6 cm$^2$. The inactive anode gels were placed against the anode electrode during manufacture and assembly of the housing. The drug-imbibed cathode gels were inserted into the platform just prior to use. A pressure sensitive adhesive permitted application of the system to the skin. The delivery platform was connected to the ECS by a cable.

Three electrotransport systems, with a total cathode gel area of 18 cm$^2$, were applied to the upper arms of each subject in this study. Each of the three controllers was set to provide a total direct current of 0.6 mA, which maintained a current density of 100 $\mu$A/cm$^2$.

A current and voltage check of the controller were performed using a voltmeter at hours 0, 2, 4, 8, 12 and 24 of the ETS application.

If the voltage exceeded 15 volts or the current was not within ±20% of target value, the controller was adjusted. If adjustment did not correct the problem, the controller was replaced and the subject continued in the study.

TTS Treatment:

During TTS treatment, each subject was expected to receive an estimated 50 mg of ketorolac free acid over a 24-hour period, delivered passively through the skin from a total application area of 75 cm$^2$ based on an estimated in vitro flux rate of 25 to 30 $\mu$g/cm$^2$/h.

TTS System Description:

The TTS systems were produced with a backing and protective liner in a 25 cm$^2$ size. The system formulation contained drug (free acid), ethylene vinyl acetate (40% vinyl acetate), glycerol monolaurate, and Ceraphyl® 31. Three TTS monoliths, with a total surface area of 75 cm$^2$, were used to deliver the drug. The combined systems contained 135 mg of ketorolac free acid. Because the systems were not self-adhesive, an adhesive overlay was required to ensure good skin contact.

Intravenous Ketorolac Bolus Injection Treatment:

During the intravenous bolus treatment, each subject received a total of 24 mg of ketorolac free acid (36 mg of ketorolac tromethamine salt). Drug was delivered by IV bolus injections of 12 mg of ketorolac free acid (18 mg of ketorolac tromethamine salt) which were administered at Hour 0 and at Hour 12. A 1 mL aliquot of each ketorolac solution was retained directly after syringe preparation and prior to injection.

Treatment Schedule:

Initially either the ETS or the TTS was applied, or the first intravenous injection was administered. ETS and TTS treatments continued for 24 hours, and the bolus treatment was completed after the second dose at 12 hours. Blood and urine samples were collected at intervals during a 48-hour period after initiation of each ketorolac treatment regimen.

After completion of all three drug treatments and blood and urine collection phases, a post-study physical examination, electrocardiogram, and clinical laboratory tests were performed.

Blood Sampling for Pharmacokinetics Assessment:

Blood samples, 7 mL each, were collected from each subject at intervals during the 48 hour period after initiation of treatment.

Plasma levels of ketorolac were determined by HPLC assay, performed at the Clinical Pharmacology Division of the School of Medicine at Indiana University, Wishard Memorial Hospital, Indianapolis, Ind.

Topical Evaluations:

Skin site assessments were conducted at intervals at both the anode and the cathode sites of the electrotransport system and at the sites to which the TTS (ketorolac) systems were applied.

Pharmacokinetics Methods:

Actual blood sample collection times were used for all calculations and data were summarized by nominal sampling times. Plasma ketorolac concentrations below the assay quantification limit of 20 ng/mL were assigned a value of zero.

The maximal observed plasma concentrations ($C_{max}$) of R- and S-ketorolac and the corresponding sampling times ($T_{max}$), expressed in hours, were determined over the entire sampling interval following TTS and ETS treatment.

The apparent elimination rate constants (k) for both R- and S-ketorolac were estimated by linear regression of log-transformed plasma concentrations during the terminal log-linear decline phase following intravenous administration. Apparent half-life ($t_{1/2}$) values were calculated as 0.693/k.

The area under the plasma R- and S-ketorolac concentration time profiles, from Hour 0 to the last detectable concentration at time t ($AUC_t$), were determined by the linear trapezoidal method. The AUC value extrapolated to infinity ($AUC_{inf}$) was determined as the sum of $AUC_t$ and the area extrapolated to infinity, and was calculated by the concentration at time t ($C_t$) divided by k. The average steady-state drug concentrations ($C_{avg}$) were calculated as $AUC_{inf}/24$.

The R- and S-ketorolac $AUC_{inf}$ ratio was determined for all three treatments. The amounts of R- and S-ketorolac absorbed following the ETS (ketorolac) and TTS (ketorolac) treatments were calculated using the estimated intravenous clearance (Dose/$AUC_{inf}$) as given in Equation 1, which assumed no interconversion between the enantiomers:

$$\text{Amount absorbed} = AUC_{inf(TTS/ETS)} * CL_{IV} \quad \text{(Equation 1)}$$

The disposition of R- and S-ketorolac following intravenous administration could be best described by a two-compartment open model. The pharmacokinetics parameters following intravenous administration of R- and S-ketorolac were estimated by non-linear regression of the plasma concentration-time profile (Equation 2). The rate of drug input and the absorption rate constant following both ETS (ketorolac) and TTS (ketorolac) administration were then estimated by fitting the respective plasma concentration-time profile to Equation 3. The pharmacokinetics parameters such as V, K1, K2, and K21 estimated from intravenous data were used as constants.

$$C(t) = \frac{D}{V*(K1-K2)} * \left[\frac{(K21-K1)*(1-\exp^{(di*K1*\tau)})*(\exp^{(-K1*t)})}{(1-\exp^{(K1*\tau)})} + \frac{(K21-K2)*(1-\exp^{(di*K2*\tau)})*(\exp^{(-K2*t)})}{(1-\exp^{(K2*\tau)})}\right] \quad \text{(Equation 2)}$$

$$C(t) = \frac{R*K_a}{V} * \left[\frac{(1-\exp^{(K1*\theta)})*(\exp^{(-K1*(t-T))})*(K21-K1)}{K1*(K1-K2)*(Ka-K1)} + \frac{(1-\exp^{(K2*\theta)})*(\exp^{(-K2*(t-T))})*(K21-K2)}{K2*(K1-K2)*(Ka-K2)} - \frac{(1-\exp^{(Ka*\theta)})*(\exp^{(-Ka*(t-T))})*(K21-Ka)}{Ka*(K1-Ka)*(K2-Ka)}\right] \quad \text{(Equation 3)}$$

Where:

| | | |
|---|---|---|
| D | = | intravenous dose |
| di | = | dose number (i = dose 1, 2) |
| R | = | rate of input for duration-c |
| t | = | time since intiation of the input |
| K1 | = | distribution rate constant |
| K2 | = | elimination rate constant |
| K21 | = | rate constant for transfer from peripheral compartment to central compartment |
| V | = | volume of distribution of central compartment |
| Ka | = | transdermal absortion rate constant |
| T | = | $T_{lag}$, lag time |
| Θ | = | $t$ when $t < \tau$ or $\tau$ when $t > \tau$ |

All statistical comparisons were done using analysis of variance (ANOVA). The treatment comparisons contained the following effects: subject within sequence, sequence, treatment, and period.

RESULTS

Disposition of Enrolled Subjects:

Twelve subjects enrolled in the study and eleven completed the study.

Subject Demographics:

All subjects were found to be healthy according to medical history and physical examination and clinical laboratory and electrocardiogram results.

Figure 2:
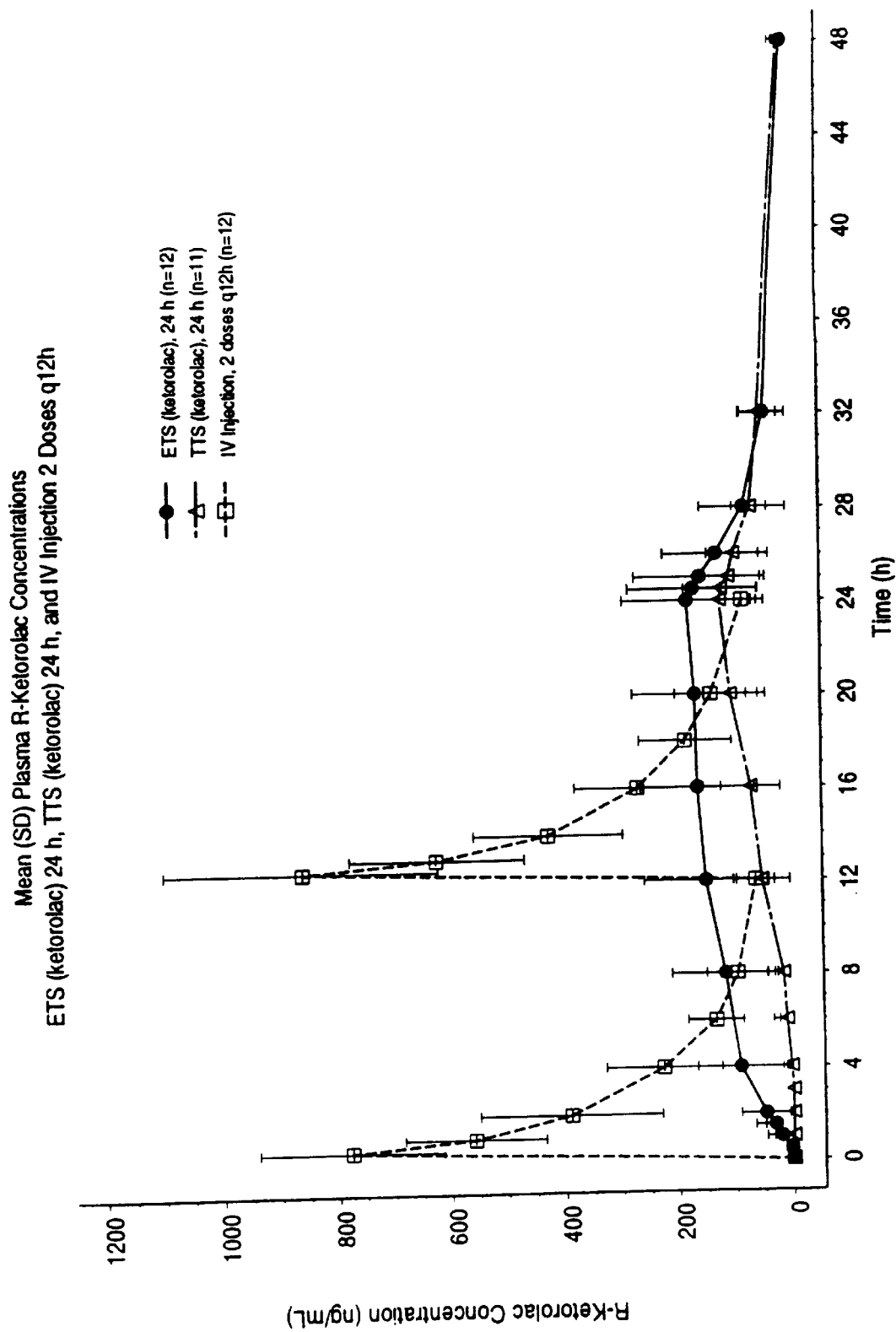
FIGS. 2 and 3 are graphs illustrating the mean plasma R- and S-ketorolac concentrations, respectively, in subjects undergoing ketorolac treatment administered via either electrotransport, passive transdermal or intravenous injection.
Figure 3:
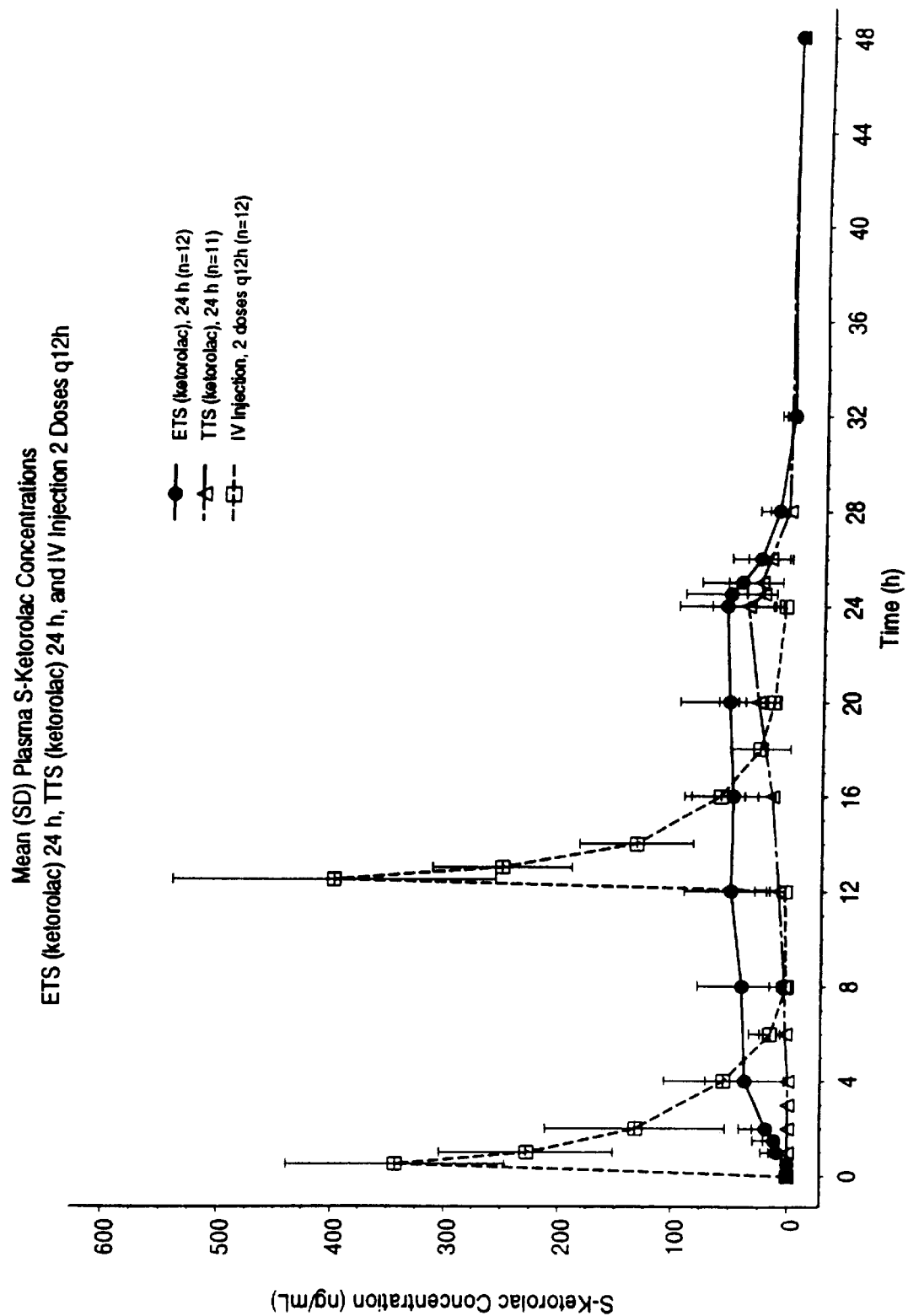

Ketorolac Pharmacokinetics:

The individual plasma concentration-time profiles following R- and S-ketorolac intravenous bolus injection and administration from ETS and TTS are presented in Tables 3 and 4. The mean (SD) plasma concentration-time profiles are shown in FIGS. 2 and 3.

Following intravenous administration of ketorolac, mean $C_{max}$ values of 872 and 404 ng/mL were observed at 0.5 hours post dose for R- and S-ketorolac, respectively. The R-ketorolac plasma concentrations during ETS and TTS administrations were not detectable until 1 hour and 4 to 8 hours post administration, respectively. The R-ketorolac plasma concentrations observed during TTS administration were lower than those observed during ETS administration. The R-ketorolac $C_{max}$ values during ETS and TTS were 195 and 132 ng/mL and the $T_{max}$ values were 22 and 23 hours, respectively. The S-ketorolac $C_{max}$ values during ETS and TTS administrations were 82 and 60 ng/mL and the $T_{max}$ values were 22 and 23 hours, respectively (Tables A, B, 3, and 4).

The mean terminal half-lives for R- and S-ketorolac were 5.0 and 2.0 hours, respectively, and the terminal rate constants were 0.14 $h^{-1}$ and 0.41 $h^{-1}$, respectively (Tables A, B, 5 and 6) following IV treatment.

Mean R-ketorolac $AUC_{inf}$ values following intravenous, ETS and TTS administrations were 6171, 4298 and 2408 ng·h/mL, respectively, and mean S-ketorolac $AUC_{inf}$ values following intravenous, ETS and TTS were 1566, 1608 and 602 ng·h/mL, respectively (Tables A, B, 7 and 8).

Following intravenous administration, R- and S-ketorolac clearance differed. The amounts of R- and S-ketorolac absorbed following ETS and TTS administrations were determined using Equation 1. Following TTS administration, the mean amounts of R- and S-ketorolac absorbed were 4.96 mg and 4.76 mg (mean total=9.72 mg), respectively (Tables A, B, 10 and 11), and were not significantly different from each other (p<0.1). Following ETS administration, the mean amounts of R- and S-ketorolac absorbed were 7.9 mg and 11.65 mg (mean total=19.55 mg), respectively (Tables A, B, 10, and 11), and were significantly different from each other (p=0.057). In this study, the target amount of total delivered R-, S-ketorolac over a 24-hour period was 24 mg. The amount absorbed following ETS treatment was close to the target value (19.59 mg), but it was considerably less than 24 mg following TTS treatment (9.72 mg).

The estimated pharmacokinetic parameters following intravenous administration of ketorolac are listed in Table 12. The mean distribution and elimination rate constants were 1.54 and 0.15 $h^{-1}$, respectively, for R-ketorolac and 2.10 and 0.35 $h^{-1}$, respectively, for S-ketorolac (Table 12).

The mean volume of distributions were 5.4 and 10.33 L for R- and S-ketorolac, respectively (Table 12). These estimated parameters were used as constants in Equation 3 and the absorption rate, $K_a$, and $T_{lag}$ were estimated following TTS administration (Table 13). The mean $K_a$ and absorption rate values were 0.61 $h^{-1}$ and 334 µg/h for R-ketorolac, and 1.7 $h^{-1}$ and 470 µg/h for S-ketorolac, respectively (Table 13).

In the case of ETS, the plasma concentration could be best fitted to a model without $T_{lag}$. The R-ketorolac mean $K_a$ and rate of absorption following ETS were 1.57 $h^{-1}$ and 392 µg/h, respectively (Table 14). For S-ketorolac, the parameters could be estimated for only 9 of 12 subjects; the $K_a$ and rate of absorption values were 0.83 $h^{-1}$ and 570 µg/h, respectively (Table 14).

TABLE 1A

Plasma R-Ketorolac Concentrations (ng/mL)
ETS (ketorolac), 24 h
(n = 12)

| Subject Number | Study Hour | | | | | | | | | | | | | | |
|---|---|---|---|---|---|---|---|---|---|---|---|---|---|---|---|
| | 0.0 | 0.5 | 1.0 | 1.5 | 2.0 | 4.0 | 8.0 | 12.0 | 16.0 | 20.0 | 24.0 | 24.5 | 25.0 | 26.0 | 28.0 |
| 101 | 0.0 | 39.0 | 79.0 | 100.0 | 140.0 | 219.0 | 245.0 | 299.0 | 308.0 | 275.0 | 279.0 | 326.0 | 313.0 | 212.0 | 154.0 |
| 102 | 0.0 | 0.0 | 0.0 | 22.0 | 30.0 | 63.0 | 74.0 | 144.0 | 140.0 | 153.0 | 161.0 | 154.0 | 156.0 | 105.0 | 46.0 |
| 103 | 0.0 | 0.0 | 0.0 | 0.0 | 0.0 | 0.0 | 20.0 | 34.0 | 34.0 | 29.0 | 31.0 | 32.0 | 27.0 | 25.0 | 0.0 |
| 104 | 0.0 | 0.0 | 0.0 | 0.0 | 38.0 | 120.0 | 115.0 | 177.0 | 219.0 | 190.0 | 200.0 | 211.0 | 176.0 | 147.0 | 91.0 |
| 105 | 0.0 | 0.0 | 37.0 | 51.0 | 69.0 | 137.0 | 215.0 | 200.0 | 220.0 | 222.0 | 267.0 | 211.0 | 173.0 | 154.0 | 92.0 |
| 106 | 0.0 | 0.0 | 0.0 | 0.0 | 0.0 | 0.0 | 0.0 | 0.0 | 29.0 | 34.0 | 35.0 | 31.0 | 28.0 | 28.0 | 0.0 |
| 107 | 0.0 | 0.0 | 0.0 | 0.0 | 0.0 | 28.0 | 0.0 | 20.0 | 31.0 | 29.0 | 65.0 | 38.0 | 30.0 | 32.0 | 0.0 |
| 108 | 0.0 | 0.0 | 25.0 | 37.0 | 50.0 | 100.0 | 122.0 | 166.0 | 172.0 | 230.0 | 210.0 | 262.0 | 204.0 | 159.0 | 129.0 |
| 109 | 0.0 | 0.0 | 45.0 | 86.0 | 99.0 | 214.0 | 259.0 | 323.0 | 295.0 | 358.0 | 383.0 | 341.0 | 386.0 | 307.0 | 237.0 |
| 110 | 0.0 | 0.0 | 0.0 | 0.0 | 27.0 | 21.0 | 36.0 | 41.0 | 78.0 | 49.0 | 79.0 | 48.0 | 48.0 | 31.0 | 0.0 |
| 111 | 0.0 | 0.0 | 39.0 | 48.0 | 84.0 | 119.0 | 171.0 | 245.0 | 217.0 | 262.0 | 297.0 | 240.0 | 211.0 | 238.0 | 132.0 |
| 112 | 0.0 | 0.0 | 24.0 | 37.0 | 43.0 | 84.0 | 151.0 | 141.0 | 205.0 | 158.0 | 138.0 | 120.0 | 115.0 | 85.0 | 63.0 |
| MEAN | 0.00 | 3.25 | 20.75 | 31.75 | 48.33 | 92.08 | 117.33 | 149.17 | 162.33 | 165.75 | 178.75 | 167.83 | 155.58 | 126.92 | 78.67 |
| SD | 0.00 | 11.26 | 25.57 | 34.94 | 43.28 | 74.82 | 93.15 | 108.50 | 99.71 | 110.64 | 113.75 | 114.29 | 115.13 | 92.83 | 75.39 |
| SE | 0.00 | 3.25 | 7.38 | 10.09 | 12.49 | 21.60 | 26.89 | 31.32 | 28.78 | 31.94 | 32.84 | 32.99 | 33.24 | 26.80 | 21.76 |

| Subject Number | Study Hour | |
|---|---|---|
| | 32.0 | 48.0 |
| 101 | 99.0 | 0.0 |
| 102 | 22.0 | 0.0 |
| 103 | 0.0 | 0.0 |
| 104 | 46.0 | 0.0 |
| 105 | 59.0 | 0.0 |
| 106 | 0.0 | 0.0 |
| 107 | 0.0 | 0.0 |
| 108 | 40.0 | 28.0 |
| 109 | 98.0 | 0.0 |
| 110 | 0.0 | 0.0 |
| 111 | 97.0 | 30.0 |
| 112 | 42.0 | 0.0 |
| MEAN | 41.92 | 4.83 |
| SD | 39.51 | 11.30 |
| SE | .41 | 3.26 |

TABLE 1B

Plasma R-Ketorolac Concentrations (ng/mL)
TTS (ketorolac), 24 h
(n = 11)

| Subject Number | Study Hour | | | | | | | | | | | | | | |
|---|---|---|---|---|---|---|---|---|---|---|---|---|---|---|---|
| | 0.0 | 1.0 | 2.0 | 3.0 | 4.0 | 6.0 | 8.0 | 12.0 | 16.0 | 20.0 | 24.0 | 24.5 | 25.0 | 26.0 | 28.0 |
| 101 | 0.0 | 0.0 | 0.0 | 0.0 | 0.0 | 0.0 | 0.0 | 0.0 | 0.0 | 26.0 | 34.0 | 38.0 | 31.0 | 29.0 | 27.0 |
| 102 | 0.0 | 0.0 | 0.0 | 0.0 | 28.0 | 56.0 | 90.0 | 174.0 | 185.0 | 239.0 | 247.0 | 227.0 | 196.0 | 164.0 | 82.0 |
| 103 | 0.0 | 0.0 | 0.0 | 0.0 | 0.0 | 0.0 | 0.0 | 40.0 | 42.0 | 53.0 | 76.0 | 75.0 | 69.0 | 70.0 | 49.0 |
| 104 | 0.0 | 0.0 | 0.0 | 0.0 | 0.0 | 0.0 | 0.0 | 0.0 | 0.0 | 57.0 | 99.0 | 47.0 | 40.0 | 57.0 | 25.0 |
| 106 | 0.0 | 0.0 | 0.0 | 0.0 | 0.0 | 0.0 | 0.0 | 26.0 | 53.0 | 87.0 | 86.0 | 144.0 | 117.0 | 102.0 | 80.0 |

TABLE 1B-continued

Plasma R-Ketorolac Concentrations (ng/mL)
TTS (ketorolac), 24 h
(n = 11)

| | | | | | | | | | | | | | | | |
|---|---|---|---|---|---|---|---|---|---|---|---|---|---|---|---|
| 107 | 0.0 | 0.0 | 0.0 | 0.0 | 0.0 | 0.0 | 0.0 | 67.0 | 52.0 | 64.0 | 50.0 | 55.0 | 43.0 | 38.0 | 36.0 |
| 108 | 0.0 | 0.0 | 0.0 | 0.0 | 0.0 | 0.0 | 24.0 | 56.0 | 71.0 | 120.0 | 166.0 | 164.0 | 153.0 | 129.0 | 79.0 |
| 109 | 0.0 | 0.0 | 0.0 | 0.0 | 0.0 | 0.0 | 26.0 | 67.0 | 115.0 | 190.0 | 203.0 | 193.0 | 170.0 | 160.0 | 123.0 |
| 110 | 0.0 | 0.0 | 0.0 | 0.0 | 0.0 | 0.0 | 0.0 | 69.0 | 76.0 | 81.0 | 126.0 | 105.0 | 125.0 | 83.0 | 62.0 |
| 111 | 0.0 | 0.0 | 0.0 | 0.0 | 0.0 | 55.0 | 32.0 | 62.0 | 81.0 | 109.0 | 148.0 | 168.0 | 144.0 | 121.0 | 95.0 |
| 112 | 0.0 | 0.0 | 0.0 | 0.0 | 0.0 | 0.0 | 0.0 | 0.0 | 85.0 | 119.0 | 100.0 | 98.0 | 75.0 | 106.0 | 76.0 |
| MEAN | 0.00 | 0.00 | 0.00 | 0.00 | 2.55 | 10.09 | 15.64 | 51.00 | 69.09 | 104.09 | 121.36 | 119.45 | 105.73 | 96.27 | 66.73 |
| SD | 0.00 | 0.00 | 0.00 | 0.00 | 8.44 | 22.45 | 27.72 | 49.66 | 51.79 | 62.80 | 64.93 | 63.72 | 57.11 | 45.59 | 30.35 |
| SE | 0.00 | 0.00 | 0.00 | 0.00 | 2.55 | 6.77 | 8.36 | 14.97 | 15.61 | 18.94 | 19.58 | 19.21 | 17.22 | 13.75 | 9.15 |

| Subject Number | Study Hour 32.0 | Study Hour 48.0 |
|---|---|---|
| 101 | 0.0 | 0.0 |
| 102 | 47.0 | 0.0 |
| 103 | 25.0 | 0.0 |
| 104 | 0.0 | 0.0 |
| 106 | 99.0 | 35.0 |
| 107 | 44.0 | 0.0 |
| 108 | 101.0 | 20.0 |
| 109 | 69.0 | 31.0 |
| 110 | 51.0 | 0.0 |
| 111 | 64.0 | 33.0 |
| 112 | 59.0 | 0.0 |
| MEAN | 50.82 | 10.82 |
| SD | 33.62 | 15.45 |
| SE | 10.14 | 4.66 |

TABLE 1C

Plasma R-Ketorolac Concentrations (ng/mL)
IV Injection, 2 Doses q12 h
(n = 12)

| Subject Number | 0.0 | 0.5 | 1.0 | 2.0 | 4.0 | 6.0 | 8.0 | 12.0 | 12.5 | 13.0 | 14.0 | 16.0 | 18.0 | 20.0 | 24.0 |
|---|---|---|---|---|---|---|---|---|---|---|---|---|---|---|---|
| 101 | 0.0 | 1162.0 | 850.0 | 844.0 | 477.0 | 224.0 | 126.0 | 82.0 | 1422.0 | 817.0 | 451.0 | 268.0 | 215.0 | 171.0 | 99.0 |
| 102 | 0.0 | 732.0 | 497.0 | 278.0 | 149.0 | 67.0 | 48.0 | 54.0 | 1040.0 | 717.0 | 403.0 | 280.0 | 111.0 | 88.0 | 38.0 |
| 103 | 0.0 | 754.0 | 521.0 | 317.0 | 190.0 | 114.0 | 73.0 | 31.0 | 635.0 | 446.0 | 318.0 | 161.0 | 92.0 | 74.0 | 50.0 |
| 104 | 0.0 | 619.0 | 455.0 | 326.0 | 195.0 | 141.0 | 92.0 | 50.0 | 696.0 | 530.0 | 367.0 | 242.0 | 174.0 | 127.0 | 81.0 |
| 105 | 0.0 | 818.0 | 517.0 | 341.0 | 196.0 | 133.0 | 135.0 | 89.0 | 823.0 | 626.0 | 439.0 | 290.0 | 233.0 | 133.0 | 85.0 |
| 106 | 0.0 | 678.0 | 520.0 | 386.0 | 266.0 | 172.0 | 103.0 | 75.0 | 753.0 | 572.0 | 386.0 | 270.0 | 178.0 | 137.0 | 96.0 |
| 107 | 0.0 | 629.0 | 419.0 | 267.0 | 102.0 | 58.0 | 34.0 | 0.0 | 685.0 | 499.0 | 344.0 | 183.0 | 112.0 | 78.0 | 44.0 |
| 108 | 0.0 | 861.0 | 600.0 | 369.0 | 186.0 | 116.0 | 54.0 | 92.0 | 898.0 | 647.0 | 386.0 | 203.0 | 139.0 | 103.0 | 51.0 |
| 109 | 0.0 | 967.0 | 706.0 | 494.0 | 331.0 | 194.0 | 234.0 | 123.0 | 1144.0 | 974.0 | 807.0 | 582.0 | 386.0 | 294.0 | 160.0 |
| 110 | 0.0 | 650.0 | 473.0 | 290.0 | 171.0 | 126.0 | 66.0 | 43.0 | 626.0 | 500.0 | 392.0 | 292.0 | 250.0 | 193.0 | 136.0 |
| 111 | 0.0 | 822.0 | 657.0 | 464.0 | 296.0 | 166.0 | 113.0 | 71.0 | 913.0 | 651.0 | 492.0 | 274.0 | 188.0 | 162.0 | 93.0 |
| 112 | 0.0 | 627.0 | 485.0 | 300.0 | 161.0 | 100.0 | 71.0 | 34.0 | 691.0 | 487.0 | 326.0 | 179.0 | 126.0 | 93.0 | 49.0 |
| MEAN | 0.00 | 776.58 | 558.33 | 389.67 | 226.67 | 134.25 | 95.75 | 62.00 | 860.50 | 622.17 | 425.92 | 268.67 | 183.67 | 137.75 | 81.83 |
| SD | 0.00 | 163.19 | 124.11 | 159.68 | 101.73 | 49.01 | 53.75 | 33.25 | 240.72 | 154.51 | 130.41 | 109.27 | 81.49 | 62.24 | 38.22 |
| SE | 0.00 | 47.11 | 35.83 | 46.09 | 29.37 | 14.15 | 15.52 | 9.60 | 69.49 | 44.60 | 37.65 | 31.54 | 23.52 | 17.97 | 11.03 |

TABLE 2A

Plasma S-Ketorolac Concentrations (ng/mL)
ETS (kotorolac), 24 h
(n = 12)

| Subject Number | Study Hour | | | | | | | | | | | | | | | |
|---|---|---|---|---|---|---|---|---|---|---|---|---|---|---|---|---|
| | 0.0 | 0.5 | 1.0 | 1.5 | 2.0 | 4.0 | 8.0 | 12.0 | 16.0 | 20.0 | 24.0 | 24.5 | 25.0 | 26.0 | 28.0 | 32.0 | 48.0 |
| 101 | 0.0 | 0.0 | 35.0 | 44.0 | 64.0 | 97.0 | 90.0 | 94.0 | 106.0 | 95.0 | 89.0 | 112.0 | 91.0 | 51.0 | 26.0 | 0.0 | 0.0 |
| 102 | 0.0 | 0.0 | 0.0 | 0.0 | 0.0 | 26.0 | 24.0 | 49.0 | 42.0 | 48.0 | 51.0 | 53.0 | 41.0 | 21.0 | 0.0 | 0.0 | 0.0 |
| 103 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 104 | 0.0 | 0.0 | 22.0 | 0.0 | 22.0 | 46.0 | 47.0 | 83.0 | 77.0 | 72.0 | 70.0 | 69.0 | 54.0 | 35.0 | 0.0 | 0.0 | 0.0 |
| 105 | 0.0 | 0.0 | 0.0 | 22.0 | 31.0 | 52.0 | 76.0 | 62.0 | 58.0 | 68.0 | 89.0 | 62.0 | 47.0 | 33.0 | 0.0 | 0.0 | 0.0 |
| 106 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 107 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 108 | 0.0 | 0.0 | 0.0 | 0.0 | 0.0 | 41.0 | 41.0 | 60.0 | 58.0 | 85.0 | 68.0 | 83.0 | 62.0 | 40.0 | 31.0 | 0.0 | 0.0 |
| 109 | 0.0 | 0.0 | 29.0 | 46.0 | 50.0 | 91.0 | 108.0 | 107.0 | 94.0 | 118.0 | 122.0 | 102.0 | 107.0 | 69.0 | 43.0 | 0.0 | 0.0 |
| 110 | 0.0 | 0.0 | 0.0 | 0.0 | 0.0 | 0.0 | 0.0 | 28.0 | 0.0 | 31.0 | 28.0 | 24.0 | 0.0 | 0.0 | 0.0 | 0.0 | 0.0 |
| 111 | 0.0 | 0.0 | 23.0 | 24.0 | 38.0 | 53.0 | 65.0 | 90.0 | 67.0 | 87.0 | 100.0 | 81.0 | 61.0 | 59.0 | 25.0 | 0.0 | 0.0 |
| 112 | 0.0 | 0.0 | 0.0 | 0.0 | 20.0 | 35.0 | 31.0 | 55.0 | 55.0 | 61.0 | 52.0 | 43.0 | 34.0 | 21.0 | 24.0 | 0.0 | 0.0 |
| MEAN | 0.00 | 0.00 | 9.08 | 11.33 | 18.75 | 36.75 | 40.17 | 50.00 | 48.75 | 52.83 | 56.00 | 52.75 | 43.42 | 27.42 | 12.42 | 0.00 | 0.00 |
| SD | 0.00 | 0.00 | 13.78 | 18.02 | 22.70 | 33.97 | 37.94 | 40.61 | 36.02 | 42.72 | 41.43 | 39.37 | 34.66 | 24.53 | 16.06 | 0.00 | 0.00 |
| SE | 0.00 | 0.00 | 3.98 | 5.20 | 6.55 | 9.81 | 10.95 | 11.72 | 10.40 | 12.33 | 11.96 | 11.37 | 10.00 | 7.08 | 4.64 | 0.00 | 0.00 |

TABLE 2B

Plasma S-Ketorolac Concentrations (ng/mL)
TTS (ketorolac), 24 h
(n = 11)

| Subject Number | Study Hour | | | | | | | | | | | | | | | |
|---|---|---|---|---|---|---|---|---|---|---|---|---|---|---|---|---|
| | 0.0 | 1.0 | 2.0 | 3.0 | 4.0 | 6.0 | 8.0 | 12.0 | 16.0 | 20.0 | 24.0 | 24.5 | 25.0 | 26.0 | 28.0 | 32.0 | 48.0 |
| 101 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 102 | 0.0 | 0.0 | 0.0 | 0.0 | 0.0 | 27.0 | 41.0 | 63.0 | 62.0 | 97.0 | 83.0 | 70.0 | 55.0 | 40.0 | 0.0 | 0.0 | 0.0 |
| 103 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 104 | 00 | 0.0 | 0.0 | 0.0 | 0.0 | 0.0 | 0.0 | 0.0 | 0.0 | 41.0 | 55.0 | 0.0 | 0.0 | 0.0 | 0.0 | 0.0 | 0.0 |
| 106 | 0.0 | 0.0 | 0.0 | 0.0 | 0.0 | 0.0 | 0.0 | 0.0 | 25.0 | 21.0 | 21.0 | 21.0 | 0.0 | 0.0 | 0.0 | 0.0 | 0.0 |
| 107 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 108 | 0.0 | 0.0 | 0.0 | 0.0 | 0.0 | 0.0 | 0.0 | 0.0 | 38.0 | 31.0 | 68.0 | 25.0 | 63.0 | 46.0 | 0.0 | 0.0 | 0.0 |
| 109 | 0.0 | 0.0 | 0.0 | 0.0 | 0.0 | 0.0 | 0.0 | 35.0 | 45.0 | 73.0 | 68.0 | 58.0 | 45.0 | 36.0 | 21.0 | 0.0 | 0.0 |
| 110 | 0.0 | 0.0 | 0.0 | 0.0 | 0.0 | 0.0 | 0.0 | 0.0 | 0.0 | 0.0 | 33.0 | 31.0 | 62.0 | 27.0 | 0.0 | 28.0 | 0.0 |
| 111 | 0.0 | 0.0 | 0.0 | 0.0 | 0.0 | 0.0 | 0.0 | 0.0 | 26.0 | 45.0 | 60.0 | 68.0 | 52.0 | 36.0 | 21.0 | 0.0 | 0.0 |
| 112 | 0.0 | 0.0 | 0.0 | 0.0 | 0.0 | 0.0 | 0.0 | 0.0 | 0.0 | 0.0 | 30.0 | 0.0 | 0.0 | 28.0 | 0.0 | 0.0 | 0.0 |
| MEAN | 0.00 | 0.00 | 0.00 | 0.00 | 0.00 | 2.45 | 3.73 | 8.91 | 15.55 | 28.36 | 38.00 | 24.82 | 27.09 | 19.36 | 3.82 | 2.55 | 0.00 |
| SD | 0.00 | 0.00 | 0.00 | 0.00 | 0.00 | 8.14 | 12.36 | 20.79 | 23.09 | 33.44 | 30.51 | 28.53 | 28.17 | 19.23 | 8.49 | 8.44 | 0.00 |
| SE | 0.00 | 0.00 | 0.00 | 0.00 | 0.00 | 2.45 | 3.73 | 6.27 | 6.96 | 10.08 | 9.20 | 8.60 | 8.49 | 5.80 | 2.56 | 2.55 | 0.00 |

TABLE 2C

Plasma S-Ketorolac Concentrations (ng/mL)
IV Injection, 2 Doses q12 h
(n = 12)

| Subject Number | Study Hour | | | | | | | | | | | | | | |
|---|---|---|---|---|---|---|---|---|---|---|---|---|---|---|---|
| | 0.0 | 0.5 | 1.0 | 2.0 | 4.0 | 6.0 | 8.0 | 12.0 | 12.5 | 13.0 | 14.0 | 16.0 | 18.0 | 20.0 | 24.0 |
| 101 | 0.0 | 595.0 | 442.0 | 364.0 | 206.0 | 53.0 | 0.0 | 0.0 | 781.0 | 330.0 | 129.0 | 51.0 | 28.0 | 0.0 | 0.0 |
| 102 | 0.0 | 317.0 | 196.0 | 80.0 | 28.0 | 0.0 | 0.0 | 0.0 | 444.0 | 248.0 | 113.0 | 44.0 | 0.0 | 0.0 | 0.0 |
| 103 | 0.0 | 324.0 | 213.0 | 99.0 | 40.0 | 0.0 | 0.0 | 0.0 | 268.0 | 182.0 | 91.0 | 33.0 | 0.0 | 0.0 | 0.0 |
| 104 | 0.0 | 284.0 | 212.0 | 126.0 | 46.0 | 24.0 | 0.0 | 0.0 | 327.0 | 226.0 | 127.0 | 60.0 | 32.0 | 0.0 | 0.0 |
| 105 | 0.0 | 365.0 | 202.0 | 104.0 | 39.0 | 0.0 | 0.0 | 0.0 | 357.0 | 251.0 | 115.0 | 62.0 | 40.0 | 0.0 | 0.0 |
| 106 | 0.0 | 264.0 | 207.0 | 125.0 | 63.0 | 26.0 | 0.0 | 0.0 | 317.0 | 206.0 | 110.0 | 57.0 | 35.0 | 21.0 | 25.0 |
| 107 | 0.0 | 249.0 | 144.0 | 75.0 | 0.0 | 0.0 | 0.0 | 0.0 | 291.0 | 200.0 | 100.0 | 36.0 | 0.0 | 0.0 | 0.0 |
| 108 | 0.0 | 400.0 | 226.0 | 107.0 | 31.0 | 0.0 | 0.0 | 45.0 | 416.0 | 257.0 | 113.0 | 35.0 | 0.0 | 0.0 | 0.0 |
| 109 | 0.0 | 387.0 | 236.0 | 150.0 | 62.0 | 29.0 | 0.0 | 0.0 | 504.0 | 376.0 | 262.0 | 132.0 | 59.0 | 34.0 | 0.0 |

TABLE 2C-continued

Plasma S-Ketorolac Concentrations (ng/mL)
IV Injection, 2 Doses q12 h
(n = 12)

| Subject Number | Study Hour | | | | | | | | | | | | | |
|---|---|---|---|---|---|---|---|---|---|---|---|---|---|---|
| | 0.0 | 0.5 | 1.0 | 2.0 | 4.0 | 6.0 | 8.0 | 12.0 | 12.5 | 13.0 | 14.0 | 16.0 | 18.0 | 20.0 | 24.0 |
| 110 | 0.0 | 285.0 | 185.0 | 91.0 | 39.0 | 23.0 | 0.0 | 0.0 | 325.0 | 238.0 | 168.0 | 110.0 | 74.0 | 49.0 | 24.0 |
| 111 | 0.0 | 388.0 | 290.0 | 182.0 | 81.0 | 32.0 | 24.0 | 0.0 | 455.0 | 314.0 | 185.0 | 64.0 | 42.0 | 72.0 | 20.0 |
| 112 | 0.0 | 256.0 | 178.0 | 85.0 | 28.0 | 0.0 | 0.0 | 0.0 | 294.0 | 181.0 | 84.0 | 27.0 | 0.0 | 0.0 | 0.0 |
| MEAN | 0.00 | 342.83 | 227.58 | 132.33 | 55.25 | 15.58 | 2.00 | 3.75 | 398.25 | 250.75 | 133.08 | 59.25 | 25.83 | 14.67 | 5.75 |
| SD | 0.00 | 96.17 | 76.12 | 79.24 | 51.76 | 17.94 | 6.93 | 12.99 | 141.87 | 61.02 | 50.03 | 31.71 | 25.84 | 24.50 | 10.46 |
| SE | 0.00 | 27.76 | 21.97 | 22.88 | 14.94 | 5.18 | 2.00 | 3.75 | 40.95 | 17.62 | 14.44 | 9.15 | 7.46 | 7.07 | 3.02 |

TABLE 3A $C_{max}$ and $T_{max}$ Values
for R-Ketorolac Concentration
ETS (ketorolac), 24 h
(n = 12)

| Subject Number | $C_{max}$ (ng/mL) | $T_{max}$ (h) |
|---|---|---|
| 101 | 326.0 | 24.5 |
| 102 | 161.0 | 24.0 |
| 103 | 34.0 | 12.0 |
| 104 | 219.0 | 16.0 |
| 105 | 267.0 | 24.0 |
| 106 | 35.0 | 24.0 |
| 107 | 65.0 | 24.0 |
| 108 | 262.0 | 24.5 |
| 109 | 386.0 | 25.0 |
| 110 | 79.0 | 24.0 |
| 111 | 297.0 | 24.0 |
| 112 | 205.0 | 16.0 |
| Mean | 194.67 | 21.83 |
| SD | 119.63 | 4.44 |
| CV | 61.45 | 20.35 |
| Gmean | 148.55 | 21.32 |
| Mean(ln) | 5.00 | 3.06 |
| SD(ln) | 0.87 | 0.24 |

TABLE 3B $C_{max}$ and $T_{max}$ Values
for R-Ketorolac Concentration
TTS (ketorolac), 24 h
(n = 11)

| Subject Number | $C_{max}$ (ng/mL) | $T_{max}$ (h) |
|---|---|---|
| 101 | 38.0 | 24.5 |
| 102 | 247.0 | 24.0 |
| 103 | 76.0 | 24.0 |
| 104 | 99.0 | 24.0 |
| 106 | 144.0 | 24.5 |
| 107 | 67.0 | 12.0 |
| 108 | 166.0 | 24.0 |
| 109 | 203.0 | 24.0 |
| 110 | 126.0 | 24.0 |
| 111 | 168.0 | 24.5 |
| 112 | 119.0 | 20.0 |
| Mean | 132.09 | 22.69 |
| SD | 61.93 | 3.76 |
| CV | 46.88 | 16.58 |
| Gmean | 117.30 | 22.30 |
| Mean(ln) | 4.76 | 3.10 |
| SD(ln) | 0.54 | 0.21 |

TABLE 3C $C_{max}$ and $T_{max}$ Values
for R-Ketorolac Concentration
IV Injection, 2 Doses q12 h
(n = 12)

| Subject Number | $C_{max}$ (ng/mL) | $T_{max}$ (h) |
|---|---|---|
| 101 | 1422.0 | 12.5 |
| 102 | 1040.0 | 12.5 |
| 103 | 754.0 | 0.5 |
| 104 | 696.0 | 12.5 |
| 105 | 823.0 | 12.5 |
| 106 | 753.0 | 12.5 |
| 107 | 685.0 | 12.5 |
| 108 | 898.0 | 12.5 |
| 109 | 1144.0 | 12.5 |
| 110 | 650.0 | 0.5 |
| 111 | 913.0 | 12.5 |
| 112 | 691.0 | 12.5 |
| Mean | 872.42 | 10.50 |
| SD | 230.72 | 4.67 |
| CV | 26.45 | 44.49 |
| Gmean | 848.26 | 7.31 |
| Mean(ln) | 6.74 | 1.99 |
| SD(ln) | 0.24 | 1.25 |

TABLE 4A $C_{max}$ and $T_{max}$ Values
for S-Ketorolac Concentration
ETS (ketorolac), 24 h
(n = 9)

| Subject Number | $C_{max}$ (ng/mL) | $T_{max}$ (h) |
|---|---|---|
| 101 | 112.0 | 24.5 |
| 102 | 53.0 | 24.5 |
| 104 | 83.0 | 12.0 |
| 105 | 89.0 | 24.0 |
| 108 | 85.0 | 20.0 |
| 109 | 122.0 | 24.0 |
| 110 | 31.0 | 24.0 |
| 111 | 100.0 | 24.0 |
| 112 | 61.0 | 20.0 |
| Mean | 81.78 | 21.89 |
| SD | 29.08 | 4.13 |
| CV | 35.56 | 18.87 |
| Gmean | 76.14 | 21.44 |
| Mean(ln) | 4.33 | 3.07 |
| SD(ln) | 0.43 | 0.23 |

NOTE: Concentrations for subjects 103, 106, 107 were zero.

TABLE 4B $C_{max}$ and $T_{max}$ Values
for S-Ketorolac Concentration
TTS (ketorolac), 24 h
(n = 8)

| Subject Number | $C_{max}$ (ng/mL) | $T_{max}$ (h) |
|---|---|---|
| 102 | 97.0 | 20.0 |
| 104 | 55.0 | 24.0 |
| 106 | 25.0 | 20.0 |
| 108 | 68.0 | 24.0 |
| 109 | 73.0 | 20.0 |
| 110 | 62.0 | 25.0 |
| 111 | 68.0 | 24.5 |
| 112 | 30.0 | 24.0 |
| Mean | 59.75 | 22.69 |
| SD | 23.36 | 2.25 |
| CV | 39.09 | 9.92 |
| Gmean | 55.00 | 22.59 |
| Mean(ln) | 4.01 | 3.12 |
| SD(ln) | 0.46 | 0.10 |

TABLE 4C $C_{max}$ and $T_{max}$ Values
for S-Ketorolac Concentration
IV Injection, 2 Doses q12 h
(n = 12)

| Subject Number | $C_{max}$ (ng/mL) | $T_{max}$ (h) |
|---|---|---|
| 101 | 781.0 | 12.5 |
| 102 | 444.0 | 12.5 |
| 103 | 324.0 | 0.5 |
| 104 | 327.0 | 12.5 |
| 105 | 365.0 | 0.5 |
| 106 | 317.0 | 12.5 |
| 107 | 291.0 | 12.5 |
| 108 | 416.0 | 12.5 |
| 109 | 504.0 | 12.5 |
| 110 | 325.0 | 12.5 |
| 111 | 455.0 | 12.5 |
| 112 | 294.0 | 12.5 |
| Mean | 403.58 | 10.50 |
| SD | 137.84 | 4.67 |
| CV | 34.15 | 44.49 |
| Gmean | 386.97 | 7.31 |
| Mean(ln) | 5.96 | 1.99 |
| SD(ln) | 0.29 | 1.25 |

TABLE 5

Apparent Elimination Rate Constant (k) and Half-Life ($t_{1/2}$) Values
for R-Ketorolac Concentration
IV Injection, 2 Doses q12 h
(n = 12)

| Subject Number | $t_{1/2}$ (h) | k ($h^{-1}$) | Time Points | n | $r^2$ |
|---|---|---|---|---|---|
| 101 | 5.5 | 0.125 | 16.00–24.00 | 4 | 1.00 |
| 102 | 3.8 | 0.183 | 18.00–24.00 | 3 | 0.98 |
| 103 | 6.9 | 0.101 | 18.00–24.00 | 3 | 1.00 |
| 104 | 5.1 | 0.136 | 16.00–24.00 | 4 | 0.99 |
| 105 | 4.3 | 0.160 | 18.00–24.00 | 3 | 0.94 |
| 106 | 5.6 | 0.125 | 16.00–24.00 | 4 | 0.96 |
| 107 | 4.0 | 0.174 | 16.00–24.00 | 4 | 0.98 |
| 108 | 4.1 | 0.171 | 16.00–24.00 | 4 | 1.00 |
| 109 | 4.4 | 0.158 | 16.00–24.00 | 4 | 0.99 |
| 110 | 7.1 | 0.098 | 16.00–24.00 | 4 | 0.99 |
| 111 | 5.3 | 0.130 | 16.00–24.00 | 4 | 0.99 |
| 112 | 4.3 | 0.161 | 16.00–24.00 | 4 | 1.00 |
| Mean | 5.02 | 0.1435 | | | |
| SD | 1.10 | 0.0285 | | | |
| CV | 21.90 | 19.8270 | | | |
| Gmean | 4.92 | 0.1408 | | | |
| Mean(ln) | 1.59 | −1.9604 | | | |
| SD(ln) | 0.21 | 0.2091 | | | |

TABLE 6

Apparent Elimination Rate Constant (k) and Half-Life ($t_{1/2}$) Values
for S-Ketorolac Concentration
IV Injection, 2 Doses q12 h
(n = 12)

| Subject Number | $t_{1/2}$ (h) | k ($h^{-1}$) | Time Points | n | $r^2$ |
|---|---|---|---|---|---|
| 101 | 1.8 | 0.382 | 14.00–18.00 | 3 | 0.98 |
| 102 | 1.2 | 0.561 | 13.00–16.00 | 3 | 0.98 |
| 103 | 1.2 | 0.560 | 13.00–16.00 | 3 | 0.99 |
| 104 | 2.0 | 0.345 | 14.00–18.00 | 3 | 1.00 |
| 105 | 2.6 | 0.264 | 14.00–18.00 | 3 | 0.99 |
| 106 | 2.8 | 0.250 | 16.00–20.00 | 3 | 1.00 |
| 107 | 1.2 | 0.563 | 13.00–16.00 | 3 | 0.99 |
| 108 | 1.1 | 0.653 | 13.00–16.00 | 3 | 0.99 |
| 109 | 2.0 | 0.349 | 13.00–20.00 | 5 | 1.00 |
| 110 | 3.6 | 0.190 | 16.00–24.00 | 4 | 1.00 |
| 111 | 3.2 | 0.220 | 13.00–24.00 | 6 | 0.81 |
| 112 | 1.1 | 0.625 | 13.00–16.00 | 3 | 0.99 |
| Mean | 1.99 | 0.4135 | | | |
| SD | 0.88 | 0.1690 | | | |
| CV | 44.15 | 40.8757 | | | |
| Gmean | 1.82 | 0.3803 | | | |
| Mean(ln) | 0.60 | −0.9667 | | | |
| SD(ln) | 0.44 | 0.4372 | | | |

TABLE 7A

AUC and $C_{avg}$ Values
for R-Ketorolac Concentration
ETS (ketorolac), 24 h
(n = 12)

| Subject Number | $AUC_t$ (ng-h/mL) | $AUC_{(0–68)}$ (ng-h/mL) | $AUC_{inf}$ (ng-h/mL) | $C_{avg}$ (ng/mL) |
|---|---|---|---|---|
| 101 | 7451.63 | 7451.63 | 8243.53 | 155.24 |
| 102 | 3177.39 | 3177.39 | 3297.53 | 66.20 |
| 103 | 586.50 | 586.50 | 833.75 | 12.22 |
| 104 | 4484.50 | 4484.50 | 4822.49 | 93.43 |
| 105 | 5430.25 | 5430.25 | 5798.90 | 113.13 |
| 106 | 381.25 | 381.25 | 605.63 | 7.94 |
| 107 | 607.75 | 607.75 | 791.24 | 12.66 |
| 108 | 5160.69 | 5160.69 | 5324.37 | 107.51 |
| 109 | 8456.77 | 8456.77 | 9076.31 | 176.18 |
| 110 | 1166.00 | 1166.00 | 1483.95 | 24.29 |
| 111 | 6994.62 | 6994.62 | 7224.87 | 145.72 |
| 112 | 3813.66 | 3813.66 | 4074.72 | 79.45 |
| Mean | 3975.917 | 3975.917 | 4298.107 | 82.832 |
| SD | 2850.239 | 2850.239 | 2976.405 | 59.380 |
| CV | 71.688 | 71.688 | 69.249 | 71.688 |
| Gmean | 2623.602 | 2623.602 | 3047.308 | 54.658 |
| Mean(ln) | 7.872 | 7.872 | 8.022 | 4.001 |
| SD(ln) | 1.113 | 1.113 | 0.981 | 1.113 |
| Max | 8456.767 | 8456.767 | 9076.311 | 176.183 |
| Min | 381.250 | 381.250 | 605.630 | 7.943 |

TABLE 7B

AUC and C $_{avg}$ Values
for R-Ketorolac Concentration
TTS (ketorolac), 24 h
(n = 11)

| Subject Number | AUC $_t$ (ng-h/mL) | AUC $_{(0-24)}$ (ng-h/mL) | AUC $_{inf}$ (ng-h/mL) | C $_{avg}$ (ng/mL) |
|---|---|---|---|---|
| 101 | 293.30 | 172.00 | 509.27 | 7.17 |
| 102 | 4218.25 | 3310.00 | 4474.90 | 137.92 |
| 103 | 1102.25 | 692.00 | 1349.50 | 28.83 |
| 104 | 614.75 | 426.00 | 798.44 | 17.75 |
| 106 | 2679.78 | 837.44 | 2960.25 | 34.89 |
| 107 | 1157.25 | 832.00 | 1409.55 | 34.67 |
| 108 | 3231.98 | 1392.00 | 3348.89 | 58.00 |
| 109 | 3793.53 | 1971.78 | 3989.51 | 82.16 |
| 110 | 1745.62 | 1155.37 | 2268.69 | 48.14 |
| 111 | 3109.50 | 1510.00 | 3362.78 | 62.92 |
| 112 | 1649.93 | 1014.76 | 2016.67 | 42.28 |
| Mean | 2145.103 | 1210.305 | 2408.042 | 50.429 |
| SD | 1328.602 | 860.038 | 1317.606 | 35.835 |
| CV | 61.936 | 0.060 | 54.717 | 71.060 |
| Gmean | 1671.989 | 949.910 | 2005.097 | 39.580 |
| Mean(ln) | 7.422 | 6.856 | 7.603 | 3.678 |
| SD(ln) | 0.831 | 0.787 | 0.694 | 0.787 |
| Max | 4218.250 | 3310.000 | 4474.904 | 137.917 |
| Min | 293.300 | 172.000 | 509.273 | 7.167 |

TABLE 7C

AUC and C $_{avg}$ Values
for R-Ketorolac Concentration
IV Injection, 2 Doses q12 h
(n = 12)

| Subject Number | AUC $_t$ (ng-h/mL) | AUC $_{(0-24)}$ (ng-h/mL) | AUC $_{inf}$ (ng-h/mL) | C $_{avg}$ (ng/mL) |
|---|---|---|---|---|
| 101 | 8126.25 | 8126.25 | 8918.15 | 338.59 |
| 102 | 4637.50 | 4637.50 | 4845.01 | 193.23 |
| 103 | 4097.00 | 4097.00 | 4591.51 | 170.71 |
| 104 | 4869.52 | 4869.52 | 5464.67 | 202.90 |
| 105 | 5726.00 | 5726.00 | 6257.10 | 238.58 |
| 106 | 5545.25 | 5545.25 | 6314.55 | 231.05 |
| 107 | 3596.00 | 3596.00 | 3848.30 | 149.83 |
| 108 | 5008.22 | 5008.22 | 5306.35 | 208.68 |
| 109 | 9436.25 | 9436.25 | 10447.75 | 393.18 |
| 110 | 5214.50 | 5214.50 | 6609.36 | 217.27 |
| 111 | 6305.32 | 6305.32 | 7019.11 | 262.72 |
| 112 | 4125.50 | 4125.50 | 4430.08 | 171.90 |
| Mean | 5557.275 | 5557.275 | 6170.994 | 231.553 |
| SD | 1705.638 | 1705.638 | 1923.591 | 71.068 |
| CV | 30.692 | 30.692 | 31.171 | 30.692 |
| Gmean | 5350.361 | 5350.361 | 5926.687 | 222.932 |
| Mean(ln) | 8.585 | 8.585 | 8.687 | 5.407 |
| SD(ln) | 0.280 | 0.280 | 0.291 | 0.280 |
| Max | 9436.250 | 9436.250 | 10447.75 | 393.177 |
| Min | 3596.000 | 3596.000 | 3848.304 | 149.833 |

TABLE 8A

AUC and C $_{avg}$ Values
for S-Ketorolac Concentration
ETS (ketorolac), 24 h
(n = 9)

| Subject Number | AUC $_t$ (ng-h/mL) | AUC $_{(8-48)}$ (ng-h/mL) | AUC $_{inf}$ (ng-h/mL) | C $_{avg}$ (ng/mL) |
|---|---|---|---|---|
| 101 | 2377.28 | 2377.28 | 2445.36 | 49.53 |
| 102 | 912.84 | 912.84 | 950.25 | 19.02 |
| 104 | 1542.50 | 1542.50 | 1644.06 | 32.14 |
| 105 | 1544.75 | 1544.75 | 1669.74 | 32.18 |
| 108 | 1431.26 | 1431.26 | 1478.71 | 29.82 |

TABLE 8A-continued

AUC and C $_{avg}$ Values
for S-Ketorolac Concentration
ETS (ketorolac), 24 h
(n = 9)

| Subject Number | AUC $_t$ (ng-h/mL) | AUC $_{(8-48)}$ (ng-h/mL) | AUC $_{inf}$ (ng-h/mL) | C $_{avg}$ (ng/mL) |
|---|---|---|---|---|
| 109 | 2632.40 | 2632.40 | 2755.45 | 54.84 |
| 110 | 201.75 | 201.75 | 327.86 | 4.20 |
| 111 | 1890.73 | 1890.73 | 2004.50 | 39.39 |
| 112 | 1157.67 | 1157.67 | 1196.09 | 24.12 |
| Mean | 1521.243 | 1521.243 | 1608.003 | 31.693 |
| SD | 737.945 | 737.945 | 744.809 | 15.374 |
| CV | 48.509 | 48.509 | 46.319 | 48.509 |
| Gmean | 1270.138 | 1270.138 | 1398.258 | 26.461 |
| Mean(ln) | 7.147 | 7.147 | 7.243 | 3.276 |
| SD(ln) | 0.764 | 0.764 | 0.636 | 0.764 |
| Max | 2632.400 | 2632.400 | 2755.452 | 54.842 |
| Min | 201.750 | 201.750 | 327.864 | 4.203 |

TABLE 8B

AUC and C $_{avg}$ Values
for S-Ketorolac Concentration
TTS (ketorolac), 24 h
(n = 8)

| Subject Number | AUC $_t$ (ng-h/mL) | AUC $_{(0-24)}$ (ng-h/mL) | AUC $_{inf}$ (ng-h/mL) | C $_{avg}$ (ng/mL) |
|---|---|---|---|---|
| 102 | 1348.00 | 1231.00 | 1419.25 | 51.29 |
| 104 | 274.00 | 274.00 | 433.60 | 11.42 |
| 106 | 163.03 | 142.38 | 247.16 | 5.93 |
| 108 | 511.83 | 412.00 | 582.24 | 17.17 |
| 109 | 902.75 | 748.00 | 962.84 | 31.17 |
| 110 | 232.75 | 66.00 | 379.88 | 2.75 |
| 111 | 567.00 | 404.00 | 662.56 | 16.83 |
| 112 | 81.00 | 59.50 | 125.82 | 2.48 |
| Mean | 510.046 | 417.110 | 601.669 | 17.380 |
| SD | 430.405 | 399.861 | 419.610 | 16.661 |
| CV | 84.386 | 95.865 | 69.741 | 95.865 |
| Gmean | 362.386 | 263.839 | 477.449 | 10.993 |
| Mean(ln) | 5.893 | 5.575 | 6.168 | 2.397 |
| SD(ln) | 0.929 | 1.093 | 0.765 | 1.093 |
| Max | 1348.000 | 1231.000 | 1419.245 | 51.292 |
| Min | 81.000 | 59.500 | 125.822 | 2.479 |

TABLE 8C

AUC and C $_{avg}$ Values
for S-Ketorolac Concentration
IV Injection, 2 Doses q12 h
(n = 12)

| Subject Number | AUC $_t$ (ng-h/mL) | AUC $_{(0-26)}$ (ng-h/mL) | AUC $_{inf}$ (ng-h/mL) | C $_{avg}$ (ng/mL) |
|---|---|---|---|---|
| 101 | 2654.50 | 2654.50 | 2727.82 | 110.60 |
| 102 | 1103.00 | 1103.00 | 1181.37 | 45.96 |
| 103 | 990.25 | 990.25 | 1049.15 | 41.26 |
| 104 | 1305.50 | 1305.50 | 1398.36 | 54.40 |
| 105 | 1271.25 | 1271.25 | 1422.76 | 52.97 |
| 106 | 1427.75 | 1427.75 | 1527.90 | 59.49 |
| 107 | 826.50 | 826.50 | 890.45 | 34.44 |
| 108 | 1295.03 | 1295.03 | 1348.60 | 53.96 |
| 109 | 2121.51 | 2121.51 | 2218.80 | 88.40 |
| 110 | 1697.75 | 1697.75 | 1823.86 | 70.74 |
| 111 | 2192.78 | 2192.78 | 2283.80 | 91.37 |
| 112 | 880.75 | 880.75 | 923.97 | 36.70 |
| Mean | 1480.548 | 1480.548 | 1566.403 | 61.689 |
| SD | 574.106 | 574.106 | 582.992 | 23.921 |
| CV | 38.777 | 38.777 | 37.219 | 38.777 |
| Gmean | 1388.048 | 1388.048 | 1474.236 | 57.835 |

TABLE 8C-continued

AUC and $C_{avg}$ Values
for S-Ketorolac Concentration
IV Injection, 2 Doses q12 h
(n = 12)

| Subject Number | $AUC_t$ (ng·h/mL) | $AUC_{(0-26)}$ (ng·h/mL) | $AUC_{inf}$ (ng·h/mL) | $C_{avg}$ (ng/mL) |
|---|---|---|---|---|
| Mean(ln) | 7.236 | 7.236 | 7.296 | 4.058 |
| SD(ln) | 0.370 | 0.370 | 0.361 | 0.370 |
| Max | 2654.500 | 2654.500 | 2727.817 | 110.604 |
| Min | 826.500 | 826.500 | 890.453 | 31.438 |

TABLE 9A

R-Ketorolac and S-Ketorolac AUC Ratios
(n = 12)

| Subject Number | ETS (ketorolac) R/S Ratio | TTS (ketorolac) R/S Ratio | IV Injection R/S Ratio |
|---|---|---|---|
| 101 | 3.37 | ... | 3.27 |
| 102 | 3.47 | 3.15 | 4.10 |
| 103 | ... | ... | 4.38 |
| 104 | 2.93 | 1.84 | 3.91 |
| 105 | 3.47 | ... | 4.40 |
| 106 | ... | 11.98 | 4.13 |
| 107 | ... | ... | 4.32 |
| 108 | 3.60 | 5.75 | 3.93 |
| 109 | 3.29 | 4.14 | 4.71 |
| 110 | 4.53 | 5.97 | 3.62 |
| 111 | 3.60 | 5.08 | 3.07 |
| 112 | 3.41 | 16.03 | 4.79 |
| Mean | 3.520 | 6.743 | 4.054 |
| SD | 0.427 | 4.805 | 0.529 |

TABLE 9A-continued

R-Ketorolac and S-Ketorolac AUC Ratios
(n = 12)

| Subject Number | ETS (ketorolac) R/S Ratio | TTS (ketorolac) R/S Ratio | IV Injection R/S Ratio |
|---|---|---|---|
| CV | 12.140 | 71.266 | 13.048 |
| SE | 0.142 | 1.699 | 0.153 |
| Min | 2.93 | 1.84 | 3.07 |
| Max | 4.53 | 16.03 | 4.79 |

TABLE 9B

R-Ketorolac and S-Ketorolac AUC Ratios
(n = 6)

| Subject Number | ETS (ketorolac) R/S Ratio | TTS (ketorolac) R/S Ratio | IV Injection R/S Ratio |
|---|---|---|---|
| 102 | 3.47 | 3.15 | 4.10 |
| 104 | 2.93 | 1.84 | 3.91 |
| 108 | 3.60 | 5.75 | 3.93 |
| 109 | 3.29 | 4.14 | 4.71 |
| 111 | 3.60 | 5.08 | 3.07 |
| 112 | 3.41 | 16.03 | 4.79 |
| Mean | 3.385 | 5.999 | 4.087 |
| SD | 0.251 | 5.105 | 0.628 |
| CV | 7.412 | 85.105 | 15.359 |
| SE | 0.102 | 2.084 | 0.256 |
| Min | 2.93 | 1.84 | 3.07 |
| Max | 3.60 | 16.03 | 4.79 |

NOTE: Table is computed for subjects with $AUC_{inf}$ for both enantiomers in all three treatments.

TABLE 10A

AUC and Amount Delivered (AD) Values
for R-Ketorolac Concentration
(n = 12)

| Subject Number | ETS (ketorolac) $AUC_{inf}$ (ng·h/mL) | TTS (ketorolac) $AUC_{inf}$ (ng·h/mL) | IV Injection $AUC_{inf}$ (ng·h/mL) | ETS/IV[a] AD (mg) | TTS/IV[b] AD (mg) |
|---|---|---|---|---|---|
| 101 | 8243.5 | 509.3 | 8918.2 | 11.09 | 0.69 |
| 102 | 3297.5 | 4474.9 | 4845.0 | 8.17 | 11.08 |
| 103 | 833.8 | 1349.5 | 4591.5 | 2.18 | 3.53 |
| 104 | 4822.5 | 798.4 | 5464.7 | 10.59 | 1.75 |
| 105 | 5798.9 | — | 6257.1 | 11.12 | — |
| 106 | 605.6 | 2960.2 | 6314.6 | 1.15 | 5.63 |
| 107 | 791.2 | 1409.6 | 3848.3 | 2.47 | 4.40 |
| 108 | 5324.4 | 3348.9 | 5306.3 | 12.04 | 7.57 |
| 109 | 9076.3 | 3989.5 | 10447.8 | 10.42 | 4.58 |
| 110 | 1483.9 | 2268.7 | 6609.4 | 2.69 | 4.12 |
| 111 | 7224.9 | 3362.8 | 7019.1 | 12.35 | 5.75 |
| 112 | 4074.7 | 2016.7 | 4430.1 | 11.04 | 5.46 |
| Mean | 4298.11 | 2408.04 | 6170.99 | 7.943 | 4.960 |
| SD | 2976.41 | 1317.61 | 1923.59 | 4.431 | 2.782 |
| CV | 69.25 | 54.72 | 31.17 | 55.779 | 56.102 |
| SE | 859.21 | 397.27 | 555.29 | 1.279 | 0.839 |
| Gmean | 3047.31 | 2005.10 | 5926.69 | 6.170 | 4.080 |
| Mean(ln) | 8.02 | 7.60 | 8.69 | 1.820 | 1.406 |
| SD(ln) | 0.98 | 0.69 | 0.29 | 0.855 | 0.750 |
| Min | 605.6 | 509.3 | 3848.3 | 1.15 | 0.69 |
| Max | 9076.3 | 4474.9 | 10447.8 | 12.35 | 11.08 |

[a]ETS/IV = $AUC_{inf}$ for ETS (ketorolac) vs $AUC_{inf}$ for IV injection.
[b]TTS/IV = $AUC_{inf}$ for TTS (ketorolac) vs $AUC_{inf}$ for IV injection.

TABLE 10B

AUC and Amount Delivered (AD) Values
for R-Ketorolac Concentration
(n = 6)

| Subject Number | ETS (ketorolac) $AUC_{inf}$ (ng · h/mL) | TTS (ketorolac) $AUC_{inf}$ (ng · h/mL) | IV Injection $AUC_{inf}$ (ng · h/mL) | ETS/IV[a] AD (mg) | TTS/IV[b] AD (mg) |
|---|---|---|---|---|---|
| 102 | 3297.5 | 4474.9 | 4845.0 | 8.17 | 11.08 |
| 104 | 4822.5 | 798.4 | 5464.7 | 10.59 | 1.75 |
| 108 | 5324.4 | 3348.9 | 5306.3 | 12.04 | 7.57 |
| 109 | 9076.3 | 3989.5 | 10447.8 | 10.42 | 4.58 |
| 111 | 7224.9 | 3362.8 | 7019.1 | 12.35 | 5.75 |
| 112 | 4074.7 | 2016.7 | 4430.1 | 11.04 | 5.46 |
| Mean | 5636.72 | 2998.53 | 6252.16 | 10.769 | 6.034 |
| SD | 2145.94 | 1358.06 | 2236.34 | 1.491 | 3.121 |
| CV | 38.07 | 45.29 | 35.77 | 13.845 | 51.724 |
| SE | 876.07 | 554.43 | 912.98 | 0.609 | 1.274 |
| Gmean | 5318.15 | 2620.37 | 5978.08 | 10.675 | 5.260 |
| Mean(ln) | 8.58 | 7.87 | 8.70 | 2.368 | 1.660 |
| SD(ln) | 0.37 | 0.64 | 0.31 | 0.148 | 0.620 |
| Min | 3297.5 | 798.4 | 4430.1 | 8.17 | 1.75 |
| Max | 9076.3 | 4474.9 | 10447.8 | 12.35 | 11.08 |

[a]ETS/IV = $AUC_{inf}$ for ETS (ketorolac) vs $AUC_{inf}$ for IV injection.
[b]TTS/IV = $AUC_{inf}$ for TTS (ketorolac) vs $AUC_{inf}$ for IV injection.

TABLE 11A

AUC and Amount Delivered (AD) Values
for S-Ketorolac Concentration
(n = 12)

| Subject Number | ETS (ketorolac) $AUC_{inf}$ (ng · h/mL) | TTS (ketorolac) $AUC_{inf}$ (ng · h/mL) | IV Injection $AUC_{inf}$ (ng · h/mL) | ETS/IV[a] AD (mg) | TTS/IV[b] AD (mg) |
|---|---|---|---|---|---|
| 101 | 2445.4 | — | 2727.8 | 10.76 | — |
| 102 | 950.2 | 1419.2 | 1181.4 | 9.65 | 14.42 |
| 103 | — | — | 1049.1 | — | — |
| 104 | 1644.1 | 433.6 | 1398.4 | 14.11 | 3.72 |
| 105 | 1669.7 | — | 1422.8 | 14.08 | — |
| 106 | — | 247.2 | 1527.9 | — | 1.94 |
| 107 | — | — | 890.5 | — | — |
| 108 | 1478.7 | 582.2 | 1348.6 | 13.16 | 5.18 |
| 109 | 2755.5 | 962.8 | 2218.8 | 14.90 | 5.21 |
| 110 | 327.9 | 379.9 | 1823.9 | 2.16 | 2.50 |
| 111 | 2004.5 | 662.6 | 2283.8 | 10.53 | 3.48 |
| 112 | 1196.1 | 125.8 | 924.0 | 15.53 | 1.63 |
| Mean | 1608.00 | 601.67 | 1566.40 | 11.654 | 4.760 |
| SD | 744.81 | 419.61 | 582.99 | 4.124 | 4.126 |
| CV | 46.32 | 69.74 | 37.22 | 35.386 | 86.676 |
| SE | 248.27 | 148.35 | 168.30 | 1.375 | 1.459 |
| Gmean | 1398.26 | 477.45 | 1474.24 | 10.404 | 3.760 |
| Mean(ln) | 7.24 | 6.17 | 7.30 | 2.342 | 1.324 |
| SD(ln) | 0.64 | 0.77 | 0.36 | 0.614 | 0.689 |
| Min | 327.9 | 125.8 | 890.5 | 2.16 | 1.63 |
| Max | 2755.5 | 1419.2 | 2727.8 | 15.53 | 14.42 |

"—": AUC incalculable
[a]ETS/IV = $AUC_{inf}$ for ETS (ketorolac) vs $AUC_{inf}$ for IV injection.
[b]TTS/IV = $AUC_{inf}$ for TTS (ketorolac) vs $AUC_{inf}$ for IV injection.

TABLE 11B

AUC and Amount Delivered (AD) Values
for S-Ketorolac Concentration
(n = 6)

| Subject Number | ETS (ketorolac) $AUC_{inf}$ (ng · h/mL) | TTS (ketorolac) $AUC_{inf}$ (ng · h/mL) | IV Injection $AUC_{inf}$ (ng · h/mL) | ETS/IV[a] AD (mg) | TTS/IV[b] AD (mg) |
|---|---|---|---|---|---|
| 102 | 950.2 | 1419.2 | 1181.4 | 9.65 | 14.42 |
| 104 | 1644.1 | 433.6 | 1398.4 | 14.11 | 3.72 |
| 108 | 1478.7 | 582.2 | 1348.6 | 13.16 | 5.18 |
| 109 | 2755.5 | 962.8 | 2218.8 | 14.90 | 5.21 |
| 111 | 2004.5 | 662.6 | 2283.8 | 10.53 | 3.48 |
| 112 | 1196.1 | 125.8 | 924.0 | 15.53 | 1.63 |
| Mean | 1671.51 | 697.72 | 1559.15 | 12.981 | 5.607 |
| SD | 643.43 | 447.73 | 561.54 | 2.391 | 4.512 |
| CV | 38.49 | 64.17 | 36.02 | 18.420 | 80.479 |
| SE | 262.68 | 182.78 | 229.25 | 0.976 | 1.842 |
| Gmean | 1574.95 | 553.52 | 1478.16 | 12.786 | 4.494 |
| Mean(ln) | 7.36 | 6.32 | 7.30 | 2.548 | 1.503 |
| SD(ln) | 0.38 | 0.83 | 0.36 | 0.194 | 0.711 |
| Min | 950.2 | 125.8 | 924.0 | 9.65 | 1.63 |
| Max | 2755.5 | 1419.2 | 2283.8 | 15.53 | 14.42 |

[a]ETS/IV = $AUC_{inf}$ for ETS (ketorolac) vs $AUC_{inf}$ for IV injection.
[b]TTS/IV = $AUC_{inf}$ for TTS (ketorolac) vs $AUC_{inf}$ for IV injection.

TABLE 12

Pharmacokinetic Parameters Following Administration of IV Injection
Compartmental Analysis
(n = 12)

| | R-Ketorolac | | | | S-Ketorolac | | | |
|---|---|---|---|---|---|---|---|---|
| Subject Number | Volume (L) | K1 ($h^{-1}$) | K2 ($h^{-1}$) | K21 ($h^{-1}$) | Volume (L) | K1 ($h^{-1}$) | K2 ($h^{-1}$) | K21 ($h^{-1}$) |
| 101 | 0.970 | 5.814 | 0.297 | 1.336 | 1.235 | 5.889 | 0.420 | 1.062 |
| 102 | 4.788 | 0.907 | 0.063 | 0.164 | 9.586 | 1.072 | 0.049 | 0.076 |
| 103 | 4.829 | 2.372 | 0.287 | 1.208 | 12.454 | 1.947 | 0.603 | 1.483 |
| 104 | 6.923 | 1.051 | 0.135 | 0.477 | 13.240 | 1.494 | 0.404 | 1.034 |
| 105 | 4.971 | 1.313 | 0.131 | 0.493 | 9.379 | 1.655 | 0.388 | 0.803 |
| 106 | 5.850 | 1.627 | 0.177 | 0.879 | 14.862 | 0.847 | 0.159 | 0.284 |
| 107 | 7.116 | 0.676 | 0.049 | 0.108 | 7.172 | 5.415 | 0.769 | 2.769 |
| 108 | 4.775 | 1.043 | 0.182 | 0.424 | 7.083 | 2.734 | 0.671 | 1.688 |
| 109 | 5.156 | 0.570 | 0.067 | 0.225 | 10.448 | 0.678 | 0.043 | 0.096 |
| 110 | 7.943 | 0.673 | 0.045 | 0.179 | 14.778 | 0.785 | 0.025 | 0.098 |
| 111 | 4.995 | 1.468 | 0.202 | 0.856 | 10.623 | 0.713 | 0.067 | 0.123 |
| 112 | 6.729 | 0.950 | 0.161 | 0.408 | 13.162 | 1.996 | 0.643 | 1.535 |
| MEAN | 5.4204 | 1.5386 | 0.1497 | 0.5630 | 10.3353 | 2.1020 | 0.3534 | 0.9210 |
| SD | 1.7791 | 1.4364 | 0.0860 | 0.4137 | 3.8860 | 1.7747 | 0.2771 | 0.8450 |
| CV | 32.8229 | 93.3557 | 57.4578 | 73.4884 | 37.5995 | 84.4298 | 78.4052 | 91.7490 |
| SE | 0.5136 | 0.4146 | 0.0248 | 0.1194 | 1.1218 | 0.5123 | 0.0800 | 0.2439 |
| Max | 7.943 | 5.814 | 0.297 | 1.336 | 14.862 | 5.889 | 0.769 | 2.769 |
| Min | 0.970 | 0.570 | 0.045 | 0.108 | 1.235 | 0.678 | 0.025 | 0.076 |

TABLE 13

Rate of Absorption Following Administration of ETS (ketorolac)
Compartmental Analysis
(n = 12)

| | R-Ketorolac | | S-Ketorolac | |
|---|---|---|---|---|
| Subject Number[a] | Ka ($h^{-1}$) | Rate (µg/h) | Ka ($h^{-1}$) | Rate (µg/h) |
| 101 | 2.864 | 745.87 | 1.626 | 876.62 |
| 102 | 0.892 | 337.91 | 0.537 | 358.79 |
| 103 | 0.722 | 66.62 | — | — |
| 104 | 0.843 | 455.22 | 0.901 | 568.18 |
| 105 | 2.691 | 534.76 | 1.313 | 568.72 |
| 106 | 0.243 | 57.17 | — | — |

TABLE 13-continued

Rate of Absorption Following Administration of ETS (ketorolac)
Compartmental Analysis
(n = 12)

| Subject Number[a] | R-Ketorolac | | S-Ketorolac | |
|---|---|---|---|---|
| | Ka (h$^{-1}$) | Rate (μg/h) | Ka (h$^{-1}$) | Rate (μg/h) |
| 107 | 0.835 | 76.68 | — | — |
| 108 | 0.695 | 489.14 | 0.351 | 559.18 |
| 109 | 0.837 | 856.01 | 1.008 | 963.00 |
| 110 | 2.093 | 126.00 | 0.174 | 126.01 |
| 111 | 0.877 | 600.20 | 0.856 | 695.26 |
| 112 | 5.292 | 359.57 | 0.655 | 407.17 |
| Mean | 1.5737 | 392.096 | 0.8245 | 569.214 |
| SD | 1.4413 | 271.333 | 0.4583 | 258.002 |
| CV | 91.5881 | 69.201 | 55.5873 | 45.326 |
| SE | 0.4161 | 78.327 | 0.1528 | 86.001 |
| Max | 5.292 | 856.01 | 1.626 | 963.00 |
| Min | 0.243 | 57.17 | 0.174 | 126.01 |

[a]Subjects 103, 106 and 107: Ka not estimable for S-ketorolac.

TABLE 14

Rate of Absorption Following Administration of TTS (ketorolac)
Compartmental Analysis
(n = 9)

| Subject Number[a] | R-Ketorolac | | | S-Ketorolac | | |
|---|---|---|---|---|---|---|
| | Ka (h$^{-1}$) | T$_{lag}$ (h) | Rate (μg/h) | Ka (h$^{-1}$) | T$_{lag}$ (h) | Rate (μg/h) |
| 101 | 0.842 | 15.6 | 111.89 | — | — | — |
| 102 | 2.309 | 4.9 | 545.78 | 1.865 | 5.0 | 637.72 |
| 103 | 0.361 | 7.2 | 177.57 | — | — | — |
| 106 | 0.087 | 7.1 | 394.18 | 3.912 | 15.8 | 211.16 |
| 108 | 0.182 | 6.3 | 388.33 | 0.688 | 11.9 | 433.09 |
| 109 | 0.541 | 9.1 | 490.71 | 1.289 | 9.8 | 541.09 |
| 110 | 0.570 | 7.3 | 272.22 | — | — | — |
| 111 | 0.169 | 2.7 | 338.16 | 0.743 | 13.9 | 528.90 |
| 112 | 0.449 | 10.2 | 287.08 | — | — | — |
| Mean | 0.6122 | 7.83 | 333.991 | 1.6995 | 11.31 | 470.391 |
| SD | 0.6789 | 3.64 | 139.561 | 1.3257 | 4.19 | 162.029 |
| CV | 110.8859 | 46.50 | 41.786 | 78.0049 | 37.06 | 34.446 |
| SE | 0.2263 | 1.21 | 46.520 | 0.5929 | 1.87 | 72.461 |
| Max | 2.309 | 15.6 | 545.78 | 3.912 | 15.8 | 637.72 |
| Min | 0.087 | 2.7 | 111.89 | 0.688 | 5.0 | 211.16 |

[a]Subjects 101, 103 and 112: Ka not estimable for S-ketorolac.
Subjects 104 and 107: Ka not estimable for both R- and S-ketorolac.
Subject 105 discontinued study before TTS treatment.
Subject 110: Concentrations of S-ketorolac were observed only after patch removal.

What is claimed is:

1. A method for preferentially delivering through a body surface a preferred isomer of a drug from a formulation containing the drug as a racemic mixture of said preferred isomer and a less preferred isomer, comprising;

(a) applying to an area of the body surface the formulation containing the drug as a racemic mixture of isomers; and (b) delivering the drug by electrotransport through said area simultaneously with or subsequent to step (a), in a manner effective to enhance the transport of said preferred isomer from the racemic mixture relative to the transport of said less preferred isomer from the racemic mixture.

2. A method for preferentially delivering through a body surface a preferred isomer of a drug from a formulation containing the drug as a racemic mixture of said preferred isomer and a less preferred isomer, comprising;

(a) placing a drug reservoir in a drug-transmitting relation with an area of the body surface, the reservoir comprising the formulation containing the drug as a racemic mixture of isomers;

(b) electrically connecting the drug reservoir to a source of electrical power; and (c) delivering the drug through the skin by means of electrotransport, wherein said preferred isomer is delivered from the racemic mixture at a first rate which is sufficient to induce a therapeutic effect, and said less preferred isomer is delivered from the racemic mixture at a second rate which is lower than said first rate.

3. The method of claim 1, wherein the body surface is skin.

4. The method of claim 3, wherein the source of electrical power provides a skin current density of about 50 to 625 μA/cm$^2$.

5. The method of claim 4, wherein the source of electrical power provides a skin current density of about 100 μA/cm$^2$.

6. The method of claim 1, wherein the formulation further comprises a permeation enhancer present in an amount effective to decrease the electrical resistance of the body surface to the drug and thereby enhance the rate of penetration of the drug therethrough during electrotransport drug delivery.

7. The method of claim 1, wherein the drug is selected from the group consisting of acebutolol, acenocoumarol, albuterol/salbutamol, alprenolol, amosulolol, amoxicillin, ampicillin, Ansaid, astemizole, atenolol, baclofen, benazepril, benzyl glutamate, betaxolol, bethanecol, bisprolol, bopindolol, bucumolol, bufetolol, bufuralol, bunitrolol, bupranolol, butaclamol, butoconazole, butofilolol, calcitonin, camazepam, captopril, captopril, caraxolol, carvedilol, cefadroxil, cicloprofen, ciprofloxacin, corticosteroids, cromakalim, curteolol, cytrabine, deprenyl, dexfenfluramine, dihydroxythebaine, diltiazem, disopyramide, dobutamine, enalapril, ephedrine, estradiol, ethambutol, fenbuphen, fenfluramine, fenoprofen, fluorogesterone, fluoxetine, flurbiprofen, gonadorelin, hexobarbital, ibuprofen, imovane, indenolol, indoprofen, ketamine, ketodesogestrel/estrogen, ketoprofen, ketorolac, lisinopril, lorazepam, lovastatin, meclizine, mepindolol, metaproteranol, methadone, methyldopa, metipranolol, metoprolol, minoxiprofen, 3-hydroxy-N-methyl morphinan, nadolol, naproxen, nebivolol, nicardipine, nicotine, nilvadipine, nitanol, norfloxacin, norgestrel, ofloxacin, Orudis, oxaprotiline, oxpranolol, oxybutynin, perindopril, phenprocoumon, phenylpropanolamine, pindolol, pirprofen, polycloranphetamine, prilocaine, progestinpropanolol, propoxyphene, sertraline, sotalol, steroids, suprofen, tenormin, terbutaline, terfenadine, testosterone, thioridazine, timolol, tocainide, toliprolol, toloxaton, tomoxetine, triamcinolone, verapamil, viloxazin, warfarin, xibenolol, zacopride, and 1,4-dihydropyridine chiral compounds, and pharmaceutically acceptable salts and esters thereof.

8. The method of claim 1, wherein the drug is an antiinflammatory.

9. The method of claim 8, wherein the antiinflammatory is an NSAID.

10. The method of claim 9, wherein the drug is ketorolac or a pharmacologically acceptable salt or ester thereof.

11. The method of claim 10, wherein the preferred enantiomer is the S-isomer.

12. The method of claim 11, wherein the drug is ketorolac tromethamine.

13. A method for preferentially delivering through a body surface a preferred isomer of a drug, comprising:

(a) identifying a preferred isomer and a less preferred isomer of the drug;

(b) applying to an area of the body surface a formulation containing the drug as a racemic mixture of the isomers; and (c) preferentially delivering from the racemic mixture said preferred isomer relative to said less preferred isomer via electrotransport through said area.

14. A method of improved electrotransport delivery of a drug that exists as a racemic mixture of isomers, comprising:

(a) identifying a preferred isomer and a less preferred isomer for the drug;

(b) increasing the relative proportion of the preferred isomer of the drug in the racemic mixture of isomers of the drug to provide a mixture enhanced for the preferred isomer;

(c) placing the enhanced mixture of drug in a drug reservoir;

(d) placing the drug reservoir in drug-transmitting relation to an intact area of skin; and (e) preferentially delivering from the enhanced racemic mixture said preferred isomer relative to said less preferred isomer via electrotransport.

15. The method of claim 1, wherein the current used during electrotransport is less than that necessary to provide therapeutically effective levels of the drug if the preferred and less preferred isomers were deliverable via electrotransport at the same rate.

16. The method of claim 1, wherein the amount of the formulation applied is less than that necessary to provide therapeutically effective levels of the drug if the preferred and less preferred isomers were deliverable via electrotransport at the same rate.

17. The method of claim 1, wherein the concentration of drug used in the formulation is less than that necessary to provide therapeutically effective levels of the drug if the preferred and less preferred isomers were deliverable via electrotransport at the same rate.

18. The method of claim 1, wherein the formulation is provided in the form of a patch of a size less than that necessary to provide therapeutically effective levels of the drug if the preferred and less preferred isomers were deliverable via electrotransport at the same rate.

19. A method for preferentially delivering through a body surface a preferred isomer of a drug from a formulation containing the drug as a racemic mixture of said preferred isomer and a less preferred isomer, comprising:

(a) determining the relative fluxes from the racemic mixture of the isomers of said drug through said body surface;

(b) determining the relative bioactivities of the isomers of the racemic mixture of said drug;

(c) selecting a preferred isomer based on the determined fluxes and relative bioactivities; and (d) delivering the drug by electrotransport so that therapeutically effective levels of the preferred isomer are delivered through the body surface from the racemic mixture.

20. A method of preferentially lowering the amount delivered through a body surface of a less preferred isomer of a drug from a formulation containing the drug as a racemic mixture of a preferred isomer and said less preferred isomer, comprising:

(a) applying to an area of the body surface the formulation containing the drug as a racemic mixture of the isomers; and (b) delivering the drug by electrotransport through said area simultaneously with or subsequent to step (a), in a manner effective to decrease the transport from the racemic mixture of the less preferred isomer relative to the transport of the preferred isomer from the racemic mixture.

21. The method of claim 20, wherein said less preferred isomer is toxic.

22. The method of claim 20, wherein said less preferred isomer is a mutagen.

* * * * *

UNITED STATES PATENT AND TRADEMARK OFFICE
CERTIFICATE OF CORRECTION

PATENT NO.    : 6,136,327
DATED         : October 24, 2000
INVENTOR(S)   : Suneel K. Gupta et al.

It is certified that error appears in the above-identified patent and that said Letters Patent is hereby corrected as shown below:

Columns 1 through 36, should be deleted, and substitute therefor columns 1 through 34, as shown on the attached pages.

Signed and Sealed this

Thirteenth Day of July, 2004

JON W. DUDAS
*Acting Director of the United States Patent and Trademark Office*

STEREOSPECIFIC DELIVERY OF A DRUG USING ELECTROTRANSPORT

TECHNICAL FIELD

This invention relates generally to drug delivery. More particularly, the invention relates to the use of electrotransport to effect stereospecific drug delivery, i.e., preferential delivery of a single preferred enantiomer of a chiral drug from a pharmaceutical formulation containing the drug as a mixture of isomers.

BACKGROUND

A number of drugs contain chiral centers and thus can exist in two or more isomeric forms. A drug with a single chiral center can be formed as two "mirror-image" isomers, known as "enantiomers." In many instances, the enantiomers exhibit differences in pharmacokinetic properties, e.g., metabolism, protein binding, or the like, and/or pharmacological properties, e.g., the type of activity displayed, the degree of activity, toxicity, or the like. Isolation of a single enantiomer from a mixture, i.e., "resolution" of the mixture, is typically carried out by reaction with a standard asymmetric substance, followed by separation of the different products using conventional means. Fractional crystallization is another technique which may be employed to isolate a single enantiomer.

Frequently, however, isolation of a single enantiomer from a mixture is difficult, as the two enantiomers within the mixture are by definition identical in terms of molecular composition and thus, in many instances, are substantially similar in reactivity. Alternatively, a single enantiomer of a drug or other compound may be prepared using a stereospecific synthesis which gives rise to the product in enantiomerically pure form. Such syntheses are typically somewhat difficult to implement and often do not provide the desired product in high yield.

Recent reports detail the lengths undertaken in order to obtain purified isomers of useful drugs. For example, U.S. Pat. No. 5,545,745 to Gao et al. claims a multistep process for preparing optically pure albuterol, employing reaction of a mixture of albuterol isomers with a chiral acid and selective crystallization of one of the products, followed by debenzylation to yield optically pure albuterol. U.S. Pat. No. 5,442,118 to Gao et al. claims a method of asymmetric synthesis of (R) and (S) arylethanolamines from aminoketones, useful for the preparation of pharmaceutical agents such as albuterol, terbutaline, isoproterenol and sotalol, using a borane reducing agent in the presence of a chiral 1,3,2-oxazaborolidine catalyst, wherein the reagents must be added in a specific order. U.S. Pat. No. 5,516,943 to Gao et al. describes the stereoselective conversion of a trans-1-amino-2-hydroxycycloalkane to the cis isomer by acylating the amine group and then treating with a strong acid; also disclosed is the direct formation of particular isomers of aminoindanol from indene using exotic chiral catalysts. U.S. Pat. No. 5,498,625 to Evans et al. describes the enzymatic production of one enantiomer of a lactam by reacting a racemic γ lactam with a stereospecific lactamase. U.S. Pat. No. 4,800,162 to Matson claims a method of resolving a racemic mixture by passing a solution containing the mixture through a filtering device having a stereoselective enzyme attached to the filter matrix on a first side: the enzyme selectively reacts with one isomer, creating a product which is then more soluble in an immiscible solvent flowing in the opposite direction on the opposite side of the matrix; the product then diffuses across the matrix, yielding a pure solution of enantiomeric product on the opposite side and producing a pure solution of the unreacted enantiomer on the first side.

As can be seen, elaborate efforts have been made in order to produce purified isomers of pharmacologically active agents.

With chiral drugs, if one enantiomer is pharmacologically more active, less toxic, or has a preferred disposition in the body as compared with the other enantiomer, it would be therapeutically more beneficial to administer that enantiomer preferentially. In this way, the patient undergoing treatment would be exposed to a lower total dose of the drug, or to a lower amount of a toxic isomer. Costly and complicated stereospecific synthesis or purification schemes would then be unnecessary.

Accordingly, there is a need in the art for a means of drug administration which enables preferential delivery of a single enantiomer of a chiral drug.

International Patent Publication No. WO 94/10985 describes the benefits provided by transdermal delivery of the active enantiomer of ketorolac compared to delivery of the racemic mixture. The active enantiomer was found to have a more rapid clearance than the other enantiomer, so that the continuous delivery provided by a transdermal system allowed for even lower dosages to be used than expected. That is, whereas one might expect that half of the total amount of the pure enantiomer would be as effective as the full dose of the racemic mixture, even less than half the amount of the pure enantiomer was found to be effective. This was attributed to the more rapid clearance and shorter half-life of the active enantiomer. Continuous delivery using the passive transdermal system provided a more steady level of the minimum therapeutic amount of the active enantiomer as compared with periodic dosing of the racemic mixture by immediate release oral or parenteral administration. Passive transdermal delivery was claimed to be beneficial for all enantiomers with high clearance values and short half-lives. Problems with passive transdermal drug delivery systems were also discussed, including the limits on the doses capable of being provided because of the limited permeability of the stratum corneum layer of the skin and the unacceptability of large patches to patients because of contact-related side effects, aesthetics, comfort and wearability.

The melting temperature of a drug is believed to be one factor limiting the ability of that drug to permeate the skin. Lawter and Pawelchak (U.S. Pat. No. 5,114,946) claimed that, for a chiral drug that is a solid at or above skin temperature, purified enantiomers or nonracemic mixtures of the drug display faster passive transdermal delivery rates when the purified enantiomers or the nonracemic mixtures have melting temperatures 5°–10° C. below that of the racemic mixture. However, no increase in the flux rate of one isomer relative to the other isomer in a mixture was noted.

Sanderson (U.S. Pat. No. 4,818,541) similarly reported that the purified individual isomers of phenylpropanolamine gave rise to faster transdermal penetration rates compared to the racemic mixture. The mechanism by which this occurred was not stated with certainty, but the increased solubility of the individual isomers compared to the mixture was suggested as one possibility. Each of the four individual purified isomers exhibited nearly identical flux rates.

The inventors herein have now found that passive transdermal drug delivery of a composition containing a drug (ketorolac) in the form of a racemic mixture does not provide for any significant difference in flux between the two isomers. This is consistent with previous reports that (−) ketorolac and racemic ketorolac have similar flux characteristics when used in several different types of passive transdermal systems (U.S. Pat. No. 5,589,498 to Mohr et al.). (−) Ketorolac is the active enantiomer of ketorolac, a non-steroidal anti-inflammatory analgesic which can produce gastrointestinal side effects when delivered orally. Transdermal patches of the adhesive matrix type, reservoir type, and monolithic matrix type were all reported to deliver similar flux rates of (−) ketorolac and racemic ketorolac.

Unexpectedly, electrotransport drug delivery has been discovered to give rise to a substantial differential in the rate of transport of two enantiomers contained in a mixture. Prior to applicants' invention, it was believed that the capability of administering a drug using electrotransport was solely a function of the drug's physico-chemical properties; now, it is clear that electrotransport drug delivery can be stereospecific as well.

In contrast to passive transdermal or transmucosal systems, electrotransport has been found to provide for the preferential delivery of one isomer from a mixture while providing a faster overall flux rate than passive delivery systems, and requires no special synthetic or purification schemes. Additionally, preferential isomer delivery via electrotransport is not limited to particular mixtures of drug isomers that have a lower melting temperature than the racemic mixture, or to enantiomers with high clearance values and low half-lives. As a result of the increased transfer rate, electrotransport can permit a shorter time of delivery or the use of a smaller, more acceptable coverage area in order to deliver the desired amount of compound than such passive delivery systems. Generally, it is preferred that at least a 20% increase in the rate of in vivo delivery of the preferred isomer is achieved. However, a smaller increase in rate of delivery, of about 5 or 10%, may prove acceptable in some cases, for example where the drug is particularly expensive.

By eliminating the need for stereospecific synthesis or complicated purification procedures, selective delivery of one isomer via electrotransport can lead to improvements in therapeutic costs and treatment regimens. Costs of synthesis can be decreased by eliminating the need for stereospecific synthesis or purification of one isomer from a mixture. A simpler scheme for synthesis and purification can result in a lowered generation of hazardous materials and a lessened exposure of personnel to those materials. Additionally, stereoselective electrotransport can be used to preferentially deliver one isomer where stereospecific synthesis or purification of that isomer has not yet been achieved. By receiving an increased amount of the preferred isomer, patients can thus be exposed to a lesser total amount of compound or be treated for a shorter time or over a smaller region of their body.

Furthermore, even if passive drug delivery could give rise to differences in flux rates of desired isomers, electrotransport can increase this differential while providing higher overall flux rates than passive systems, allowing for smaller, more acceptable delivery devices. Similarly, where chemical synthesis or purification schemes provide a greater proportion of the desired enantiomer in a mixture, electrotransport delivery of the mixture can further increase the proportion of desired enantiomer which is delivered.

Herein the term "electrotransport drug delivery" is used to refer to the delivery of pharmaceutically active agents through an area of the body surface by means of an electromotive force to a drug-containing reservoir. The drug may be delivered by electromigration, electroporation, electroosmosis or any combination thereof. Electroosmosis has also been referred to as electrohydrokinesis, electro-convection, and electrically induced osmosis. In general, electroosmosis of a species into a tissue results from the migration of solvent in which the species is contained, as a result of the application of electromotive force to the therapeutic species reservoir, i.e., solvent flow induced by electromigration of other ionic species. During the electrotransport process, certain modifications or alterations of the skin may occur such as the formation of transiently existing pores in the skin, also referred to as "electroporation." Any electrically assisted transport of species enhanced by modifications or alterations to the body surface (e.g., formation of pores in the skin) are also included in the term "electrotransport" as used herein. Thus, as used herein, the term "electrotransport" refers to (1) the delivery of charged drugs or agents by electromigration, (2) the delivery of uncharged drugs or agents by the process of electroosmosis, (3) the delivery of charged or uncharged drugs by electroporation, (4) the delivery of charged drugs or agents by the combined processes of electromigration and electroosmosis, and/or (5) the delivery of a mixture of charged and uncharged drugs or agents by the combined processes of electromigration and electroosmosis.

SUMMARY OF THE INVENTION

The invention thus provides a method for using electrotransport drug delivery to preferentially deliver a preferred isomer from a pharmaceutical formulation containing the drug as a mixture of preferred and less preferred isomers. The method involves (a) applying to an area of the body surface a formulation containing the drug as a mixture of isomers, and (b) delivering the formulation by electrotransport through the same area of the body surface simultaneously with or subsequent to step (a), so that the transport of a preferred isomer is enhanced relative to the transport of a less preferred isomer. Generally, the method will involve: placing an electrotransport drug reservoir in drug-transmitting relation to the selected area of the body surface, the reservoir containing the aforementioned formulation; electrically connecting the drug reservoir to a source of electrical power; and then delivering the drug through the body surface by electrotransport. As explained above, the process is carried out such that the preferred enantiomer is delivered at a rate sufficient to induce a therapeutic effect, while the corresponding, second enantiomer is delivered at a substantially lower rate. A method of decreasing the delivery via electrotransport of a less preferred isomer of a drug is also provided. Drug delivery devices suitable for such preferential delivery and methods of making the same are also provided.

BRIEF DESCRIPTION OF THE DRAWINGS

FIG. 1 is a perspective view of an electrotransport drug delivery device which may be used in conjunction with the present invention.

FIGS. 2 and 3 are graphs illustrating the mean plasma R- and S-ketorolac concentrations, respectively, in subjects undergoing ketorolac treatment administered via either electrotransport, passive transdermal or intravenous injection.

DETAILED DESCRIPTION OF THE INVENTION

It is to be understood that this invention is not limited to specific pharmaceutical compositions, carriers, drug delivery device structures, or the like, as such may vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. Thus, reference to "a drug" includes mixtures of drugs, reference to "an enhancer" includes mixtures of enhancers, reference to "a carrier" includes mixtures of carriers, and the like.

In describing and claiming the present invention, the following terminology will be used in accordance with the definitions set out below.

The terms "drug," "active agent" or "pharmacologically active agent" are used interchangeably herein to mean any chemical material or compound which induces a desired local or systemic effect in an individual subject (human or animal), and is capable of being delivered to the subject by electrotransport.

By the term "dosage" is meant the amount of drug delivered from an electrotransport delivery device. The term is intended to encompass the amount of drug delivered per unit time, the total amount of drug delivered over a period of time, the duration of time over which the drug is to be delivered, and the like.

The term "optional" as used herein, as in the recitation that the presence of a particular component in a pharmaceutical composition is "optional," means that the component may or may not be present, and includes instances where the component is present and instances where the component is not present.

Drugs, therapeutics or otherwise active agents useful in connection with the present invention include any pharmaceutical compound that is capable of being delivered by electrotransport, wherein the compound exists in the form of an isomeric mixture, and further wherein it is desired to preferentially deliver a preferred isomer from those in the mixture, or wherein it is desired to preferentially not deliver a less preferred isomer. This includes drugs with one, two, or more chiral centers, having two, four, or more isomers, wherein one, two, or more of the isomers are preferred, and/or one, two, or more of the isomers are less preferred. The active agents which may be administered using the methodology of the invention includes agents in all of the major therapeutic areas. For example, suitable active agents include, but are not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary anticholinergics, sympathomimetics, xanthine derivatives, calcium channel blockers, beta-blockers, beta-agonists, antiarrhythmics, antihypertensives, ACE inhibitors, diuretics, vasodilators, central nervous system stimulants, cough and cold preparations, decongestants, diagnostics, hormones such as parathyroid hormone, bisphosphoriates, hypnotics, immunosuppressives, muscle relaxants, parasympatholytics, parasympathomimetics, prostaglandins, psychostimulants, sedatives and tranquilizers. The invention is also useful in conjunction with the electrotransport delivery of proteins, peptides and fragments thereof.

A particularly preferred drug which can be administered using the methodology of the invention is the anti-inflammatory, analgesic agent ketorolac (±)-benzoyl-2,3-dihydro-1H-pyrrolizine-1-carboxylic acid)), as the S-isomer of the drug has been found to be significantly more active than the R-isomer. It has been established that the S:R ratios of anti-inflammatory and analgesic activities are 57 and 230, respectively (Mroszczak et al. (1994) *Clin. Pharm Ther.* 42:126; Hayball et al. (1993) *Chirality* 5:31–35). Therefore, it is advantageous to deliver the single S-isomer preferentially.

Other enantiomeric drugs where preferential isomeric delivery is desirable include ibuprofen (the S-isomer is the active ingredient), terfenadine (the S-isomer is active), nicotine (the S (−) isomer has been found less irritating in transdermal patch formulations), nebivolol (the (+) isomer is a β-blocker, while the (−) isomer is a vasodilating agent), zacopride (one isomer is a 5-HT$_3$ blocker, the other is an agonist), tenormin (the S-isomer is a β-blocker), imovane (the S-isomer is a sedative), Ansaid (the S-isomer is a nonsteroidal antiinflammatory drug, or "NSAID"), and Orudis (the S-isomer is an NSAID).

Further nonlimiting examples of drugs which are available as racemates but wherein one isomer would be preferred for delivery include acebutolol, acenocoumarol, albuterol/salbutamol, alprenolol, amosulolol, amoxicillin, ampicillin, astemizole, atenolol, baclofen, benazepril, benzyl glutamate, betaxolol, bethanecol, bisprolol, bopindolol, bucumolol, bufetolol, bufuralol, bunitrolol, bupranolol, butaclamol, butoconazole, butofilolol, calcitonin, camazepam, captopril, captopril, caraxolol, carvedilol, cefadroxil, cicloprofen, ciprofloxacin, corticosteroids, cromakalim, curteolol, cytrabine, deprenyl, dexfenfluramine, dihydroxythebaine, diltiazem, disopyramide, dobutamine, enalapril, ephedrine, estradiol, ethambutol, fenbuphen, fenfluramine, fenoprofen, fluorogesterone, fluoxetine, flurbiprofen, gonadorelin, hexobarbital, ibuprofen, indenolol, indoprofen, ketamine, ketodesogestrel/estrogen, ketoprofen, lisinopril, lorazepam, lovastatin, meclizine, mepindolol, metaproteranol, methadone, methyldopa, metipranolol, metoprolol, minoxiprofen, 3-hydroxy-N-methyl morphinan, nadolol, naproxen, nicardipine, nilvadipine, nitanol, norfloxacin, norgestrel, ofloxacin, oxaprotiline, oxpranolol, oxybutynin, perindopril, phenprocoumon, phenylpropanolamine, pindolol, pirprofen, polycloram-phetamine, prilocaine, progestinpropanolol, propoxyphene, sertraline, sotalol, steroids, suprofen, terbutaline, terfenadine, testosterone, thioridazine, timolol, tocainide, toliprolol, toloxaton, tomoxetine, triamcinolone, verapamil, viloxazin, warfarin, xibenolol, and 1,4-dihydropyridine chiral compounds.

The compounds may be in the form of pharmaceutically acceptable salts, esters, amides or prodrugs, or may be modified by appending one or more appropriate functionalities to enhance selected biological properties. Such modifications are known in the art and include those which increase biological penetration into a given biological system, increase bioavailability, increase solubility to allow administration by a particular mode, and the like.

Compounds may be converted into pharmaceutically acceptable salts, and the salts may be converted into the free compound using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

Acid addition salts are prepared from the free base (e.g., compounds having a neutral—NH$_2$ or cyclic amine group)

using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preferred acid addition salts of the present compounds are the citrate, fumarate, succinate, benzoate and malonate salts.

Basic salts of acid moieties which may be present (e.g., carboxylic acid groups) can be prepared in a similar manner using pharmaceutically acceptable inorganic or organic bases. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, trimethylamine, triethylamine, benzylamine, dibenzylamine or α- or β-phenylethylamine, and heterocyclic bases such as piperidine, 1-methylpiperidine and morpholine.

Compounds may also be converted into pharmaceutically acceptable esters. Suitable esters include branched or unbranched, saturated or unsaturated $C_1$ to $C_6$ alkyl esters, for example, methyl, ethyl and vinyl esters.

Preparation of esters involves functionalization of hydroxyl and/or carboxyl groups which may be present. Esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures. Preparation of amides and prodrugs can be performed in an analogous manner.

Electrotransport devices which can be employed in the method of the present invention typically comprise at least two electrodes. Each of these electrodes is placed in intimate electrical contact with some portion of the skin of the body. One electrode, called the active or donor electrode, is the electrode from which the drug is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device. If the drug to be driven into the body is positively charged, then the positive electrode (the anode) will be the active electrode and the negative electrode (the cathode) will serve as the counter electrode, completing the circuit. If the drug to be delivered is negatively charged, then the cathodic electrode will be the active electrode and the anodic electrode will be the counter electrode.

Electrotransport devices additionally require a drug reservoir or source of the pharmaceutically active agent which is to be delivered or introduced into the body. Such drug reservoirs are connected to the anode or the cathode of the electrotransport device to provide a fixed or renewable source of one or more desired species or agents. The drug reservoirs are usually polymeric hydrogels. Suitable polymers useful for forming hydrogel drug reservoirs include: polyvinyl alcohols; polyvinyl-pyrrolidone; cellulosic polymers, e.g., hydroxyethyl cellulose, hydroxypropyl cellulose, hydroxypropyl methylcellulose, carboxymethyl cellulose, and the like; polyurethanes; polyethylene oxides; polyanhydrides; polyvinyl pyrrolidone/vinyl acetate copolymers, and the like; and mixtures and copolymers thereof. One material suitable for electrotransport drug reservoirs is polyvinyl alcohol, which has been found to have good skin biocompatibility.

The drug reservoirs may contain a number of components, such as preservatives, solubilizing agents, pH modifiers, antimicrobials, antifungals, anti-inflammatory agents, stabilizers, surfactants, and the like. The drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, dimethylsulfoxide (DMSO), dimethyl formamide (DMF), N,N-dimethylacetamide (DMA), decylmethylsulfoxide ($C_{10}MSO$), $C_2$–$C_6$ alkanediols, and the 1-substituted azacycloheptan-2-ones, particularly 1-n-dodecylcyclazacycloheptan-2-one (available under the trademark Azone® from Whitby Research Incorporated, Richmond, Va.), alcohols, and the like.

It will be appreciated by those working in the field that the present method can be used in conjunction with a wide variety of electrotransport drug delivery systems, as the method is not limited in any way in this regard. For examples of electrotransport drug delivery systems, reference may be had to U.S. Pat. Nos. 5,147,296 to Theeuwes et al., U.S. Pat. No. 5,080,646 to Theeuwes et al., U.S. Pat. No. 5,169,382 to Theeuwes et al., and U.S. Pat. No. 5,169,383 to Gyory et al., the disclosures of which are incorporated by reference herein.

FIG. 1 illustrates a representative electrotransport delivery device that may be used in conjunction with the present method. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and drug/ chemical reservoirs 26,28, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrode/reservoirs 22,26 and 24,28 for a delivery interval of predetermined length. The push button switch 12 is conveniently located on the top side of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, e.g., a "beeper". Drug is delivered through the patient's skin by electrotransport, e.g., on the arm, over the predetermined delivery interval.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained by lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

The reservoirs 26 and 28 comprise a gel matrix, with at least one of the reservoirs comprised of the hydrogel formulation of the invention. Drug concentrations in the range of approximately $1\times10^{-4}$ M to 1.0 M or more can be used, with drug concentrations in the lower portion of the range being preferred. Concentrations lower than about $1\times10^{-4}$ M may also be effective, particularly with peptide or protein drugs. Generally it is preferred that the drug concentration not become so low during drug delivery that flux becomes dependent on drug concentration, but remains dependent on current. For an expensive drug, however, this may not be possible. Factors which affect the ultimate device formulation include device size, drug solubility, drug cost, and dosing regimen.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

The transport of the R- and S-isomers of ketorolac was evaluated using passive transdermal delivery and electrotransport, in a study conducted in healthy volunteers. Intravenous bolus administration of 24 mg racemic ketorolac served as the reference treatment. The relative amounts of R- and S-ketorolac absorbed following passive transdermal and electrotransport administration were determined relative to intravenous R- and S-ketorolac clearance (assuming that the racemic ketorolac contained equal amounts of the R- and S-isomers). The mean amounts of R- and S-ketorolac absorbed following passive transdermal administration were 5.0 mg and 4.8 mg (mean total=9.8 mg) respectively, and, following electrotransport administration, were 7.9 and 11.7 mg (mean total=19.6 mg) respectively. Following passive transdermal administration, the amount of R-ketorolac absorbed was similar to that of S-ketorolac ($p>0.5$). However, following electrotransport administration the mean amount of R-ketorolac absorbed was found to be lower than that of S-ketorolac absorbed. The S/R ratio of amount absorbed ranged from 0.8 to 1.43 (mean, 1.15; median, 1.18).

EXAMPLE 2

Drugs comprising mixtures of enantiomers are evaluated to determine a preferred isomer. Purified isomers as well as mixtures of isomers are delivered to test subjects and the efficacy, pharmacokinetics and pharmacodynamic profile of the isomers are determined. Preferred isomers are identified as those that are effective and exhibit some beneficial feature as compared to a mixture of isomers, for example improved therapeutic index, improved activity, improved half-life, lower effective dosage, lower toxicity, fewer or lessened side effects, or the ability to be delivered via electrotransport to an effective therapeutic level in an acceptable patch size, and the like.

EXAMPLE 3

A mixture of isomeric forms of a drug is incorporated into an electrotransport device. The device is applied to test subjects, and blood samples are subsequently taken from the subjects at various time intervals before, during and after treatment. Plasma concentrations of the preferred isomer and the other isomers are determined. Drugs for which electrotransport provides increased uptake of the preferred isomer are identified. Generally, it is preferred that at least a 20% increase in the rate of in vivo delivery of the preferred isomer is achieved. However, a smaller increase in rate of delivery, of about 5 or 10%, may prove acceptable in some cases, for example where the drug is particularly expensive.

EXAMPLE 4

A study was performed in order to compare the pharmacokinetic parameters of R- and S-ketorolac following intravenous, passive transdermal and electrotransport administration of a racemic mixture of ketorolac.

Screening Procedures

Twelve healthy male volunteers were enrolled in a pilot feasibility study. Subjects were required to undergo a pre-study screening to evaluate whether they met study inclusion or exclusion criteria. Screening procedures included a medical history, physical exam, electrocardiogram and clinical laboratory tests.

Materials and Methods

Study Design:

The study was an open-label, randomized, three-treatment crossover pharmacokinetics study designed to compare plasma ketorolac concentrations during 24-hour treatment regimens with an electrotransport system ("ETS"), a (passive) therapeutic transdermal system ("TTS") and intravenous ketorolac bolus injection.

Treatment Overview and Randomization:

The ketorolac treatments are listed below; there was a washout period of at least 6 days between treatments.

| | |
|---|---|
| ETS (ketorolac): | Ketorolac delivered with electrotransport from a total cathode area of 18 cm$^2$, at a current density of 100 µA/cm$^2$, for 24 hours |
| TTS (ketorolac): | Ketorolac delivered passively through the skin from three systems, total area 75 cm$^2$, for 24 hours |
| Intravenous ketorolac: | Intravenous bolus injection of ketorolac, 12 mg of free acid (18 mg of ketorolac tromethamine salt), at Hour 0 and Hour 12 (a total of 24 mg). |

Subjects were assigned randomly to receive the three ketorolac treatments in one of the following randomization schemes:

| Sequence | Subject Number |
|---|---|
| ETS, TTS, Bolus | 103, 106, 107, 110 |
| TTS, Bolus, ETS | 101, 104, 108, 112 |
| Bolus, ETS, TTS | 102, 105, 109, 111 |

ETS Treatment:

During the ETS (ketorolac) treatment, each subject was expected to receive an estimated 26 mg of ketorolac free acid over a 24-hour period, delivered by electrotransport from a total cathode area of 18 cm$^2$, based on an estimated in vitro flux rate of 60 µg/cm$^2$/h.

ETS System Description:

The ALZA Model 6443 Electrical Current Source ("ECS"), in combination with the Electrotransport Delivery Platform containing the active drug gel at the cathode and the pharmacologically inactive gel at the anode, makes up the electrotransport drug delivery system.

The Model 6443 ECS is a reusable electrical current regulator (controller). The controller was set in the direct current ("DC") mode to provide continuous electrical current for the delivery of ketorolac during ETS treatment.

The electrotransport delivery platform consisted of a housing containing the anode and cathode electrodes and two gel reservoirs. The cathode reservoir was designed to hold the active gel imbibed with ketorolac and was 6 cm$^2$. The anode reservoir comprised a pharmacologically inactive gel and was 6 cm$^2$. The inactive anode gels were placed against the anode electrode during manufacture and assembly of the housing. The drug-imbibed cathode gels were inserted into the platform just prior to use. A pressure sensitive adhesive permitted application of the system to the skin. The delivery platform was connected to the ECS by a cable.

Three electrotransport systems, with a total cathode gel area of 18 cm$^2$, were applied to the upper arms of each subject in this study. Each of the three controllers was set to provide a total direct current of 0.6 mA, which maintained a current density of 100 µA/cm$^2$.

A current and voltage check of the controller were performed using a voltmeter at hours 0, 2, 4, 8, 12 and 24 of the ETS application.

If the voltage exceeded 15 volts or the current was not within ±20% of target value, the controller was adjusted. If adjustment did not correct the problem, the controller was replaced and the subject continued in the study.

TTS Treatment:

During TTS treatment, each subject was expected to receive an estimated 50 mg of ketorolac free acid over a 24-hour period, delivered passively through the skin from a total application area of 75 cm$^2$ based on an estimated in vitro flux rate of 25 to 30 µg/cm$^2$/h.

TTS System Description:

The TTS systems were produced with a backing and protective liner in a 25 cm$^2$ size. The system formulation contained drug (free acid), ethylene vinyl acetate (40% vinyl acetate), glycerol monolaurate, and Ceraphyl® 31. Three TTS monoliths, with a total surface area of 75 cm$^2$, were used to deliver the drug. The combined systems contained 135 mg of ketorolac free acid. Because the systems were not self-adhesive, an adhesive overlay was required to ensure good skin contact.

Intravenous Ketorolac Bolus Injection Treatment:

During the intravenous bolus treatment, each subject received a total of 24 mg of ketorolac free acid (36 mg of ketorolac tromethamine salt). Drug was delivered by IV bolus injections of 12 mg of ketorolac free acid (18 mg of ketorolac tromethamine salt) which were administered at Hour 0 and at Hour 12. A 1 mL aliquot of each ketorolac solution was retained directly after syringe preparation and prior to injection.

Treatment Schedule:

Initially either the ETS or the TTS was applied, or the first intravenous injection was administered. ETS and TTS treatments continued for 24 hours, and the bolus treatment was completed after the second dose at 12 hours. Blood and urine samples were collected at intervals during a 48-hour period after initiation of each ketorolac treatment regimen.

After completion of all three drug treatments and blood and urine collection phases, a post-study physical examination, electrocardiogram, and clinical laboratory tests were performed.

Blood Sampling for Pharmacokinetics Assessment:

Blood samples, 7 mL each, were collected from each subject at intervals during the 48 hour period after initiation of treatment.

Plasma levels of ketorolac were determined by HPLC assay, performed at the Clinical Pharmacology Division of the School of Medicine at Indiana University, Wishard Memorial Hospital, Indianapolis, Ind.

Topical Evaluations:

Skin site assessments were conducted at intervals at both the anode and the cathode sites of the electrotransport system and at the sites to which the TTS (ketorolac) systems were applied.

Pharmacokinetics Methods:

Actual blood sample collection times were used for all calculations and data were summarized by nominal sampling times. Plasma ketorolac concentrations below the assay quantification limit of 20 ng/mL were assigned a value of zero.

The maximal observed plasma concentrations ($C_{max}$) of R- and S-ketorolac and the corresponding sampling times ($T_{max}$), expressed in hours, were determined over the entire sampling interval following TTS and ETS treatment.

The apparent elimination rate constants (k) for both R- and S-ketorolac were estimated by linear regression of log-transformed plasma concentrations during the terminal log-linear decline phase following intravenous administration. Apparent half-life ($t_{1/2}$) values were calculated as 0.693/k.

The area under the plasma R- and S-ketorolac concentration time profiles, from Hour 0 to the last detectable concentration at time t ($AUC_t$), were determined by the linear trapezoidal method. The AUC value extrapolated to infinity ($AUC_{inf}$) was determined as the sum of $AUC_t$ and the area extrapolated to infinity, and was calculated by the concentration at time t ($C_t$) divided by k. The average steady-state drug concentrations ($C_{avg}$) were calculated as $AUC_{inf}/24$.

The R- and S-ketorolac $AUC_{inf}$ ratio was determined for all three treatments. The amounts of R- and S-ketorolac absorbed following the ETS (ketorolac) and TTS (ketorolac) treatments were calculated using the estimated intravenous clearance ($Dose/AUC_{inf}$) as given in Equation 1, which assumed no interconversion between the enantiomers:

$$\text{Amount absorbed} = AUC_{inf(TTS/ETS)} * CL_{IV} \quad \text{(Equation 1)}$$

The disposition of R- and S-ketorolac following intravenous administration could be best described by a two-compartment open model. The pharmacokinetics parameters following intravenous administration of R- and S-ketorolac were estimated by non-linear regression of the plasma concentration-time profile (Equation 2). The rate of drug input and the absorption rate constant following both ETS (ketorolac) and TTS (ketorolac) administration were then estimated by fitting the respective plasma concentration-time profile to Equation 3. The pharmacokinetics parameters such as V, K1, K2, and K21 estimated from intravenous data were used as constants.

$$C(t) = \frac{D}{V*(K1-K2)} * \left[ \frac{(K21-K1)*(1-\exp^{(di*K1*\tau)})*(\exp^{(-K1*t)})}{(1-\exp^{(K1*\tau)})} + \frac{(K21-K2)*(1-\exp^{(di*K2*\tau)})*(\exp^{(-K2*t)})}{(1-\exp^{(K2*\tau)})} \right] \quad \text{(Equation 2)}$$

$$C(t) = \frac{R*K_a}{V} * \left[ \frac{(1-\exp^{(K1*\theta)})*(\exp^{(-K1*(t-T))})*(K21-K1)}{K1*(K1-K2)*(Ka-K1)} + \frac{(1-\exp^{(K2*\theta)})*(\exp^{(-K2*(t-T))})*(K21-K2)}{K2*(K1-K2)*(Ka-K2)} - \right. \quad \text{(Equation 3)}$$

$$\left. \frac{(1-\exp^{(Ka*\theta)})*(\exp^{(-Ka*(t-T))})*(K21-Ka)}{Ka*(K1-Ka)*(K2-Ka)} \right]$$

Where:
- D = intravenous dose
- di = dose number (i = dose 1, 2)
- R = rate of input for duration -τ
- t = time since initiation of the input
- K1 = distribution rate constant
- K2 = elimination rate constant
- K21 = rate constant for transfer from peripheral compartment to central compartment
- V = volume of distribution of central compartment
- Ka = transdermal absorption rate constant
- T = $T_{lag}$, lag time
- θ = t when t < τ or τ when t > τ

All statistical comparisons were done using analysis of variance (ANOVA). The treatment comparisons contained the following effects: subject within sequence, sequence, treatment, and period.

Results

Disposition of Enrolled Subjects:

Twelve subjects enrolled in the study and eleven completed the study.

Subject Demographics:

All subjects were found to be healthy according to medical history and physical examination and clinical laboratory and electrocardiogram results.

Ketorolac Pharmacokinetics:

The individual plasma concentration-time profiles following R- and S-ketorolac intravenous bolus injection and administration from ETS and TTS are presented in Tables 3 and 4. The mean (SD) plasma concentration-time profiles are shown in FIGS. 2 and 3.

Following intravenous administration of ketorolac, mean $C_{max}$ values of 872 and 404 ng/mL were observed at 0.5 hours post dose for R- and S-ketorolac, respectively. The R-ketorolac plasma concentrations during ETS and TTS administrations were not detectable until 1 hour and 4 to 8 hours post administration, respectively. The R-ketorolac plasma concentrations observed during TTS administration were lower than those observed during ETS administration. The R-ketorolac $C_{max}$ values during ETS and TTS were 195 and 132 ng/mL and the $T_{max}$ values were 22 and 23 hours, respectively. The S-ketorolac $C_{max}$ values during ETS and TTS administrations were 82 and 60 ng/mL and the $T_{max}$ values were 22 and 23 hours, respectively (Tables A, B, 3, and 4).

The mean terminal half-lives for R- and S-ketorolac were 5.0 and 2.0 hours, respectively, and the terminal rate constants were 0.14 $h^{-1}$ and 0.41 $h^{-1}$, respectively (Tables A, B, 5 and 6) following IV treatment.

Mean R-ketorolac $AUC_{inf}$ values following intravenous, ETS and TTS administrations were 6171, 4298 and 2408 ng·h/mL, respectively, and mean S-ketorolac $AUC_{inf}$ values following intravenous, ETS and TTS were 1566, 1608 and 602 ng·h/mL, respectively (Tables A, B, 7 and 8).

Following intravenous administration, R- and S-ketorolac clearance differed. The amounts of R- and S-ketorolac absorbed following ETS and TTS administrations were determined using Equation 1. Following TTS administration, the mean amounts of R- and S-ketorolac absorbed were 4.96 mg and 4.76 mg (mean total=9.72 mg), respectively (Tables A, B, 10 and 11), and were not significantly different from each other (p<0.1). Following ETS administration, the mean amounts of R- and S-ketorolac absorbed were 7.9 mg and 11.65 mg (mean total=19.55 mg), respectively (Tables A, B, 10, and 11), and were significantly different from each other (p=0.057). In this study, the target amount of total delivered R-, S-ketorolac over a 24-hour period was 24 mg. The amount absorbed following ETS treatment was close to the target value (19.59 mg), but it was considerably less than 24 mg following TTS treatment (9.72 mg).

The estimated pharmacokinetic parameters following intravenous administration of ketorolac are listed in Table 12. The mean distribution and elimination rate constants were 1.54 and 0.15 $h^{-1}$, respectively, for R-ketorolac and 2.10 and 0.35 $h^{-1}$, respectively, for S-ketorolac (Table 12). The mean volume of distributions were 5.4 and 10.33 L for R- and S-ketorolac, respectively (Table 12). These estimated parameters were used as constants in Equation 3 and the absorption rate, $K_a$, and $T_{lag}$ were estimated following TTS administration (Table 13). The mean $K_a$ and absorption rate values were 0.61 $h^{-1}$ and 334 µg/h for R-ketorolac, and 1.7 $h^{-1}$ and 470 µg/h for S-ketorolac, respectively (Table 13).

In the case of ETS, the plasma concentration could be best fitted to a model without $T_{lag}$. The R-ketorolac mean $K_a$ and rate of absorption following ETS were 1.57 $h^{-1}$ and 392 µg/h, respectively (Table 14). For S-ketorolac, the parameters could be estimated for only 9 of 12 subjects; the $K_a$ and rate of absorption values were 0.83 $h^{-1}$ and 570 µg/h, respectively (Table 14).

TABLE 1A

Plasma R-Ketorolac Concentrations (ng/mL)
ETS (ketorolac), 24 h
(n = 12)

| Subject Number | Study Hour | | | | | | | | | | | | | | | | |
|---|---|---|---|---|---|---|---|---|---|---|---|---|---|---|---|---|---|
| | 0.0 | 0.5 | 1.0 | 1.5 | 2.0 | 4.0 | 8.0 | 12.0 | 16.0 | 20.0 | 24.0 | 24.5 | 25.0 | 26.0 | 28.0 | 32.0 | 48.0 |
| 101 | 0.0 | 39.0 | 79.0 | 100.0 | 140.0 | 219.0 | 245.0 | 299.0 | 308.0 | 275.0 | 279.0 | 326.0 | 313.0 | 212.0 | 154.0 | 99.0 | 0.0 |
| 102 | 0.0 | 0.0 | 0.0 | 22.0 | 30.0 | 63.0 | 74.0 | 144.0 | 140.0 | 153.0 | 161.0 | 154.0 | 156.0 | 105.0 | 46.0 | 22.0 | 0.0 |
| 103 | 0.0 | 0.0 | 0.0 | 0.0 | 0.0 | 0.0 | 20.0 | 34.0 | 34.0 | 29.0 | 31.0 | 32.0 | 27.0 | 25.0 | 0.0 | 0.0 | 0.0 |
| 104 | 0.0 | 0.0 | 0.0 | 0.0 | 38.0 | 120.0 | 115.0 | 177.0 | 219.0 | 190.0 | 200.0 | 211.0 | 176.0 | 147.0 | 91.0 | 46.0 | 0.0 |
| 105 | 0.0 | 0.0 | 37.0 | 51.0 | 69.0 | 137.0 | 215.0 | 200.0 | 220.0 | 222.0 | 267.0 | 211.0 | 173.0 | 154.0 | 92.0 | 59.0 | 0.0 |
| 106 | 0.0 | 0.0 | 0.0 | 0.0 | 0.0 | 0.0 | 0.0 | 0.0 | 29.0 | 34.0 | 35.0 | 31.0 | 28.0 | 28.0 | 0.0 | 0.0 | 0.0 |
| 107 | 0.0 | 0.0 | 0.0 | 0.0 | 0.0 | 28.0 | 0.0 | 20.0 | 31.0 | 29.0 | 65.0 | 38.0 | 30.0 | 32.0 | 0.0 | 0.0 | 0.0 |
| 108 | 0.0 | 0.0 | 25.0 | 37.0 | 50.0 | 100.0 | 122.0 | 166.0 | 172.0 | 230.0 | 210.0 | 262.0 | 204.0 | 159.0 | 129.0 | 40.0 | 28.0 |
| 109 | 0.0 | 0.0 | 45.0 | 86.0 | 99.0 | 214.0 | 259.0 | 323.0 | 295.0 | 358.0 | 383.0 | 341.0 | 386.0 | 307.0 | 237.0 | 98.0 | 0.0 |
| 110 | 0.0 | 0.0 | 0.0 | 0.0 | 27.0 | 21.0 | 0.0 | 41.0 | 36.0 | 78.0 | 49.0 | 79.0 | 48.0 | 48.0 | 31.0 | 0.0 | 0.0 |
| 111 | 0.0 | 0.0 | 39.0 | 48.0 | 84.0 | 119.0 | 171.0 | 245.0 | 217.0 | 262.0 | 297.0 | 240.0 | 211.0 | 238.0 | 132.0 | 97.0 | 30.0 |
| 112 | 0.0 | 0.0 | 24.0 | 37.0 | 43.0 | 84.0 | 151.0 | 141.0 | 205.0 | 158.0 | 138.0 | 120.0 | 115.0 | 85.0 | 63.0 | 42.0 | 0.0 |
| MEAN | 0.00 | 3.25 | 20.75 | 31.75 | 48.33 | 92.08 | 117.33 | 149.17 | 162.33 | 165.75 | 178.75 | 167.83 | 155.58 | 126.92 | 78.67 | 41.92 | 4.83 |
| SD | 0.00 | 11.26 | 25.57 | 34.94 | 43.28 | 74.82 | 93.15 | 108.50 | 99.71 | 110.64 | 113.75 | 114.29 | 115.13 | 92.83 | 75.39 | 39.51 | 11.30 |
| SE | 0.00 | 3.25 | 7.38 | 10.09 | 12.49 | 21.60 | 26.89 | 31.32 | 28.78 | 31.94 | 32.84 | 32.99 | 33.24 | 26.80 | 21.76 | 11.41 | 3.26 |

TABLE 1B

Plasma R-Ketorolac Concentrations (ng/mL)
TTS (ketorolac), 24 h
(n = 11)

| Subject Number | Study Hour | | | | | | | | | | | | | | | | |
|---|---|---|---|---|---|---|---|---|---|---|---|---|---|---|---|---|---|
| | 0.0 | 1.0 | 2.0 | 3.0 | 4.0 | 6.0 | 8.0 | 12.0 | 16.0 | 20.0 | 24.0 | 24.5 | 25.0 | 26.0 | 28.0 | 32.0 | 48.0 |
| 101 | 0.0 | 0.0 | 0.0 | 0.0 | 0.0 | 0.0 | 0.0 | 0.0 | 0.0 | 26.0 | 34.0 | 38.0 | 31.0 | 29.0 | 27.0 | 0.0 | 0.0 |
| 102 | 0.0 | 0.0 | 0.0 | 0.0 | 28.0 | 56.0 | 90.0 | 174.0 | 185.0 | 239.0 | 247.0 | 227.0 | 196.0 | 164.0 | 82.0 | 47.0 | 0.0 |
| 103 | 0.0 | 0.0 | 0.0 | 0.0 | 0.0 | 0.0 | 0.0 | 40.0 | 42.0 | 53.0 | 76.0 | 75.0 | 69.0 | 70.0 | 49.0 | 25.0 | 0.0 |
| 104 | 0.0 | 0.0 | 0.0 | 0.0 | 0.0 | 0.0 | 0.0 | 0.0 | 0.0 | 57.0 | 99.0 | 47.0 | 40.0 | 57.0 | 25.0 | 0.0 | 0.0 |
| 106 | 0.0 | 0.0 | 0.0 | 0.0 | 0.0 | 0.0 | 0.0 | 26.0 | 53.0 | 87.0 | 86.0 | 144.0 | 117.0 | 102.0 | 80.0 | 99.0 | 35.0 |
| 107 | 0.0 | 0.0 | 0.0 | 0.0 | 0.0 | 0.0 | 0.0 | 67.0 | 52.0 | 64.0 | 50.0 | 55.0 | 43.0 | 38.0 | 36.0 | 44.0 | 0.0 |
| 108 | 0.0 | 0.0 | 0.0 | 0.0 | 0.0 | 0.0 | 24.0 | 56.0 | 71.0 | 120.0 | 166.0 | 164.0 | 153.0 | 129.0 | 79.0 | 101.0 | 20.0 |
| 109 | 0.0 | 0.0 | 0.0 | 0.0 | 0.0 | 0.0 | 26.0 | 67.0 | 115.0 | 190.0 | 203.0 | 193.0 | 170.0 | 160.0 | 123.0 | 69.0 | 31.0 |
| 110 | 0.0 | 0.0 | 0.0 | 0.0 | 0.0 | 0.0 | 0.0 | 69.0 | 76.0 | 81.0 | 126.0 | 105.0 | 125.0 | 83.0 | 62.0 | 51.0 | 0.0 |
| 111 | 0.0 | 0.0 | 0.0 | 0.0 | 0.0 | 55.0 | 32.0 | 62.0 | 81.0 | 109.0 | 148.0 | 168.0 | 144.0 | 121.0 | 95.0 | 64.0 | 33.0 |
| 112 | 0.0 | 0.0 | 0.0 | 0.0 | 0.0 | 0.0 | 0.0 | 0.0 | 85.0 | 119.0 | 100.0 | 98.0 | 75.0 | 106.0 | 76.0 | 59.0 | 0.0 |
| MEAN | 0.00 | 0.00 | 0.00 | 0.00 | 2.55 | 10.09 | 15.64 | 51.00 | 69.09 | 104.09 | 121.36 | 119.45 | 105.73 | 96.27 | 66.73 | 50.82 | 10.82 |
| SD | 0.00 | 0.00 | 0.00 | 0.00 | 8.44 | 22.45 | 27.72 | 49.66 | 51.79 | 62.80 | 64.93 | 63.72 | 57.11 | 45.59 | 30.35 | 33.62 | 15.45 |
| SE | 0.00 | 0.00 | 0.00 | 0.00 | 2.55 | 6.77 | 8.36 | 14.97 | 15.61 | 18.94 | 19.58 | 19.21 | 17.22 | 13.75 | 9.15 | 10.14 | 4.66 |

TABLE 1C

Plasma R-Ketorolac Concentrations (ng/mL)
IV Injection, 2 Doses q12h
(n = 12)

| Subject Number | Study Hour | | | | | | | | | | | | | | |
|---|---|---|---|---|---|---|---|---|---|---|---|---|---|---|---|
| | 0.0 | 0.5 | 1.0 | 2.0 | 4.0 | 6.0 | 8.0 | 12.0 | 12.5 | 13.0 | 14.0 | 16.0 | 18.0 | 20.0 | 24.0 |
| 101 | 0.0 | 1162.0 | 850.0 | 844.0 | 477.0 | 224.0 | 126.0 | 82.0 | 1422.0 | 817.0 | 451.0 | 268.0 | 215.0 | 171.0 | 99.0 |
| 102 | 0.0 | 732.0 | 497.0 | 278.0 | 149.0 | 67.0 | 48.0 | 54.0 | 1040.0 | 717.0 | 403.0 | 280.0 | 111.0 | 88.0 | 38.0 |
| 103 | 0.0 | 754.0 | 521.0 | 317.0 | 190.0 | 114.0 | 73.0 | 31.0 | 635.0 | 446.0 | 318.0 | 161.0 | 92.0 | 74.0 | 50.0 |
| 104 | 0.0 | 619.0 | 455.0 | 326.0 | 195.0 | 141.0 | 92.0 | 50.0 | 696.0 | 530.0 | 367.0 | 242.0 | 174.0 | 127.0 | 81.0 |
| 105 | 0.0 | 818.0 | 517.0 | 341.0 | 196.0 | 133.0 | 135.0 | 89.0 | 823.0 | 626.0 | 439.0 | 290.0 | 233.0 | 133.0 | 85.0 |
| 106 | 0.0 | 678.0 | 520.0 | 386.0 | 266.0 | 172.0 | 103.0 | 75.0 | 753.0 | 572.0 | 386.0 | 270.0 | 178.0 | 137.0 | 96.0 |
| 107 | 0.0 | 629.0 | 419.0 | 267.0 | 102.0 | 58.0 | 34.0 | 0.0 | 685.0 | 499.0 | 344.0 | 183.0 | 112.0 | 78.0 | 44.0 |
| 108 | 0.0 | 861.0 | 600.0 | 369.0 | 186.0 | 116.0 | 54.0 | 92.0 | 898.0 | 647.0 | 386.0 | 203.0 | 139.0 | 103.0 | 51.0 |
| 109 | 0.0 | 967.0 | 706.0 | 494.0 | 331.0 | 194.0 | 234.0 | 123.0 | 1144.0 | 974.0 | 807.0 | 582.0 | 386.0 | 294.0 | 160.0 |
| 110 | 0.0 | 650.0 | 473.0 | 290.0 | 171.0 | 126.0 | 66.0 | 43.0 | 626.0 | 500.0 | 392.0 | 292.0 | 250.0 | 193.0 | 136.0 |
| 111 | 0.0 | 822.0 | 657.0 | 464.0 | 296.0 | 166.0 | 113.0 | 71.0 | 913.0 | 651.0 | 492.0 | 274.0 | 188.0 | 162.0 | 93.0 |
| 112 | 0.0 | 627.0 | 485.0 | 300.0 | 161.0 | 100.0 | 71.0 | 34.0 | 691.0 | 487.0 | 326.0 | 179.0 | 126.0 | 93.0 | 49.0 |
| MEAN | 0.00 | 776.58 | 558.33 | 389.67 | 226.67 | 134.25 | 95.75 | 62.00 | 860.50 | 622.17 | 425.92 | 268.67 | 183.67 | 137.15 | 81.83 |
| SD | 0.00 | 163.19 | 124.11 | 159.68 | 101.73 | 49.01 | 53.75 | 33.25 | 240.72 | 154.51 | 130.41 | 109.27 | 81.49 | 62.24 | 38.22 |
| SE | 0.00 | 47.11 | 35.83 | 46.09 | 29.37 | 14.15 | 15.52 | 9.60 | 69.49 | 44.60 | 37.65 | 31.54 | 23.52 | 17.97 | 11.03 |

TABLE 2A

Plasma S-Ketorolac Concentrations (ng/mL)
ETS (ketorolac), 24 h
(n = 12)

| Subject Number | Study Hour | | | | | | | | | | | | | | | | |
|---|---|---|---|---|---|---|---|---|---|---|---|---|---|---|---|---|---|
| | 0.0 | 0.5 | 1.0 | 1.5 | 2.0 | 4.0 | 8.0 | 12.0 | 16.0 | 20.0 | 24.0 | 24.5 | 25.0 | 26.0 | 28.0 | 32.0 | 48.0 |
| 101 | 0.0 | 0.0 | 35.0 | 44.0 | 64.0 | 97.0 | 90.0 | 94.0 | 106.0 | 95.0 | 89.0 | 112.0 | 91.0 | 51.0 | 26.0 | 0.0 | 0.0 |
| 102 | 0.0 | 0.0 | 0.0 | 0.0 | 0.0 | 26.0 | 24.0 | 49.0 | 42.0 | 48.0 | 51.0 | 53.0 | 41.0 | 21.0 | 0.0 | 0.0 | 0.0 |
| 103 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 104 | 0.0 | 0.0 | 22.0 | 0.0 | 22.0 | 46.0 | 47.0 | 83.0 | 77.0 | 72.0 | 70.0 | 69.0 | 54.0 | 35.0 | 0.0 | 0.0 | 0.0 |
| 105 | 0.0 | 0.0 | 0.0 | 22.0 | 31.0 | 52.0 | 76.0 | 62.0 | 58.0 | 68.0 | 89.0 | 62.0 | 47.0 | 33.0 | 0.0 | 0.0 | 0.0 |
| 106 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 107 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 108 | 0.0 | 0.0 | 0.0 | 0.0 | 0.0 | 41.0 | 41.0 | 60.0 | 58.0 | 85.0 | 68.0 | 83.0 | 62.0 | 40.0 | 31.0 | 0.0 | 0.0 |
| 109 | 0.0 | 0.0 | 29.0 | 46.0 | 50.0 | 91.0 | 108.0 | 107.0 | 94.0 | 118.0 | 122.0 | 102.0 | 107.0 | 69.0 | 43.0 | 0.0 | 0.0 |
| 110 | 0.0 | 0.0 | 0.0 | 0.0 | 0.0 | 0.0 | 0.0 | 0.0 | 28.0 | 0.0 | 31.0 | 28.0 | 24.0 | 0.0 | 0.0 | 0.0 | 0.0 |
| 111 | 0.0 | 0.0 | 23.0 | 24.0 | 38.0 | 53.0 | 65.0 | 90.0 | 67.0 | 87.0 | 100.0 | 81.0 | 61.0 | 59.0 | 25.0 | 0.0 | 0.0 |
| 112 | 0.0 | 0.0 | 0.0 | 0.0 | 20.0 | 35.0 | 31.0 | 55.0 | 55.0 | 61.0 | 52.0 | 43.0 | 34.0 | 21.0 | 24.0 | 0.0 | 0.0 |
| MEAN | 0.00 | 0.00 | 9.08 | 11.33 | 18.75 | 36.75 | 40.17 | 50.00 | 48.75 | 52.83 | 56.00 | 52.75 | 43.42 | 27.42 | 12.42 | 0.00 | 0.00 |
| SD | 0.00 | 0.00 | 13.78 | 18.02 | 22.70 | 33.97 | 37.94 | 40.61 | 36.02 | 42.72 | 41.43 | 39.37 | 34.66 | 24.53 | 16.06 | 0.00 | 0.00 |
| SE | 0.00 | 0.00 | 3.98 | 5.20 | 6.55 | 9.81 | 10.95 | 11.72 | 10.40 | 12.33 | 11.96 | 11.37 | 10.00 | 7.08 | 4.64 | 0.00 | 0.00 |

TABLE 2B

Plasma S-Ketorolac Concentrations (ng/mL)
TTS (ketorolac), 24 h
(n = 11)

| Subject Number | Study Hour | | | | | | | | | | | | | | | | |
|---|---|---|---|---|---|---|---|---|---|---|---|---|---|---|---|---|---|
| | 0.0 | 1.0 | 2.0 | 3.0 | 4.0 | 6.0 | 8.0 | 12.0 | 16.0 | 20.0 | 24.0 | 24.5 | 25.0 | 26.0 | 28.0 | 32.0 | 48.0 |
| 101 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 102 | 0.0 | 0.0 | 0.0 | 0.0 | 0.0 | 27.0 | 41.0 | 63.0 | 62.0 | 97.0 | 83.0 | 70.0 | 55.0 | 40.0 | 0.0 | 0.0 | 0.0 |
| 103 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 104 | 0.0 | 0.0 | 0.0 | 0.0 | 0.0 | 0.0 | 0.0 | 0.0 | 0.0 | 41.0 | 55.0 | 0.0 | 0.0 | 0.0 | 0.0 | 0.0 | 0.0 |
| 106 | 0.0 | 0.0 | 0.0 | 0.0 | 0.0 | 0.0 | 0.0 | 0.0 | 0.0 | 25.0 | 21.0 | 21.0 | 21.0 | 0.0 | 0.0 | 0.0 | 0.0 |
| 107 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 108 | 0.0 | 0.0 | 0.0 | 0.0 | 0.0 | 0.0 | 0.0 | 0.0 | 38.0 | 31.0 | 68.0 | 25.0 | 63.0 | 46.0 | 0.0 | 0.0 | 0.0 |
| 109 | 0.0 | 0.0 | 0.0 | 0.0 | 0.0 | 0.0 | 0.0 | 35.0 | 45.0 | 73.0 | 68.0 | 58.0 | 45.0 | 36.0 | 21.0 | 0.0 | 0.0 |
| 110 | 0.0 | 0.0 | 0.0 | 0.0 | 0.0 | 0.0 | 0.0 | 0.0 | 0.0 | 0.0 | 33.0 | 31.0 | 62.0 | 27.0 | 0.0 | 28.0 | 0.0 |
| 111 | 0.0 | 0.0 | 0.0 | 0.0 | 0.0 | 0.0 | 0.0 | 0.0 | 26.0 | 45.0 | 60.0 | 68.0 | 52.0 | 36.0 | 21.0 | 0.0 | 0.0 |
| 112 | 0.0 | 0.0 | 0.0 | 0.0 | 0.0 | 0.0 | 0.0 | 0.0 | 0.0 | 0.0 | 30.0 | 0.0 | 0.0 | 28.0 | 0.0 | 0.0 | 0.0 |

TABLE 2B-continued

Plasma S-Ketorolac Concentrations (ng/mL)
TTS (ketorolac), 24 h
(n = 11)

| Subject Number | Study Hour | | | | | | | | | | | | | | | |
|---|---|---|---|---|---|---|---|---|---|---|---|---|---|---|---|---|
| | 0.0 | 1.0 | 2.0 | 3.0 | 4.0 | 6.0 | 8.0 | 12.0 | 16.0 | 20.0 | 24.0 | 24.5 | 25.0 | 26.0 | 28.0 | 32.0 | 48.0 |
| MEAN | 0.00 | 0.00 | 0.00 | 0.00 | 0.00 | 2.45 | 3.73 | 8.91 | 15.55 | 28.36 | 38.00 | 24.82 | 27.09 | 19.36 | 3.82 | 2.55 | 0.00 |
| SD | 0.00 | 0.00 | 0.00 | 0.00 | 0.00 | 8.14 | 12.36 | 20.79 | 23.09 | 33.44 | 30.51 | 28.53 | 28.17 | 19.23 | 8.49 | 8.44 | 0.00 |
| SE | 0.00 | 0.00 | 0.00 | 0.00 | 0.00 | 2.45 | 3.73 | 6.27 | 6.96 | 10.08 | 9.20 | 8.60 | 8.49 | 5.80 | 2.56 | 2.55 | 0.00 |

TABLE 2C

Plasma S-Ketorolac Concentrations (ng/mL)
IV Injection, 2 Doses q12h
(n = 12)

| Subject Number | Study Hour | | | | | | | | | | | | | | |
|---|---|---|---|---|---|---|---|---|---|---|---|---|---|---|---|
| | 0.0 | 0.5 | 1.0 | 2.0 | 4.0 | 6.0 | 8.0 | 12.0 | 12.5 | 13.0 | 14.0 | 16.0 | 18.0 | 20.0 | 24.0 |
| 101 | 0.0 | 595.0 | 442.0 | 364.0 | 206.0 | 53.0 | 0.0 | 0.0 | 781.0 | 330.0 | 129.0 | 51.0 | 28.0 | 0.0 | 0.0 |
| 102 | 0.0 | 317.0 | 196.0 | 80.0 | 28.0 | 0.0 | 0.0 | 0.0 | 444.0 | 248.0 | 113.0 | 44.0 | 0.0 | 0.0 | 0.0 |
| 103 | 0.0 | 324.0 | 213.0 | 99.0 | 40.0 | 0.0 | 0.0 | 0.0 | 268.0 | 182.0 | 91.0 | 33.0 | 0.0 | 0.0 | 0.0 |
| 104 | 0.0 | 284.0 | 212.0 | 126.0 | 46.0 | 24.0 | 0.0 | 0.0 | 327.0 | 226.0 | 127.0 | 60.0 | 32.0 | 0.0 | 0.0 |
| 105 | 0.0 | 365.0 | 202.0 | 104.0 | 39.0 | 0.0 | 0.0 | 0.0 | 357.0 | 251.0 | 115.0 | 62.0 | 40.0 | 0.0 | 0.0 |
| 106 | 0.0 | 264.0 | 207.0 | 125.0 | 63.0 | 26.0 | 0.0 | 0.0 | 317.0 | 206.0 | 110.0 | 57.0 | 35.0 | 21.0 | 25.0 |
| 107 | 0.0 | 249.0 | 144.0 | 75.0 | 0.0 | 0.0 | 0.0 | 0.0 | 291.0 | 200.0 | 100.0 | 36.0 | 0.0 | 0.0 | 0.0 |
| 108 | 0.0 | 400.0 | 226.0 | 107.0 | 31.0 | 0.0 | 0.0 | 45.0 | 416.0 | 257.0 | 113.0 | 35.0 | 0.0 | 0.0 | 0.0 |
| 109 | 0.0 | 387.0 | 236.0 | 150.0 | 62.0 | 29.0 | 0.0 | 0.0 | 504.0 | 376.0 | 262.0 | 132.0 | 59.0 | 34.0 | 0.0 |
| 110 | 0.0 | 285.0 | 185.0 | 91.0 | 39.0 | 23.0 | 0.0 | 0.0 | 325.0 | 238.0 | 168.0 | 110.0 | 74.0 | 49.0 | 24.0 |
| 111 | 0.0 | 388.0 | 290.0 | 182.0 | 81.0 | 32.0 | 24.0 | 0.0 | 455.0 | 314.0 | 185.0 | 64.0 | 42.0 | 72.0 | 20.0 |
| 112 | 0.0 | 256.0 | 178.0 | 85.0 | 28.0 | 0.0 | 0.0 | 0.0 | 294.0 | 181.0 | 84.0 | 27.0 | 0.0 | 0.0 | 0.0 |
| MEAN | 0.00 | 342.83 | 227.58 | 132.33 | 55.25 | 15.58 | 2.00 | 3.75 | 398.25 | 250.75 | 133.08 | 59.25 | 25.83 | 14.67 | 5.75 |
| SD | 0.00 | 96.17 | 76.12 | 79.24 | 51.76 | 17.94 | 6.93 | 12.99 | 141.87 | 61.02 | 50.03 | 31.71 | 25.84 | 24.50 | 10.46 |
| SE | 0.00 | 27.76 | 21.97 | 22.88 | 14.94 | 5.18 | 2.00 | 3.75 | 40.95 | 17.62 | 14.44 | 9.15 | 7.46 | 7.07 | 3.02 |

TABLE 3A $C_{max}$ and $T_{max}$ Values
for R-Ketorolac Concentration
ETS (ketorolac), 24 h
(n = 12)

| Subject Number | $C_{max}$ (ng/mL) | $T_{max}$ (h) |
|---|---|---|
| 101 | 326.0 | 24.5 |
| 102 | 161.0 | 24.0 |
| 103 | 34.0 | 12.0 |
| 104 | 219.0 | 16.0 |
| 105 | 267.0 | 24.0 |
| 106 | 35.0 | 24.0 |
| 107 | 65.0 | 24.0 |
| 108 | 262.0 | 24.5 |
| 109 | 386.0 | 25.0 |
| 110 | 79.0 | 24.0 |
| 111 | 297.0 | 24.0 |
| 112 | 205.0 | 16.0 |
| Mean | 194.67 | 21.83 |
| SD | 119.63 | 4.44 |
| CV | 61.45 | 20.35 |
| Gmean | 148.55 | 21.32 |
| Mean(ln) | 5.00 | 3.06 |
| SD(ln) | 0.87 | 0.24 |

TABLE 3B $C_{max}$ and $T_{max}$ Values
for R-Ketorolac Concentration
TTS (ketorolac), 24 h
(n = 11)

| Subject Number | $C_{max}$ (ng/mL) | $T_{max}$ (h) |
|---|---|---|
| 101 | 38.0 | 24.5 |
| 102 | 247.0 | 24.0 |
| 103 | 76.0 | 24.0 |
| 104 | 99.0 | 24.0 |
| 106 | 144.0 | 24.5 |
| 107 | 67.0 | 12.0 |
| 108 | 166.0 | 24.0 |
| 109 | 203.0 | 24.0 |
| 110 | 126.0 | 24.0 |
| 111 | 168.0 | 24.5 |
| 112 | 119.0 | 20.0 |
| Mean | 132.09 | 22.69 |
| SD | 61.93 | 3.76 |
| CV | 46.88 | 16.58 |
| Gmean | 117.30 | 22.30 |
| Mean(ln) | 4.76 | 3.10 |
| SD(ln) | 0.54 | 0.21 |

TABLE 3C $C_{max}$ and $T_{max}$ Values
for R-Ketorolac Concentration
IV Injection, 2 Doses q 12 h
(n = 12)

| Subject Number | $C_{max}$ (ng/mL) | $T_{max}$ (h) |
|---|---|---|
| 101 | 1422.0 | 12.5 |
| 102 | 1040.0 | 12.5 |
| 103 | 754.0 | 0.5 |
| 104 | 696.0 | 12.5 |
| 105 | 823.0 | 12.5 |
| 106 | 753.0 | 12.5 |
| 107 | 685.0 | 12.5 |
| 108 | 898.0 | 12.5 |
| 109 | 1144.0 | 12.5 |
| 110 | 650.0 | 0.5 |
| 111 | 913.0 | 12.5 |
| 112 | 691.0 | 12.5 |
| Mean | 872.42 | 10.50 |
| SD | 230.72 | 4.67 |
| CV | 26.45 | 44.49 |
| Gmean | 848.26 | 7.31 |
| Mean(ln) | 6.74 | 1.99 |
| SD(ln) | 0.24 | 1.25 |

TABLE 4A $C_{max}$ and $T_{max}$ Values
for S-Ketorolac Concentration
ETS (ketorolac), 24 h
(n = 9)

| Subject Number | $C_{max}$ (ng/mL) | $T_{max}$ (h) |
|---|---|---|
| 101 | 112.0 | 24.5 |
| 102 | 53.0 | 24.5 |
| 104 | 83.0 | 12.0 |
| 105 | 89.0 | 24.0 |
| 108 | 85.0 | 20.0 |
| 109 | 122.0 | 24.0 |
| 110 | 31.0 | 24.0 |
| 111 | 100.0 | 24.0 |
| 112 | 61.0 | 20.0 |
| Mean | 81.78 | 21.89 |
| SD | 29.08 | 4.13 |
| CV | 35.56 | 18.87 |
| Gmean | 76.14 | 21.44 |
| Mean(ln) | 4.33 | 3.07 |
| SD(ln) | 0.43 | 0.23 |

NOTE:
Concentrations for subjects 103, 106, 107 were zero.

TABLE 4B $C_{max}$ and $T_{max}$ Values
for S-Ketorolac Concentration
TTS (ketorolac), 24 h
(n = 8)

| Subject Number | $C_{max}$ (ng/mL) | $T_{max}$ (h) |
|---|---|---|
| 102 | 97.0 | 20.0 |
| 104 | 55.0 | 24.0 |
| 106 | 25.0 | 20.0 |
| 108 | 68.0 | 24.0 |
| 109 | 73.0 | 20.0 |
| 110 | 62.0 | 25.0 |
| 111 | 68.0 | 24.5 |
| 112 | 30.0 | 24.0 |
| Mean | 59.75 | 22.69 |

TABLE 4B-continued $C_{max}$ and $T_{max}$ Values
for S-Ketorolac Concentration
TTS (ketorolac), 24 h
(n = 8)

| Subject Number | $C_{max}$ (ng/mL) | $T_{max}$ (h) |
|---|---|---|
| SD | 23.36 | 2.25 |
| CV | 39.09 | 9.92 |
| Gmean | 55.00 | 22.59 |
| Mean(ln) | 4.01 | 3.12 |
| SD(ln) | 0.46 | 0.10 |

TABLE 4C $C_{max}$ and $T_{max}$ Values
for S-Ketorolac Concentration
IV Injection, 2 Doses q 12 h
(n = 12)

| Subject Number | $C_{max}$ (ng/mL) | $T_{max}$ (h) |
|---|---|---|
| 101 | 781.0 | 12.5 |
| 102 | 444.0 | 12.5 |
| 103 | 324.0 | 0.5 |
| 104 | 327.0 | 12.5 |
| 105 | 365.0 | 0.5 |
| 106 | 317.0 | 12.5 |
| 107 | 291.0 | 12.5 |
| 108 | 416.0 | 12.5 |
| 109 | 504.0 | 12.5 |
| 110 | 325.0 | 12.5 |
| 111 | 455.0 | 12.5 |
| 112 | 294.0 | 12.5 |
| Mean | 403.58 | 10.50 |
| SD | 137.84 | 4.67 |
| CV | 34.15 | 44.49 |
| Gmean | 386.97 | 7.31 |
| Mean(ln) | 5.96 | 1.99 |
| SD(ln) | 0.29 | 1.25 |

TABLE 5

Apparent Elimination Rate Constant (k)
and Half-Life ($t_{1/2}$) Values
for R-Ketorolac Concentration
IV Injection, 2 Doses q 12 h
(n = 12)

| Subject Number | $t_{1/2}$ (h) | k ($h^{-1}$) | Time Points | n | $r^2$ |
|---|---|---|---|---|---|
| 101 | 5.5 | 0.125 | 16.00–24.00 | 4 | 1.00 |
| 102 | 3.8 | 0.183 | 18.00–24.00 | 3 | 0.98 |
| 103 | 6.9 | 0.101 | 18.00–24.00 | 3 | 1.00 |
| 104 | 5.1 | 0.136 | 16.00–24.00 | 4 | 0.99 |
| 105 | 4.3 | 0.160 | 18.00–24.00 | 3 | 0.94 |
| 106 | 5.6 | 0.125 | 16.00–24.00 | 4 | 0.96 |
| 107 | 4.0 | 0.174 | 16.00–24.00 | 4 | 0.98 |
| 108 | 4.1 | 0.171 | 16.00–24.00 | 4 | 1.00 |
| 109 | 4.4 | 0.158 | 16.00–24.00 | 4 | 0.99 |
| 110 | 7.1 | 0.098 | 16.00–24.00 | 4 | 0.99 |
| 111 | 5.3 | 0.130 | 16.00–24.00 | 4 | 0.99 |
| 112 | 4.3 | 0.161 | 16.00–24.00 | 4 | 1.00 |
| Mean | 5.02 | 0.1435 | | | |
| SD | 1.10 | 0.0285 | | | |
| CV | 21.90 | 19.8270 | | | |
| Gmean | 4.92 | 0.1408 | | | |
| Mean(ln) | 1.59 | −1.9604 | | | |
| SD(ln) | 0.21 | 0.2091 | | | |

TABLE 6

Apparent Elimination Rate Constant (k) and Half-Life ($t_{1/2}$) Values for S-Ketorolac Concentration IV Injection, 2 Doses q 12 h (n = 12)

| Subject Number | $t_{1/2}$ (h) | k ($h^{-1}$) | Time Points | n | $r^2$ |
|---|---|---|---|---|---|
| 101 | 1.8 | 0.382 | 14.00–18.00 | 3 | 0.98 |
| 102 | 1.2 | 0.561 | 13.00–16.00 | 3 | 0.98 |
| 103 | 1.2 | 0.560 | 13.00–16.00 | 3 | 0.99 |
| 104 | 2.0 | 0.345 | 14.00–18.00 | 3 | 1.00 |
| 105 | 2.6 | 0.264 | 14.00–18.00 | 3 | 0.99 |
| 106 | 2.8 | 0.250 | 16.00–20.00 | 3 | 1.00 |
| 107 | 1.2 | 0.563 | 13.00–16.00 | 3 | 0.99 |
| 108 | 1.1 | 0.653 | 13.00–16.00 | 3 | 0.99 |
| 109 | 2.0 | 0.349 | 13.00–20.00 | 5 | 1.00 |
| 110 | 3.6 | 0.190 | 16.00–24.00 | 4 | 1.00 |
| 111 | 3.2 | 0.220 | 13.00–24.00 | 6 | 0.81 |
| 112 | 1.1 | 0.625 | 13.00–16.00 | 3 | 0.99 |
| Mean | 1.99 | 0.4135 | | | |
| SD | 0.88 | 0.1690 | | | |
| CV | 44.15 | 40.8757 | | | |
| Gmean | 1.82 | 0.3803 | | | |
| Mean(ln) | 0.60 | −0.9667 | | | |
| SD(ln) | 0.44 | 0.4372 | | | |

TABLE 7A

AUC and $C_{avg}$ Values for R-Ketorolac Concentration ETS (ketorolac), 24 h (n = 12)

| Subject Number | $AUC_t$ (ng·h/mL) | $AUC_{(0-48)}$ (ng·h/mL) | $AUC_{inf}$ (ng·h/mL) | $C_{avg}$ (ng/mL) |
|---|---|---|---|---|
| 101 | 7451.63 | 7451.63 | 8243.53 | 155.24 |
| 102 | 3177.39 | 3177.39 | 3297.53 | 66.20 |
| 103 | 586.50 | 586.50 | 833.75 | 12.22 |
| 104 | 4484.50 | 4484.50 | 4822.49 | 93.43 |
| 105 | 5430.25 | 5430.25 | 5798.90 | 113.13 |
| 106 | 381.25 | 381.25 | 605.63 | 7.94 |
| 107 | 607.75 | 607.75 | 791.24 | 12.66 |
| 108 | 5160.69 | 5160.69 | 5324.37 | 107.51 |
| 109 | 8456.77 | 8456.77 | 9076.31 | 176.18 |
| 110 | 1166.00 | 1166.00 | 1483.95 | 24.29 |
| 111 | 6994.62 | 6994.62 | 7224.87 | 145.72 |
| 112 | 3813.66 | 3813.66 | 4074.72 | 79.45 |
| Mean | 3975.917 | 3975.917 | 4298.107 | 82.832 |
| SD | 2850.239 | 2850.239 | 2976.406 | 59.380 |
| CV | 71.688 | 71.688 | 69.249 | 71.688 |
| Gmean | 2623.602 | 2623.602 | 3047.308 | 54.658 |
| Mean(ln) | 7.872 | 7.872 | 8.022 | 4.001 |
| SD(ln) | 1.113 | 1.113 | 0.981 | 1.113 |
| Max | 8456.767 | 8456.767 | 9076.311 | 176.153 |
| Min | 381.250 | 381.250 | 605.630 | 7.943 |

TABLE 7B

AUC and $C_{avg}$ Values for R-Ketorolac Concentration TTS (ketorolac), 24 h (n = 11)

| Subject Number | $AUC_t$ (ng·h/mL) | $AUC_{(0-24)}$ (ng·h/mL) | $AUC_{inf}$ (ng·h/mL) | $C_{avg}$ (ng/mL) |
|---|---|---|---|---|
| 101 | 293.30 | 172.00 | 509.27 | 7.17 |
| 102 | 4218.25 | 3310.00 | 4474.90 | 137.92 |
| 103 | 1102.25 | 692.00 | 1349.50 | 28.83 |
| 104 | 614.75 | 426.00 | 798.44 | 17.75 |
| 106 | 2679.78 | 837.44 | 2960.25 | 34.89 |
| 107 | 1157.25 | 832.00 | 1409.55 | 34.67 |
| 108 | 3231.98 | 1392.00 | 3348.89 | 58.00 |
| 109 | 3793.53 | 1971.78 | 3989.51 | 82.16 |
| 110 | 1745.62 | 1155.37 | 2268.69 | 48.14 |
| 111 | 3109.50 | 1510.00 | 3362.78 | 62.92 |
| 112 | 1649.93 | 1014.76 | 2016.67 | 42.28 |
| Mean | 2145.103 | 1210.305 | 2408.042 | 50.429 |
| SD | 1328.602 | 860.038 | 1317.606 | 35.835 |
| CV | 61.936 | 71.060 | 54.717 | 71.060 |
| Gmean | 1671.989 | 949.910 | 2005.097 | 39.580 |
| Mean(ln) | 7.422 | 6.856 | 7.603 | 3.678 |
| SD(ln) | 0.831 | 0.787 | 0.694 | 0.787 |
| Max | 4218.250 | 3310.000 | 4474.904 | 137.917 |
| Min | 293.300 | 172.000 | 509.273 | 7.167 |

TABLE 7C

AUC and $C_{avg}$ Values for R-Ketorolac Concentration IV Injection, 2 Doses q 12 h (n = 12)

| Subject Number | $AUC_t$ (ng·h/mL) | $AUC_{(0-24)}$ (ng·h/mL) | $AUC_{inf}$ (ng·h/mL) | $C_{avg}$ (ng/mL) |
|---|---|---|---|---|
| 101 | 8126.25 | 8126.25 | 8918.15 | 338.59 |
| 102 | 4637.50 | 4637.50 | 4845.01 | 193.23 |
| 103 | 4097.00 | 4097.00 | 4591.51 | 170.71 |
| 104 | 4869.52 | 4869.52 | 5464.67 | 202.90 |
| 105 | 5726.00 | 5726.00 | 6257.10 | 238.58 |
| 106 | 5545.25 | 5545.25 | 6314.55 | 231.05 |
| 107 | 3596.00 | 3596.00 | 3848.30 | 149.83 |
| 108 | 5008.22 | 5008.22 | 5306.35 | 208.68 |
| 109 | 9436.25 | 9436.25 | 10447.75 | 393.18 |
| 110 | 5214.50 | 5214.50 | 6609.36 | 217.27 |
| 111 | 6305.32 | 6305.32 | 7019.11 | 262.72 |
| 112 | 4125.50 | 4125.50 | 4430.08 | 171.90 |
| Mean | 5557.275 | 5557.275 | 6170.994 | 231.553 |
| SD | 1705.638 | 1705.638 | 1923.591 | 71.068 |
| CV | 30.692 | 30.692 | 31.171 | 30.692 |
| Gmean | 5350.361 | 5350.361 | 5926.687 | 222.932 |
| Mean(ln) | 8.585 | 8.585 | 8.687 | 5.407 |
| SD(ln) | 0.280 | 0.280 | 0.291 | 0.280 |
| Max | 9436.250 | 9436.250 | 10447.75 | 393.177 |
| Min | 3596.000 | 3596.000 | 3448.304 | 149.833 |

TABLE 8A

AUC and $C_{avg}$ Values for S-Ketorolac Concentration ETS (ketorolac), 24 h (n = 9)

| Subject Number | $AUC_t$ (ng·h/mL) | $AUC_{(0-48)}$ (ng·h/mL) | $AUC_{inf}$ (ng·h/mL) | $C_{avg}$ (ng/mL) |
|---|---|---|---|---|
| 101 | 2377.28 | 2377.28 | 2445.36 | 49.53 |
| 102 | 912.84 | 912.84 | 950.25 | 19.02 |
| 104 | 1542.50 | 1542.50 | 1644.06 | 32.14 |
| 105 | 1544.75 | 1544.75 | 1669.74 | 32.15 |
| 108 | 1431.26 | 1431.26 | 1478.71 | 29.82 |
| 109 | 2632.40 | 2632.40 | 2755.45 | 54.84 |
| 110 | 201.75 | 201.75 | 327.86 | 4.20 |
| 111 | 1890.73 | 1890.73 | 2004.50 | 39.39 |
| 112 | 1157.67 | 1157.67 | 1196.09 | 24.12 |
| Mean | 1521.243 | 1521.243 | 1608.003 | 31.693 |

TABLE 8A-continued

AUC and $C_{avg}$ Values for S-Ketorolac Concentration ETS (ketorolac), 24 h (n = 9)

| Subject Number | $AUC_t$ (ng·h/mL) | $AUC_{(0-48)}$ (ng·h/mL) | $AUC_{inf}$ (ng·h/mL) | $C_{avg}$ (ng/mL) |
|---|---|---|---|---|
| SD | 737.945 | 737.945 | 744.809 | 15.374 |
| CV | 48.509 | 48.509 | 46.319 | 48.509 |
| Gmean | 1270.138 | 1270.138 | 1398.258 | 26.461 |
| Mean(ln) | 7.147 | 7.147 | 7.243 | 3.276 |
| SD(ln) | 0.764 | 0.764 | 0.636 | 0.764 |
| Max | 2632.400 | 2632.400 | 2755.452 | 54.842 |
| Min | 201.750 | 201.750 | 327.864 | 4.203 |

TABLE 8B

AUC and $C_{avg}$ Values for S-Ketorolac Concentration TTS (ketorolac), 24 h (n = 8)

| Subject Number | $AUC_t$ (ng·h/mL) | $AUC_{(0-24)}$ (ng·h/mL) | $AUC_{inf}$ (ng·h/mL) | $C_{avg}$ (ng/mL) |
|---|---|---|---|---|
| 102 | 1348.00 | 1231.00 | 1419.25 | 51.29 |
| 104 | 274.00 | 274.00 | 433.60 | 11.42 |
| 106 | 163.03 | 142.38 | 247.16 | 5.93 |
| 108 | 511.93 | 412.00 | 582.24 | 17.17 |
| 109 | 902.75 | 748.00 | 962.94 | 31.17 |
| 110 | 232.75 | 66.00 | 379.88 | 2.75 |
| 111 | 567.00 | 404.00 | 662.56 | 16.83 |
| 112 | 81.00 | 59.50 | 125.82 | 2.48 |
| Mean | 510.046 | 417.110 | 601.669 | 17.380 |
| SD | 430.405 | 399.861 | 419.610 | 16.661 |
| CV | 84.386 | 95.865 | 69.741 | 95.865 |
| Gmean | 362.386 | 263.839 | 477.449 | 10.993 |
| Mean(ln) | 5.893 | 5.575 | 6.168 | 2.397 |
| SD(ln) | 0.929 | 1.093 | 0.765 | 1.093 |
| Max | 1348.000 | 1231.000 | 1419.245 | 51.292 |
| Min | 81.000 | 59.500 | 125.822 | 2.479 |

TABLE 8C

AUC and $C_{avg}$ Values for S-Ketorolac Concentration IV Injection, 2 Doses q 12 h (n = 12)

| Subject Number | $AUC_t$ (ng·h/mL) | $AUC_{(0-24)}$ (ng·h/mL) | $AUC_{inf}$ (ng·h/mL) | $C_{avg}$ (ng/mL) |
|---|---|---|---|---|
| 101 | 2654.50 | 2654.50 | 2727.82 | 110.60 |
| 102 | 1103.00 | 1103.00 | 1181.37 | 45.96 |
| 103 | 990.25 | 990.25 | 1049.15 | 41.26 |
| 104 | 1305.50 | 1305.50 | 1398.36 | 54.40 |
| 105 | 1271.25 | 1271.25 | 1422.76 | 52.97 |
| 106 | 1427.75 | 1427.75 | 1527.90 | 59.49 |
| 107 | 826.50 | 826.50 | 890.45 | 34.44 |
| 108 | 1295.03 | 1295.03 | 1348.60 | 53.96 |
| 109 | 2121.51 | 2121.51 | 2218.80 | 88.40 |
| 110 | 1697.75 | 1697.75 | 1823.86 | 70.74 |
| 111 | 2192.78 | 2192.78 | 2283.80 | 91.37 |
| 112 | 880.75 | 880.75 | 923.97 | 36.70 |
| Mean | 1480.548 | 1480.548 | 1566.403 | 61.689 |
| SD | 574.106 | 574.106 | 582.992 | 23.921 |
| CV | 38.777 | 38.777 | 37.219 | 38.777 |
| Gmean | 1388.048 | 1388.048 | 1474.236 | 57.835 |
| Mean(ln) | 7.236 | 7.236 | 7.296 | 4.058 |
| SD(ln) | 0.370 | 0.370 | 0.361 | 0.370 |
| Max | 2654.500 | 2654.500 | 2727.817 | 110.604 |
| Min | 826.500 | 826.500 | 890.453 | 34.438 |

TABLE 9A

R-Ketorolac and S-Ketorolac AUC Ratios (n = 12)

| Subject Number | ETS (ketorolac) R/S Ratio | TTS (ketorolac) R/S Ratio | IV Injection R/S Ratio |
|---|---|---|---|
| 101 | 3.37 | — | 3.27 |
| 102 | 3.47 | 3.15 | 4.10 |
| 103 | — | — | 4.38 |
| 104 | 2.93 | 1.84 | 3.91 |
| 105 | 3.47 | — | 4.40 |
| 106 | — | 11.98 | 4.13 |
| 107 | — | — | 4.32 |
| 108 | 3.60 | 5.75 | 3.93 |
| 109 | 3.29 | 4.14 | 4.71 |
| 110 | 4.53 | 5.97 | 3.62 |
| 111 | 3.60 | 5.08 | 3.07 |
| 112 | 3.41 | 16.03 | 4.79 |
| Mean | 3.520 | 6.743 | 4.054 |
| SD | 0.427 | 4.805 | 0.529 |
| CV | 12.140 | 71.266 | 13.048 |
| SE | 0.142 | 1.699 | 0.153 |
| Min | 2.93 | 1.84 | 3.07 |
| Max | 4.53 | 16.03 | 4.79 |

TABLE 9B

R-Ketorolac and S-Ketorolac AUC Ratios (n = 6)

| Subject Number | ETS (ketorolac) R/S Ratio | TTS (ketorolac) R/S Ratio | IV Injection R/S Ratio |
|---|---|---|---|
| 102 | 3.47 | 3.15 | 4.10 |
| 104 | 2.93 | 1.84 | 3.91 |
| 108 | 3.60 | 5.75 | 3.93 |
| 109 | 3.29 | 4.14 | 4.71 |
| 111 | 3.60 | 5.08 | 3.07 |
| 112 | 3.41 | 16.03 | 4.79 |
| Mean | 3.385 | 5.999 | 4.087 |
| SD | 0.251 | 5.105 | 0.628 |
| CV | 7.412 | 85.105 | 15.359 |
| SE | 0.102 | 2.084 | 0.256 |
| Min | 2.93 | 1.84 | 3.07 |
| Max | 3.60 | 16.03 | 4.79 |

NOTE:
Table is computed for subjects with $AUC_{inf}$ for both enantiomers

TABLE 10A

AUC and Amount Delivered (AD) Values for R-Ketorolac Concentration (n = 12)

| Subject Number | ETS (ketorolac) $AUC_{inf}$ (ng·h/mL) | TTS (ketorolac) $AUC_{inf}$ (ng·h/mL) | IV Injection $AUC_{inf}$ (ng·h/mL) | ETS/IV[a] AD (mg) | TTS/IV[b] AD (mg) |
|---|---|---|---|---|---|
| 101 | 8243.5 | 509.3 | 8918.2 | 11.09 | 0.69 |
| 102 | 3297.5 | 4474.9 | 4845.0 | 8.17 | 11.08 |
| 103 | 833.8 | 1349.5 | 4591.5 | 2.18 | 3.53 |
| 104 | 4822.5 | 798.4 | 5464.7 | 10.59 | 1.75 |
| 105 | 5798.9 | — | 6257.1 | 11.12 | — |
| 106 | 605.6 | 2960.2 | 6314.6 | 1.15 | 5.63 |
| 107 | 791.2 | 1409.6 | 3848.3 | 2.47 | 4.40 |
| 108 | 5324.4 | 3348.9 | 5306.3 | 12.04 | 7.57 |
| 109 | 9076.3 | 3989.5 | 10447.8 | 10.42 | 4.58 |
| 110 | 1483.9 | 2268.7 | 6609.4 | 2.69 | 4.12 |
| 111 | 7224.9 | 3362.8 | 7019.1 | 12.35 | 5.75 |
| 112 | 4074.7 | 2016.7 | 4430.1 | 11.04 | 5.46 |
| Mean | 4298.11 | 2408.04 | 6170.99 | 7.943 | 4.960 |
| SD | 2976.41 | 1317.61 | 1923.59 | 4.431 | 2.782 |
| CV | 69.25 | 54.72 | 31.17 | 55.779 | 56.102 |

TABLE 10A-continued

AUC and Amount Delivered (AD) Values for R-Ketorolac Concentration (n = 12)

| Subject Number | ETS (ketorolac) AUC$_{inf}$ (ng · h/mL) | TTS (ketorolac) AUC$_{inf}$ (ng · h/mL) | IV Injection AUC$_{inf}$ (ng · h/mL) | ETS/IV[a] AD (mg) | TTS/IV[b] AD (mg) |
|---|---|---|---|---|---|
| SE | 859.21 | 397.27 | 555.29 | 1.279 | 0.839 |
| G-mean | 3047.31 | 2005.10 | 5926.69 | 6.170 | 4.080 |
| Mean (ln) | 8.02 | 7.60 | 8.69 | 1.820 | 1.406 |
| SD (ln) | 0.98 | 0.69 | 0.29 | 0.855 | 0.750 |
| Min | 605.6 | 509.3 | 3848.3 | 1.15 | 0.69 |
| Max | 9076.3 | 4474.9 | 10447.8 | 12.35 | 11.08 |

[a]ETS/IV = AUC$_{inf}$ for ETS (ketorolac) vs AUC$_{inf}$ for IV Injection.
[b]TTS/IV = AUC$_{inf}$ TTS (ketorolac) vs AUC$_{inf}$ for IV Injection.

TABLE 10B

AUC and Amount Delivered (AD) Values for R-Ketorolac Concentration (n = 6)

| Subject Number | ETS (ketorolac) AUC$_{inf}$ (ng · h/mL) | TTS (ketorolac) AUC$_{inf}$ (ng · h/mL) | IV Injection AUC$_{inf}$ (ng · h/mL) | ETS/IV[a] AD (mg) | TTS/IV[b] AD (mg) |
|---|---|---|---|---|---|
| 102 | 3297.5 | 4474.9 | 4845.0 | 8.17 | 11.08 |
| 104 | 4822.5 | 798.4 | 5464.7 | 10.59 | 1.75 |
| 108 | 5324.4 | 3348.9 | 5306.3 | 12.04 | 7.57 |
| 109 | 9076.3 | 3989.5 | 10447.8 | 10.42 | 4.58 |
| 111 | 7224.9 | 3362.8 | 7019.1 | 12.35 | 5.75 |
| 112 | 4074.7 | 2016.7 | 4430.1 | 11.04 | 5.46 |
| Mean | 5636.72 | 2998.53 | 6252.16 | 10.769 | 6.034 |
| SD | 2145.94 | 1358.06 | 2236.34 | 1.491 | 3.121 |
| CV | 38.07 | 45.29 | 35.77 | 13.845 | 51.724 |
| SE | 876.07 | 554.43 | 912.98 | 0.609 | 1.274 |
| G-mean | 5318.15 | 2620.37 | 5978.08 | 10.675 | 5.260 |
| Mean (ln) | 8.58 | 7.87 | 8.70 | 2.368 | 1.660 |
| SD (ln) | 0.37 | 0.64 | 0.31 | 0.148 | 0.620 |
| Min | 3297.5 | 798.4 | 4430.1 | 8.17 | 1.75 |
| Max | 9076.3 | 4474.9 | 10447.8 | 12.35 | 11.08 |

[a]ETS/IV = AUC$_{inf}$ for ETS (ketorolac) vs AUC$_{inf}$ for IV Injection.
[b]TTS/IV = AUC$_{inf}$ TTS (ketorolac) vs AUC$_{inf}$ for IV Injection.

TABLE 11A

AUC and Amount Delivered (AD) Values for S-Ketorolac Concentration (n = 12)

| Subject Number | ETS (ketorolac) AUC$_{inf}$ (ng · h/mL) | TTS (ketorolac) AUC$_{inf}$ (ng · h/mL) | IV Injection AUC$_{inf}$ (ng · h/mL) | ETS/IV[a] AD (mg) | TTS/IV[b] AD (mg) |
|---|---|---|---|---|---|
| 101 | 2445.4 | — | 2727.8 | 10.76 | — |
| 102 | 950.2 | 1419.2 | 1181.4 | 9.65 | 14.42 |
| 103 | — | — | 1049.1 | — | — |
| 104 | 1644.1 | 433.6 | 1398.4 | 14.11 | 3.72 |
| 105 | 1669.7 | — | 1422.8 | 14.08 | — |
| 106 | — | 247.2 | 1527.9 | — | 1.94 |
| 107 | — | — | 890.5 | — | — |
| 108 | 1478.7 | 582.2 | 1348.6 | 13.16 | 5.18 |
| 109 | 2755.5 | 962.8 | 2218.8 | 14.90 | 5.21 |
| 110 | 327.9 | 379.9 | 1823.9 | 2.16 | 2.50 |

TABLE 11A-continued

AUC and Amount Delivered (AD) Values for S-Ketorolac Concentration (n = 12)

| Subject Number | ETS (ketorolac) AUC$_{inf}$ (ng · h/mL) | TTS (ketorolac) AUC$_{inf}$ (ng · h/mL) | IV Injection AUC$_{inf}$ (ng · h/mL) | ETS/IV[a] AD (mg) | TTS/IV[b] AD (mg) |
|---|---|---|---|---|---|
| 111 | 2004.5 | 662.6 | 2283.8 | 10.53 | 3.48 |
| 112 | 1196.1 | 125.8 | 924.0 | 15.53 | 1.63 |
| Mean | 1608.00 | 601.67 | 1566.40 | 11.654 | 4.760 |
| SD | 744.81 | 419.61 | 582.99 | 4.124 | 4.126 |
| CV | 46.32 | 69.74 | 37.22 | 35.386 | 86.676 |
| SE | 248.27 | 148.35 | 168.30 | 1.375 | 1.459 |
| Gmean | 1398.26 | 477.45 | 1474.24 | 10.404 | 3.760 |
| Mean(ln) | 7.24 | 6.17 | 7.30 | 2.342 | 1.324 |
| SD(ln) | 0.64 | 0.77 | 0.36 | 0.614 | 0.689 |
| Min | 327.9 | 125.8 | 890.5 | 2.16 | 1.63 |
| Max | 2755.5 | 1419.2 | 2727.8 | 15.53 | 14.42 |

—: AUC incalculable
[a]ETS/IV = AUC$_{inf}$ for ETS (ketorolac) vs AUC$_{inf}$ for IV injection.
[b]TTS/IV = AUC$_{inf}$ for TTS (ketorolac) vs AUC$_{inf}$ for IV injection.

TABLE 11B

AUC and Amount Delivered (AD) Values for S-Ketorolac Concentration (n = 6)

| Subject Number | ETS (ketorolac) AUC$_{inf}$ (ng · h/mL) | TTS (ketorolac) AUC$_{inf}$ (ng · h/mL) | IV Injection AUC$_{inf}$ (ng · h/mL) | ETS/IV[a] AD (mg) | TTS/IV[b] AD (mg) |
|---|---|---|---|---|---|
| 102 | 950.2 | 1419.2 | 1181.4 | 9.65 | 14.42 |
| 104 | 1644.1 | 433.6 | 1398.4 | 14.11 | 3.72 |
| 108 | 1478.7 | 582.2 | 1348.6 | 13.16 | 5.18 |
| 109 | 2755.5 | 962.8 | 2218.8 | 14.90 | 5.21 |
| 111 | 2004.5 | 662.6 | 2283.8 | 10.53 | 3.48 |
| 112 | 1196.1 | 125.8 | 924.0 | 15.53 | 1.63 |
| Mean | 1671.51 | 697.72 | 1559.15 | 12.981 | 5.607 |
| SD | 643.43 | 447.73 | 561.54 | 2.391 | 4.512 |
| CV | 38.49 | 64.17 | 36.02 | 18.420 | 80.479 |
| SE | 262.68 | 182.78 | 229.25 | 0.976 | 1.842 |
| Gmean | 1574.95 | 553.52 | 1478.16 | 12.786 | 4.494 |
| Mean(ln) | 7.36 | 6.32 | 7.30 | 2.548 | 1.503 |
| SD(ln) | 0.38 | 0.83 | 0.36 | 0.194 | 0.711 |
| Min | 950.2 | 125.8 | 924.0 | 9.65 | 1.63 |
| Max | 2755.5 | 1419.2 | 2283.8 | 15.53 | 14.42 |

[a]ETS/IV = AUC$_{inf}$ for ETS (ketorolac) vs AUC$_{inf}$ for IV injection.
[b]TTS/IV = AUC$_{inf}$ for TTS (ketorolac) vs AUC$_{inf}$ for IV injection.

TABLE 12

Pharmacokinetic Parameters Following Administration of IV Injection Compartmental Analysis (n = 12)

| | R-Ketorolac | | | | S-Ketorolac | | | |
|---|---|---|---|---|---|---|---|---|
| Subject Number | Volume (L) | K1 ($h^{-1}$) | K2 ($h^{-1}$) | K21 ($h^{-1}$) | Volume (L) | K1 ($h^{-1}$) | K2 ($h^{-1}$) | K21 ($h^{-1}$) |
| 101 | 0.970 | 5.814 | 0.297 | 1.336 | 1.235 | 5.889 | 0.420 | 1.062 |
| 102 | 4.788 | 0.907 | 0.063 | 0.164 | 9.586 | 1.072 | 0.049 | 0.076 |
| 103 | 4.829 | 2.372 | 0.287 | 1.208 | 12.454 | 1.947 | 0.603 | 1.483 |
| 104 | 6.923 | 1.051 | 0.135 | 0.477 | 13.240 | 1.494 | 0.404 | 1.034 |
| 105 | 4.971 | 1.313 | 0.131 | 0.493 | 9.379 | 1.655 | 0.388 | 0.803 |
| 106 | 5.850 | 1.627 | 0.177 | 0.879 | 14.862 | 0.847 | 0.159 | 0.284 |
| 107 | 7.116 | 0.676 | 0.049 | 0.108 | 7.172 | 5.415 | 0.769 | 2.769 |
| 108 | 4.775 | 1.043 | 0.182 | 0.424 | 7.083 | 2.734 | 0.671 | 1.688 |
| 109 | 5.156 | 0.570 | 0.067 | 0.225 | 10.448 | 0.678 | 0.043 | 0.096 |
| 110 | 7.943 | 0.673 | 0.045 | 0.179 | 14.778 | 0.785 | 0.025 | 0.098 |
| 111 | 4.995 | 1.468 | 0.202 | 0.856 | 10.623 | 0.713 | 0.067 | 0.123 |
| 112 | 6.729 | 0.950 | 0.161 | 0.408 | 13.162 | 1.996 | 0.643 | 1.535 |
| Mean | 5.4204 | 1.5386 | 0.1497 | 0.5630 | 10.3353 | 2.1020 | 0.3534 | 0.9210 |
| SD | 1.7791 | 1.4364 | 0.0860 | 0.4137 | 3.8860 | 1.7747 | 0.2771 | 0.8450 |
| CV | 32.8229 | 93.3557 | 57.4578 | 73.4884 | 37.5995 | 84.4298 | 78.4052 | 91.7490 |
| SE | 0.5136 | 0.4146 | 0.0248 | 0.1194 | 1.1218 | 0.5123 | 0.0800 | 0.2439 |
| Max | 7.943 | 5.814 | 0.297 | 1.336 | 14.862 | 5.889 | 0.769 | 2.769 |
| Min | 0.970 | 0.570 | 0.045 | 0.108 | 1.235 | 0.678 | 0.025 | 0.076 |

TABLE 13

Rate of Absorption Following Administration of ETS (ketorolac) Compartmental Analysis (n = 12)

| | R-Ketorolac | | S-Ketorolac | |
|---|---|---|---|---|
| Subject Number[a] | Ka ($h^{-1}$) | Rate (µg/h) | Ka ($h^{-1}$) | Rate (µg/h) |
| 101 | 2.864 | 745.87 | 1.626 | 876.62 |
| 102 | 0.892 | 337.91 | 0.537 | 358.79 |
| 103 | 0.722 | 66.62 | — | — |
| 104 | 0.843 | 455.22 | 0.901 | 568.18 |
| 105 | 2.691 | 534.76 | 1.313 | 568.72 |
| 106 | 0.243 | 57.17 | — | — |
| 107 | 0.835 | 76.68 | — | — |
| 108 | 0.695 | 489.14 | 0.351 | 559.18 |
| 109 | 0.837 | 856.01 | 1.008 | 963.00 |
| 110 | 2.093 | 126.00 | 0.174 | 126.01 |
| 111 | 0.877 | 600.20 | 0.856 | 695.26 |
| 112 | 5.292 | 359.57 | 0.655 | 407.17 |
| Mean | 1.5737 | 392.096 | 0.8245 | 569.214 |
| SD | 1.4413 | 271.333 | 0.4583 | 258.002 |
| CV | 91.5881 | 69.201 | 55.5873 | 45.326 |
| SE | 0.4161 | 78.327 | 0.1528 | 86.001 |
| Max | 5.292 | 856.01 | 1.626 | 963.00 |
| Min | 0.243 | 57.17 | 0.174 | 126.01 |

[a]Subjects 103, 106 and 107: Ka not estimable for S-ketorolac.

TABLE 14

Rate of Absorption Following Administration of TTS (ketorolac) Compartmental Analysis (n = 9)

| | R-Ketorolac | | | S-Ketorolac | | |
|---|---|---|---|---|---|---|
| Subject Number[a] | Ka ($h^{-1}$) | $T_{lag}$ (h) | Rate (µg/h) | Ka ($h^{-1}$) | $T_{lag}$ (h) | Rate (µg/h) |
| 101 | 0.842 | 15.6 | 111.89 | — | — | — |
| 102 | 2.309 | 4.9 | 545.78 | 1.865 | 5.0 | 637.72 |
| 103 | 0.361 | 7.2 | 177.57 | — | — | — |
| 106 | 0.087 | 7.1 | 394.18 | 3.912 | 15.8 | 211.16 |
| 108 | 0.182 | 6.3 | 388.33 | 0.688 | 11.9 | 433.09 |
| 109 | 0.541 | 9.1 | 490.71 | 1.289 | 9.8 | 541.09 |
| 110 | 0.570 | 7.3 | 272.22 | — | — | — |
| 111 | 0.169 | 2.7 | 338.16 | 0.743 | 13.9 | 528.90 |
| 112 | 0.449 | 10.2 | 287.08 | — | — | — |
| Mean | 0.6122 | 7.83 | 333.991 | 1.6995 | 11.31 | 470.391 |
| SD | 0.6789 | 3.64 | 139.561 | 1.3257 | 4.19 | 162.029 |
| CV | 110.8859 | 46.50 | 41.786 | 78.0049 | 37.06 | 34.446 |
| SE | 0.2263 | 1.21 | 46.520 | 0.5929 | 1.87 | 72.461 |
| Max | 2.309 | 15.6 | 545.78 | 3.912 | 15.8 | 637.72 |
| Min | 0.087 | 2.7 | 111.89 | 0.688 | 5.0 | 211.16 |

[a]Subjects 101, 103 and 112: Ka not estimable for S-ketorolac.
Subjects 104 and 107: Ka not estimable for both R- and S-ketorolac.
Subject 105 discontinued study before TTS treatment.
Subject 110: Concentrations of S-ketorolac were observed only after patch removal.

What is claimed is:

1. A method for preferentially delivering through a body surface a preferred stereoisomer of a drug from a formulation containing stereoisomers of the drug as a mixture of said preferred stereoisomer and at least one less preferred stereoisomer, comprising;

(a) applying to an area of the body surface the formulation containing the drug as a mixture of stereoisomers; and (b) delivering the preferred stereoisomer of the drug by electrotransport through said area simultaneously with or subsequent to step (a), in a manner effective to enhance the transport of said preferred stereoisomer from the mixture relative to the transport of said at least one less preferred stereoisomer from the mixture.

2. A method for preferentially delivering through a body surface a preferred stereoisomer of a drug from a formulation containing stereoisomers of the drug as a mixture of said preferred isomer and at least one less preferred stereoisomer, comprising;
  (a) placing a drug reservoir in a drug-transmitting relation with an area of the body surface, the reservoir comprising the formulation containing the drug as a mixture of stereoisomers;
  (b) electrically connecting the drug reservoir to a source of electrical power; and
  (c) delivering the preferred stereoisomer of drug through the skin by means of electrotransport, wherein said preferred isomer is delivered from the mixture at a first rate which is sufficient to induce a therapeutic effect, and said at least one less preferred stereoisomer is delivered from the mixture at a second rate which is lower than said first rate.

3. The method of claim 1, wherein the body surface is skin.

4. The method of claim 3, wherein the source of electrical power provides a skin current density of about 50 to 625 $\mu A/cm^2$.

5. The method of claim 4, wherein the source of electrical power provides a skin current density of about 100 $\mu A/cm^2$.

6. The method of claim 1, wherein the formulation further comprises a permeation enhancer present in an amount effective to decrease the electrical resistance of the body surface to the drug and thereby enhance the rate of penetration of the drug therethrough during electrotransport drug delivery.

7. The method of claim 1, wherein the drug is selected from the group consisting of acebutolol, acenocoumarol, albuterol/salbutamol, alprenolol, amosulolol, amoxicillin, ampicillin, Ansaid, astemizole, atenolol, baclofen, benazepril, benzyl glutamate, betaxolol, bethanecol, bisprolol, bopindolol, bucumolol, bufetolol, bufuralol, bunitrolol, bupranolol, butaclamol, butoconazole, butofilolol, calcitonin, camazepam, captopril, captopril, caraxolol, carvedilol, cefadroxil, cicloprofen, ciprofloxacin, corticosteroids, cromakalim, curteolol, cytrabine, deprenyl, dexfenfluramine, dihydroxythebaine, diltiazem, disopyramide, dobutamine, enalapril, ephedrine, estradiol, ethambutol, fenbuphen, fenfluramine, fenoprofen, fluorogesterone, fluoxetine, flurbiprofen, gonadorelin, hexobarbital, ibuprofen, imovane, indenolol, indoprofen, ketamine, ketodesogestrel/estrogen, ketoprofen, ketorolac, lisinopril, lorazepam, lovastatin, meclizine, mepindolol, metaproteranol, methadone, methyldopa, metipranolol, metoprolol, minoxiprofen, 3-hydroxy-N-methyl morphinan, nadolol, naproxen, nebivolol, nicardipine, nicotine, nilvadipine, nitanol, norfloxacin, norgestrel, ofloxacin, Orudis, oxaprotiline, oxpranolol, oxybutynin, perindopril, phenprocoumon, phenylpropanolamine, pindolol, pirprofen, polycloranphetamine, prilocaine, progestinpropanolol, propoxyphene, sertraline, sotalol, steroids, suprofen, tenormin, terbutaline, terfenadine, testosterone, thioridazine, timolol, tocainide, toliprolol, toloxaton, tomoxetine, triamcinolone, verapamil, viloxazin, warfarin, xibenolol, zacopride, and 1,4-dihydropyridine chiral compounds, and pharmaceutically acceptable salts and esters thereof.

8. The method of claim 1, wherein the drug is an antiinflammatory.

9. The method of claim 8, wherein the antiinflammatory is an NSAID.

10. The method of claim 9, wherein the drug is ketorolac or a pharmacologically acceptable salt or ester thereof.

11. The method of claim 10, wherein the preferred enantiomer is the S-isomer.

12. The method of claim 11, wherein the drug is ketorolac tromethamine.

13. A method for preferentially delivering through a body surface a preferred stereoisomer of a drug, comprising:
  (a) identifying the preferred stereoisomer and at least one less preferred stereoisomer of the drug;
  (b) applying to an area of the body surface a formulation containing a mixture of the stereoisomers of the drug; and
  (c) preferentially delivering from the mixture said preferred stereoisomer relative to said less preferred stereoisomer via electrotransport through said area.

14. A method of improved electrotransport delivery of a drug that exists as a mixture of stereoisomers, comprising:
  (a) identifying a preferred stereoisomer and at least one less preferred stereoisomer for the drug;
  (b) increasing the relative proportion of the preferred stereoisomer of the drug in the mixture of stereoisomers of the drug to provide a mixture enhanced for the preferred stereoisomer;
  (c) placing the enhanced mixture of drug in a drug reservoir;
  (d) placing the drug reservoir in drug-transmitting relation to an intact area of skin; and
  (e) preferentially delivering from the enhanced mixture said preferred stereoisomer relative to said less preferred stereoisomer via electrotransport.

15. The method of claim 1, wherein the current used during electrotransport is less than that necessary to provide therapeutically effective levels of the drug if the preferred and less preferred isomers were deliverable via electrotransport at the same rate.

16. The method of claim 1, wherein the amount of the formulation applied is less than that necessary to provide therapeutically effective levels of the drug if the preferred and less preferred isomers were deliverable via electrotransport at the same rate.

17. The method of claim 1, wherein the concentration of drug used in the formulation is less than that necessary to provide therapeutically effective levels of the drug if the preferred and less preferred isomers were deliverable via electrotransport at the same rate.

18. The method of claim 1, wherein the formulation is provided in the form of a patch of a size less than that necessary to provide therapeutically effective levels of the drug if the preferred and less preferred isomers were deliverable via electrotransport at the same rate.

19. A method for preferentially delivering through a body surface a preferred stereoisomer of a drug from a formulation containing stereoisomers of the drug as a mixture of said preferred stereoisomer and at least one less preferred stereoisomer, comprising;
  (a) determining the relative fluxes from the mixture of the stereoisomers of said drug through said body surface;
  (b) determining the relative bioactivities of the stereoisomers of the mixture of said drug;
  (c) selecting a preferred isomer based on the determined fluxes and relative bioactivities; and
  (d) delivering the drug by electrotransport so that therapeutically effective levels of the preferred stereoisomer are delivered through the body surface from the mixture.

20. A method of preferentially lowering the amount delivered through a body surface of a less preferred stereoisomer of a drug from a formulation containing the drug as a mixture of a preferred stereoisomer and said less preferred stereoisomer, comprising:

(a) applying to an area of the body surface the formulation containing the drug as a mixture of the stereoisomers; and (b) delivering the drug by electrotransport through said area simultaneously with or subsequent to step (a), in a manner effective to decrease the transport from the mixture of the less preferred stereoisomer relative to the transport of the preferred stereoisomer from the mixture.

21. The method of claim 20, wherein said less preferred isomer is toxic.

22. The method of claim 20, wherein said less preferred isomer is a mutagen.

* * * * *